(12) United States Patent
Morris et al.

(10) Patent No.: US 6,927,207 B1
(45) Date of Patent: Aug. 9, 2005

(54) RECOMBINANT MISTLETOE LECTINES

(75) Inventors: Peter Morris, Midlothian (GB);
Thomas Stiefel, St

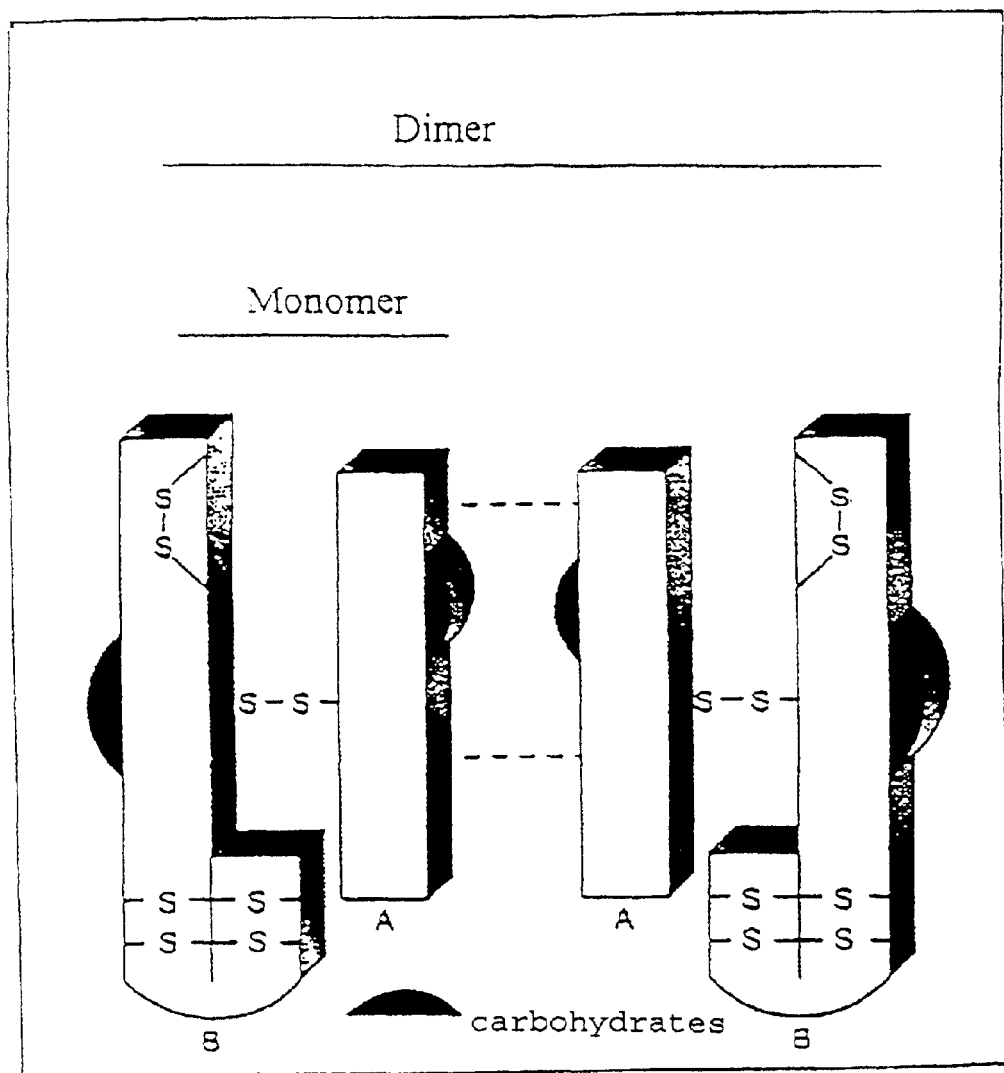
Fig. A

Fig. 1a mistletoe lectin I

TACGAGAGGCTAAGACTCAGAGTTACGCATCAAACCACGGGCGAGGAATACTTCCGGTTCATC

ACGCTTCTCCGAGATTATGTCTCAAGCGGAAGCTTTTCCAATGAGATACCACTCTTGCGTCAG

TCTACGATCCCCGTCTCCGATGCGCAAAGATTTGTCTTGGTGGAGCTCACCAACCAGGGGGA

GACTCGATCACGGCCGCCATCGACGTTACCAATCTGTACGTCGTGGCTTACCAAGCAGGCGAC

CAATCCTACTTTTTGCGCGACGCACCACGCGGCGCGGAAACGCACCTCTTCACCGGCACCACC

CGATCCTCTCTCCCATTCAACGGAAGCTACCCTGATCTGGAGCGATACGCCGGACATAGGGAC

CAGATCCCTCTCGGTATAGACCAACTCATTCAATCCGTCACGGCGCTTCGTTTTCCGGCGGC

AGCACGCGTACCCAAGCTCGTTCGATTTTAATCCTCATTCAGATGATCTCCGAGGCCGCCAGA

TTCAATCCCATCTTATGGAGGGCTCGCCAATACATTAACAGTGGGGCGTCATTTCTGCCAGAC

GTGTACATGCTGGAGCTGGAGACGAGTTGGGGCCAACAATCCACGCAAGTCCAGCATTCAACC

GATGGCGTTTTTAATAACCCAATTCGGTTGGCTATACCCCCGGTAACTTCGTGACGTTGACC

AATGTTCGCGACGTGATCGCCAGCTTGGCGATCATGTTGTTTGTATGCGGAGAGCGGCCATCT

TCCTCTGACGTGCGCTATTGGCCGCTGGTCATACGACCCGTGATAGCCGATGATGTTACCTGC

AGTGCTTCGGAACCTACGGTGCGGATTGTGGGTCGAAATGGCATGTGCGTGGACGTCCGAGAT

GACGATTTCCACGATGGGAATCAGATACAGTTGTGGCCCTCCAAGTCCAACAATGATCCGAAT

CAGTTGTGGACGATCAAAAGGGATGGAACCATTCGATCCAATGGCAGCTGCTTGACCACGTAT

GGCTATACTGCTGGCGTCTATGTGATGATCTTCGACTGTAATACTGCTGTGCGGGAGGCCACT

ATTTGGCAGATATGGGGCAATGGACCATCATCAATCCAAGATCCAATCTGGTTTTGGCAGCA

TCATCTGGAATCAAAGGCACTACGCTTACGGTGCAAACACTGGATTACACGTTGGGACAGGGC

TGGCTTGCCGGTAATGATACCGCCCACGCGAGGTGACCATATATGGTTTCAGGGACCTTTGC

ATGGAATCAAATGGAGGGAGTGTGTGGGTGGAGACGTGCGTGAGTAGCCAACAGAACCAAAGA

TGGGCTTTGTACGGGGATGGTTCTATACGCCCAAACAAAACCAAGACCAATGCCTCACCTGT

GGGAGAGACTCCGTTTCAACAGTAATCAATATAGTTAGCTGCAGCGCTGGATCGTCTGGGCAG

CGATGGGTGTTTACCAATGAAGGGGCCATTTTGAATTTAAAGAATGGGTTGGCCATGGATGTG

GCGCAAGCAAATCCAAAGCTCCGCCGAATAATTATCTATCCTGCCACAGGAAAACCAAATCAA

ATGTGGCTTCCCGTGCCATGA

Fig. 1b mistletoe lectin I

```
Y E R L R L R V T H Q T T G E E Y F R F I
T L L R D Y V S S G S F S N E I P L L R Q
S T I P V S D A Q R F V L V E L T N Q G G
D S I T A A I D V T N L Y V V A Y Q A G D
Q S Y F L R D A P R G A E T H L F T G T T
R S S L P F N G S Y P D L E R Y A G H R D
Q I P L G I D Q L I Q S V T A L R F P G G
S T R T Q A R S I L I L I Q M I S E A A R
F N P I L W R A R Q Y I N S G A S F L P D
V Y M L E L E T S W G Q Q S T Q V Q H S T
D G V F N N P I R L A I P P G N F V T L T
N V R D V I A S L A I M L F V C G E R P S
S S D V R Y W P L V I R P V I A D D V T C
S A S E P T V R I V G R N G M C V D V R D
D D F H D G N Q I Q L W P S K S N N D P N
Q L W T I K R D G T I R S N G S C L T T Y
G Y T A G V Y V M I F D C N T A V R E A T
I W Q I W G N G T I I N P R S N L V L A A
S S G I K G T T L T V Q T L D Y T L G Q G
W L A G N D T A P R E V T I Y G F R D L C
M E S N G G S V W V E T C V S S Q Q N Q R
W A L Y G D G S I R P K Q N Q D Q C L T C
G R D S V S T V I N I V S C S A G S S G Q
R W V F T N E G A I L N L K N G L A M D V
A Q A N P K L R R I I I Y P A T G K P N Q
M W L P V P
```

Fig. 2a mistletoe lectin A1

TACGAGAGGCTAAGACTCAGAGTTACGCATCAAACCACGGGCGAGGAATACTTCCGGTTCATC

ACGCTTCTCCGAGATTATGTCTCAAGCGGAAGCTTTTCCAATGAGATACCACTCTTGCGTCAG

TCTACGATCCCCGTCTCCGATGCGCAAAGATTTGTCTTGGTGGAGCTCACCAACCAGGGGCAG

GACTCGGTTACGGCCGCCATCGACGTTACCAATGCTTACGTCGTGGCTTACCAAGCAGGCGAC

CAATCCTACTTTTTGCGCGACGCACCACGCGGCGCGGAAACGCACCTCTTCACCGGCACCACC

CGATCCTCTCTCCCATTCAACGGAAGCTACCCTGATCTGGAGCGATACGCCGGACATAGGGAC

CAGATCCCTCTCGGTATAGACCAACTCATTCAATCCGTCACGGCGCTTCGTTTTCCGGGCGGC

AGCACGCGTACCCAAGCTCGTTCGATTTTAATCCTCATTCAGATGATCTCCGAGGCCGCCAGA

TTCAATCCCATCTTATGGAGGTACCGCCAATACATTAACAGTGGGGCGTCATTTCTGCCAGAC

GTGTACATGCTGGAGCTGGAGACGAGTTGGGGCCAACAATCCACGCAAGTCCAGCATTCAACC

GATGGCGTTTTTAATAACCCAATTCGGTTGGCTATACCCCCGGTAACTTCGTGACGTTGACC

AATGTTCGCGACGTGATCGCCAGCTTGGCGATCATGTTGTTTGTATGCGGAGAGCGGCCATCT

TCCTCT

Fig. 2b mistletoe lectin A1

```
Y E R L R L R V T H Q T T G E E Y F R F I
T L L R D Y V S S G S F S N E I P L L R Q
S T I P V S D A Q R F V L V E L T N Q G Q
D S V T A A I D V T N A Y V V A Y Q A G D
Q S Y F L R D A P R G A E T H L F T G T T
R S S L P F N G S Y P D L E R Y A G H R D
Q I P L G I D Q L I Q S V T A L R F P G G
S T R T Q A R S I L I L I Q M I S E A A R
F N P I L W R Y R Q Y I N S G A S F L P D
V Y M L E L E T S W G Q Q S T Q V Q H S T
D G V F N N P I R L A I P P G N F V T L T
N V R D V I A S L A I M L F V C G E R P S
S S
```

Fig. 3a mistletoe lectin A2

TACGAGAGGCTAAGACTCAGAGTTACGCATCAAACCACGGGCGATGAATACTTCCGGTTCAT
CACGCTTCTCCGAGATTATGTCTCAAGCGGAAGCTTTTCCAATGAGATACCACTCTTGCGTC
AGTCTACGATCCCCGTCTCCGATGCGCAAAGATTTGTCTTGGTGGAGCTCACCAACCAGGGG
CAGGACTCGATCACGGCCGCCATCGACGTTACCAATGCTTACGTCGTGGCTTACCAAGCAGG
CGACCAATCCTACTTTTTGCGCGACGCACCACGCGGCGCGGAAACGCACCTCTTCACCGGCA
CCACCCGAGATAGATCCTCTCTCCCATTCACTGGAAGCTACACCGATCTGGAGCGATACGCC
GGACATAGGGACCAGATCCCTCTCGGTATAGAGCAACTCATTCAATCCGTCTCTGCGCTTCG
TTACCCGGGCGGCAGCACGCGTGCTCAAGCTCGTTCGATTTTAATCCTCATTCAGATGATCT
CCGAGGCCGCCAGATTCAATCCCATCTTATGGAGGTACCGCCAAGATATTAACAGTGGGGAA
TCATTTCTGCCAGACATGTACATGCTGGAGCTGGAGACGAGTTGGGGCCAACAATCCACGCA
AGTCCAGCATTCAACCGATGGCGTTTTTAATAACCCATTCCGGTTGGCTATATCTACTGGTA
ACTTCGTGACGTTGTCTAATGTTCGCTCTGTGATCGCCAGCTTGGCGATCATGTTGTTTGTA
TGCGGAGAGCGGCCATCTTCCTCT

Fig. 3b mistletoe lectin A2

```
Y E R L R L R V T H Q T T G D E Y F R F I
T L L R D Y V S S G S F S N E I P L L R Q
S T I P V S D A Q R F V L V E L T N Q G Q
D S I T A A I D V T N A Y V V A Y Q A G D
Q S Y F L R D A P R G A E T H L F T G T T
R D R S S L P F T G S Y T D L E R Y A G H
R D Q I P L G I E Q L I Q S V S A L R Y P
G G S T R A Q A R S I L I L I Q M I S E A
A R F N P I L W R Y R Q D I N S G E S F L
P D M Y M L E L E T S W G Q Q S T Q V Q H
S T D G V F N N P F R L A I S T G N F V T
L S N V R S V I A S L A I M L F V C G E R
P S S S
```

Fig. 4a mistletoe lectin I  (matched)

TATGAAAGATTGAGGTTGAGGGTGACTCACCAGACTACAGGAGAAGAGTATTTTAGATTTATT
ACTTTGTTGAGGGATTACGTTAGTTCTGGTTCTTTCAGTAACGAAATTCCTTTGCTTAGACAA
TCTACTATTCCAGTTTCTGATGCTCAGCGTTTCGTTCTTGTTGAATTGACTAACCAAGGAGGT
GATAGTATTACTGCTGCTATTGATGTGACTAACCTTTATGTTGTTGCATATCAGGCTGGTGAT
CAGTCTTATTTCCTTAGGGATGCTCCTAGAGGAGCTGAGACTCATTTGTTTACTGGTACAACA
CGGAGTTCTTTGCCTTTTAACGGTTCTTATCCAGACTTGGAAAGATATGCTGGTCACAGAGAT
CAAATTCCATTGGGAATTGATCAGTTGATCCAGAGTGTTACTGCTTTGAGATTCCCAGGTGGA
TCTACTAGAACACAGGCAAGATCTATCCTTATTTTGATCCAAATGATTAGTGAAGCTGCTAGG
TTTAACCCTATTCTTTGGAGAGCAAGACAGTATATCAACTCTGGTGCTTCTTTCCTTCCTGAT
GTTTATATGCTTGAACTTGAAACTTCATGGGGACAGCAGTCTACTCAGGTTCAACACAGTACA
GACGGTGTGTTCAACAATCCTATCAGACTTGCAATTCCACCTGGAAATTTTGTTACTCTTACA
AACGTGAGAGATGTTATTGCTTCTCTTGCTATTATGCTTTTCGTTTGTGGTGAAAGACCTTCT
AGTTCTGATGTTAGATACTGGCCATTGGTTATTAGGCCTGTTATCGCTGACGATGTGACATGT
TCTGCATCTGAACCAACTGTTAGGATCGTTGGAAGAAACGGTATGTGTGTTGATGTTCGGGAC
GATGACTTTCATGACGGTAACCAAATCCAACTTTGGCCTAGTAAGTCTAATAACGACCCAAAC
CAACTTTGGACTATTAAGAGAGACGGTACAATCAGGTCTAACGGATCTTGTCTTACTACATAC
GGTTACACTGCAGGAGTTTACGTTATGATTTTTGATTGCAACACAGCAGTTAGAGAAGCTACA
ATCTGGCAAATCTGGGGTAACGGAACTATTATTAACCCTCGTTCTAACTTGGTGCTTGCTGCT
TCTAGTGGTATTAAGGGAACAACTTTGACTGTTCAGACTTTGGACTATACTCTTGGTCAAGGA
TGGTTGGCTGGAAACGACACAGCTCCTAGAGAAGTTACAATCTACGGATTTAGAGATTTGTGT
ATGGAGTCTAACGGTGGATCTGTTTGGGTTGAAACTTGTGTTTCATCTCAGCAAAATCAGACG
TGGGCACTTTATGGTGACGGAAGTATCAGACCTAAGCAGAATCAGGATCAGTGTTTGACATGC
GGTAGGGATAGTGTGTCTACTGTTATTAACATTGTGTCTTGTTCTGCAGGTAGTTCTGGACAA
AGGTGGGTTTTCACAAACGAGGGTGCTATCCTTAACTTGAAGAACGGTCTTGCTATGGATGTT
GCTCAGGCTAACCCTAAGTTGAGAAGGATTATCATTTACCCAGCTACTGGTAAGCCTAACCAG
ATGTGGTTGCCAGTTCCTTAT

Fig. 4b mistletoe lectin I (matched)

```
Y E R L R L R V T H Q T T G E E Y F R F I
T L L R D Y V S S G S F S N E I P L L R Q
S T I P V S D A Q R F V L E L T N Q G G
D S I T A A I D V T N L Y V V A Y Q A G D
Q S Y F L R D A P R G A E T H L F T G T T
R S S L P F N G S Y P D L E R Y A G H R D
Q I P L G I D Q L I Q S V T A L R F P G G
S T R T Q A R S I L I L I Q M I S E A A R
F N P I L W R A R Q Y I N S G A S F L P D
V Y M L E L E T S W G Q Q S T Q V Q H S T
D G V F N N P I R L A I P P G N F V T L T
N V R D V I A S L A I M L F V C G E R P S
S S D V R Y W P L V I R P V I A D D V T C
S A S E P T V R I V G R N G M C V D V R D
D D F H D G N Q I Q L W P S K S N N D P N
Q L W T I K R D G T I R S N G S C L T T Y
G Y T A G V Y V M I F D C N T A V R E A T
I W Q I W G N G T I I N P R S N L V L A A
S S G I K G T T L T V Q T L D Y T L G Q G
W L A G N D T A P R E V T I Y G F R D L C
M E S N G G S V W V E T C V S S Q Q N Q R
W A L Y G D G S I R P K Q N Q D Q C L T C
G R D S V S T V I N I V S C S A G S S G Q
R W V F T N E G A I L N L K N G L A M D V
A Q A N P K L R R I I I Y P A T G K P N Q
M W L P V P
```

Fig. 5a mistletoe lectin A1 (matched)

```
TATGAAAGATTGAGGTTGAGGGTGACTCACCAGACTACAGGAGAAGAGTATTTTAGATTTATT
ACTTTGTTGAGGGATTACGTTAGTTCTGGTTCTTTCAGTAACGAAATTCCTTTGCTTAGACAA
TCTACTATTCCAGTTTCTGATGCTCAGCGTTTCGTTCTTGTTGAATTGACTAACCAAGGACAG
GATAGTGTTACTGCTGCTATTGATGTGACTAACGCTTATGTTGTTGCATATCAGGCTGGTGAT
CAGTCTTATTTCCTTAGGGATGCTCCTAGAGGAGCTGAGACTCATTTGTTTACTGGTACAACA
CGGAGTTCTTTGCCTTTTAACGGTTCTTATCCAGACTTGGAAAGATATGCTGGTCACAGAGAT
CAAATTCCATTGGGAATTGATCAGTTGATCCAGAGTGTTACTGCTTTGAGATTCCCAGGTGGA
TCTACTAGAACACAGGCAAGATCTATCCTTATTTTGATCCAAATGATTAGTGAAGCTGCTAGG
TTTAACCCTATTCTTTGGAGATACAGACAGTATATCAACTCTGGTGCTTCTTTCCTTCCTGAT
GTTTATATGCTTGAACTTGAAACTTCATGGGACAGCAGTCTACTCAGGTTCAACACAGTACA
GACGGTGTGTTCAACAATCCTATCAGACTTGCAATTCCACCTGGAAATTTTGTTACTCTTACA
AACGTGAGAGATGTTATTGCTTCTCTTGCTATTATGCTTTTCGTTTGTGGTGAAAGACCTTCT
AGTTCT
```

Fig. 5b mistletoe lectin A1 (matched)

```
Y E R L R L R V T H Q T T G E E Y F R F I
T L L R D Y V S S G S F S N E I P L L R Q
S T I P V S D A Q R F V L V E L T N Q G Q
D S V T A A I D V T N A Y V V A Y Q A G D
Q S Y F L R D A P R G A E T H L F T G T T
R S S L P F N G S Y P D L E R Y A G H R D
Q I P L G I D Q L I Q S V T A L R F P G G
S T R T Q A R S I L I L I Q M I S E A A R
F N P I L W R Y R Q Y I N S G A S F L P D
V Y M L E L E T S W G Q Q S T Q V Q H S T
D G V F N N P I R L A I P P G N F V T L T
N V R D V I A S L A I M L F V C G E R P S
S S
```

Fig. 6a mistletoe lectin A2 (matched)

TATGAAAGATTGAGGTTGAGGGTGACTCAC

Fig. 6b mistletoe lectin A2 (matched)

```
Y E R L R L R V T H Q T T G D E Y F R F I
T L L R D Y V S S G S F S N E I P L L R Q
S T I P V S D A Q R F V L V E L T N

Fig. 7a mistletoe lectin B

GATGATGTTACCTGCAGTGCTTCGGAACCTACGGTGCGGATTGTGGGTCGAAATGGCATGTGC
GTGGACGTCCGAGATGACGATTTCCACGATGGGAATCAGATACAGTTGTGGCCCTCCAAGTCC
AACAATGATCCGAATCAGTTGTGGACGATCAAAAGGGATGGAACCATTCGATCCAATGGCAGC
TGCTTGACCACGTATGGCTATACTGCTGGCGTCTATGTGATGATCTTCGACTGTAATACTGCT
GTGCGGGAGGCCACTATTTGGCAGATATGGGGCAATGGGACCATCATCAATCCAAGATCCAAT
CTGGTTTTGGCAGCATCATCTGGAATCAAAGGCACTACGCTTACGGTGCAAACACTGGATTAC
ACGTTGGGACAGGGCTGGCTTGCCGGTAATGATACCGCCCCACGCGAGGTGACCATATATGGT
TTCAGGGACCTTTGCATGGAATCAAATGGAGGGAGTGTGTGGGTGGAGACGTGCGTGAGTAGC
CAACAGAACCAAAGATGGGCTTTGTACGGGGATGGTTCTATACGCCCCAAACAAAACCAAGAC
CAATGCCTCACCTGTGGGAGAGACTCCGTTTCAACAGTAATCAATATAGTTAGCTGCAGCGCT
GGATCGTCTGGGCAGCGATGGGTGTTTACCAATGAAGGGGCCATTTTGAATTTAAAGAATGGG
TTGGCCATGGATGTGGCGCAAGCAAATCCAAAGCTCCGCCGAATAATTATCTATCCTGCCACA
GGAAAACCAAATCAAATGTGGCTTCCCGTGCCATGA

Fig. 7b mistel lectin 3

```
D D V T C S A S E P T V R I V G R N G M C
V D V R D D D F H D G N Q I Q L W P S K S
N N D P N Q L W T I K R D G T I R S N G S
C L T T Y G Y T A G V Y V M I F D C N T A
V R E A T I W Q I W G N G T I I N P R S N
L V L A A S S G I K G T T L T V Q T L D Y
T L G Q G W L A G N D T A P R E V T I Y G
F R D L C M E S N G G S V W V E T C V S S
Q Q N Q R W A L Y G D G S I R P K Q N Q D
Q C L T C G R D S V S T V I N I V S C S A
G S S G Q R W V F T N E G A I L N L K N G
L A M D V A Q A N P K L R R I I I Y P A T
G K P N Q M W L P V P

Fig. 8a mistletoe lectin B1

GATGATGTTACCTGCAGTGCTTCGGAACCTACGGTGCGGATTGTGGGTCGAAATGGCATGCGC
GTGGACGTCCGAGATGACGATTTCCACGATGGGAATCAGATACAGTTGTGGCCCTCCAAGTCC
AACAATGATCCGAATCAGTTGTGGACGATCAAAAGGGATGGAACCATTCGATCCAATGGCAGC
TGCTTGACCACGTATGGCTATACTGCTGGCGTCTATGTGATGATCTTCGACTGTAATACTGCT
GTGCGGGAGGCCACTATTTGGCAGATATGGGACAATGGACCATCATCAATCCAAGATCCAAT
CTGGTTTTGGCAGCATCATCTGGAATCAAAGGCACTACGCTTACGGTGCAAACACTGGATTAC
ACGTTGGGACAGGGCTGGCTTGCCGGTAATGATACCGCCCCACGCGAGGTGACCATATATGGT
TTCAGGGACCTTTGCATGGAATCAAATGGAGGGAGTGTGTGGGTGGAGACGTGCGACAGTAGC
CAAAAGAACCAAGGCAAATGGGCTTTGTACGGGGATGGTTCTATACGCCCCAAACAAAACCAA
GACCAATGCCTCACCTCTGGGAGAGACTCCGTTTCAACAGTAATCAATATAGTTAGCTGCAGC
GGAGCTTCGGGGTCTCAGCGATGGGTGTTTACCAATGAAGGGGCCATTTTGAATTTAAAGAAT
GGGTTGGCCATGGATGTGGCGCAAGCAAATCCAAAGCTCCGCCGAATAATTATCTATCCTGCC
ACAGGAAAACCAAATCAAATGTGGCTTCCCGTGTTCTGA

Fig. 8b mistletoe lectin B1

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N G G S V W V E T C D S

Fig. 9a mistletoe lectin B2

GATGATGTTACCTGCAGTGCTTCGGAACCTACGGTGCGGATTGTGGGTCGAAGTGGCATGCGC
GTGGACGTCCGAGATGACGATTTCCACGATGGGAATCAGATACAGTTGTGGCCCTCCAAGTCC
AACAATGATCCGAATCAGTTGTGGACGATCAAAAGGGATAACACCATTCGATCCAATGGCAGC
TGCTTGACCACGTATGGCTATACTGCTGGCGTCTATGTGATGATCTTCGACTGTAATACTGCT
GTGCGGGAGGCCACTATTTGGCAGATATGGGACAATGGGACCATCATCAATCCAAGATCCAAT
CTGGTTTTGGCAGCATCATCTGGAATCAAAGGCACTACGCTTACGGTGCAAACACTGGATTAC
ACGTTGGGACAGGGCTGGCTTGCCGGTAATGATACCGCCCCACGCGAGGTGACCATATATGGT
TTCAGGGACCTTTGCATGGAATCAAATCAAGGGAGTGTGTGGGTGGAGACGTGCGACAGTAGC
CAAAAGAACCAAGGCAAATGGGCTTTGTACGGGGATGGTTCTATACGCCCCAAACAAAACCAA
GACCAATGCCTCACCGTTGGGAGAGACTCCGTTTCAACAGTAATCAATATAGTTAGCTGCAGC
GGAGCTTCGGGGTCTCAGCGATGGGTGTTTACCAATGAATACGCCATTTTGAATTTAAAGAGT
GGGTTGGCCATGGATGTGGCGCAAGCAAATCCAAAGCTCCGCCGAATAATTATCTATCCTGCC
ACAGGAAAACCAAATCAAATGTGGCTTCCCGTGTTCTGA

Fig. 9b mistletoe lectin B2

```
D D V T C S A S E P T V R I V G R S G M R
V D V R D D D F H D G N Q I Q L W P S K S
N N D P N Q L W T I K R D N T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N Q G S V W V E T C D S S
Q K N Q G K W A L Y G D G S I R P K Q N Q
D Q C L T V G R D S V S T V I N I V S C S
G A S G S Q R W V F T N E Y A I L N L K S
G L A M D V A Q A N P K L R R I I I Y P A
T G K P N Q M W L P V F
```

Fig. 10a mistletoe lectin B3

GATGATGTTACCTGCAGTGCTTCGGAACC

Fig. 10b mistletoe lectin B3

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N G G S V W V E T C D S S
Q K N Q G K W A L Y G D G S I R P K Q N Q
D Q C L T S G R D S V S T V I N I V S C S
G A S G S Q R W V F T N E G A I L N L K T
G L A M D V A Q A N P K L R R I I Y P A
T G K P N Q M W L P V F
```

Fig.11a mistletoe lectin B4

GATGATGTTACCTGCAGTGCTTCGGAACCTACGGTGCGGATTGTGGGTCGAAATGGCATGCGC

GTGGACGTCCGAGATGACGATTTCCACGATGGGAATCAGATACAGTTGTGGCCCTCCAAGTCC

AACAATGATCCGAATCAGTTGTGGACGATCAAAAGGGATGGAACCATTCGATCCAATGGCAGC

TGCTTGACCACGTATGGCTATACTGCTGGCGTCTATGTGATGATCTTCGACTGTAATACTGCT

GTGCGGGAGGCCACTATTTGGCAGATATGGGACAATGGGACCATCATCAATCCAAGATCCAAT

CTGGTTTTGGCAGCATCATCTGGAATCAAAGGCACTACGCTTACGGTGCAAACACTGGATTAC

ACGTTGGGACAGGGCTGGCTTGCCGGTAATGATACCGCCCACGCGAGGTGACCATATATGGT

TTCAGGGACCTTTGCATGGAATCAAATGGAGGGAGTGTGTGGGTGGAGACGTGCGACAGTAGC

CAAAAGAACCAAGGCAAATGGGCTTTGTACGGGGATGGTTCTATACGCCCAAACAAAACCAA

GACCAATGCCTCACCTCTGGGAGAGACTCCGTTTCAACAGTAATCAATATAGTTAGCTGCAGC

GGAGCTTCGGGGTCTCAGCGATGGGTGTTTACCAATGAAGGGGCCATTTTGAATTTAAAGAAA

GGGCCGGCCATGGATGTGGCGCAAGCAAATCCAAAGCTCCGCCGAATAATTATCTATCCTGCC

ACAGGAAAACCAAATCAAATGTGGCTTCCCGTGTTCTGA

Fig. 11b mistletoe lectin B4

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N G G S V W V E T C D S S
Q K N Q G K W A L Y G D G S I R P K Q N Q
D Q C L T S G R D S V S T V I N I V S C S
G A S G S Q R W V F T N E G A I L N L K K
G P A M D V A Q A N P K L R R I I I Y P A
T G K P N Q M W L P V F
```

Fig. 12a mistletoe lectin B5

```
GATGATGTTACCTGCAGTGCTTCGGAACCTACGGTGCGGATTGTGGGTCGAAATGGCATGCGC
GTGGACGTCCGAGATGACGATTTCCACGATGGGAATCAGATACAGTTGTGGCCCTCCAAGTCC
AACAATGATCCGAATCAGTTGTGGACGATCAAAAGGGATGGAACCATTCGATCCAATGGCAGC
TGCTTGACCACGTATGGCTATACTGCTGGCGTCTATGTGATGATCTTCGACTGTAATACTGCT
GTGCGGGAGGCCACTATTTGGCAGATATGGGACAATGGGACCATCATCAATCCAAGATCCAAT
CTGGTTTTGGCAGCATCATCTGGAATCAAAGGCACTACGCTTACGGTGCAAACACTGGATTAC
ACGTTGGGACAGGGCTGGCTTGCCGGTAATGATACCGCCCCACGCGAGGTGACCATATATGGT
TTCAGGGACCTTTGCATGGAATCAAATGGAGGGAGTGTGTGGGTGGAGACGTGCGACAGTAGC
CAAAAGAACCAAGGCAAATGGGCTTTGTACGGGGATGGTTCTATACGCCCCAAACAAAACCAA
GACCAATGCCTCACCTCTGGGAGAGACTCCGTTTCAACAGTAATCAATATAGTTAGCTGCAGC
GGAGCTTCGGGGTCTCAGCGATGGGTGTTTACCAATGAAGGGGCCATTTTGAATTTAAAGAAT
AGCTTGATGGTGGATGTGGCGCAAGCAAATCCAAAGCTCCGCCGAATAATTATCTATCCTGCC
ACAGGAAAACCAAATCAAATGTGGCTTCCCGTGTTCTGA
```

Fig. 12b mistletoe lectin B5

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N G G S V W V E T C D S S
Q K N Q G K W A L Y G D G S I R P K Q N Q
D Q C L T S G R D S V S T V I N I V S C S
G A S G S Q R W V F T N E G A I L N L K N
S L M V D V A Q A N P K L R R I I I Y P A
T G K P N Q M W L P V F
```

Fig. 13a mistletoe lectin B (matched)

GACGATGTGACATGTTCTGCATCTGAACCAACTGTTAGGATCGTTGGAAGAAACGGTATGTGT

GTTGATGTTCGGGACGATGACTTTCATGACGGTAACCAAATCCAACTTTGGCCTAGTAAGTCT

AATAACGACCCAAACCAACTTTGGACTATTAAGAGAGACGGTACAATCAGGTCTAACGGATCT

TGTCTTACTACATACGGTTACACTGCAGGAGTTTACGTTATGATTTTTGATTGCAACACAGCA

GTTAGAGAAGCTACAATCTGGCAAATCTGGGGTAACGGAACTATTATTAACCCTCGTTCTAAC

TTGGTGCTTGCTGCTTCTAGTGGTATTAAGGGAACAACTTTGACTGTTCAGACTTTGGACTAT

ACTCTTGGTCAAGGATGGTTGGCTGGAAACGACACAGCTCCTAGAGAAGTTACAATCTACGGA

TTTAGAGATTTGTGTATGGAGTCTAACGGTGGATCTGTTTGGGTTGAAACTTGTGTTTCATCT

CAGCAAAATCAGAGGTGGGCACTTTATGGTGACGGAAGTATCAGACCTAAGCAGAATCAGGAT

CAGTGTTTGACATGCGGTAGGGATAGTGTGTCTACTGTTATTAACATTGTGTCTTGTTCTGCA

GGTAGTTCTGGACAAAGGTGGGTTTTCACAAACGAGGGTGCTATCCTTAACTTGAAGAACGGT

CTTGCTATGGATGTTGCTCAGGCTAACCCTAAGTTGAGAAGGATTATCATTTACCCAGCTACT

GGTAAGCCTAACCAGATGTGGTTGCCAGTTCCTTAT

Fig. 13b mistletoe lectin B (matched)

```
D D V T C S A S E P T V R I V G R N G M C
V D V R D D D F H D G N Q I Q L W P S K S
N N D P N Q L W T I K R D G T I R S N G S
C L T T Y G Y T A G V Y V M I F D C N T A
V R E A T I W Q I W G N G T I I N P R S N
L V L A A S S G I K G T T L T V Q T L D Y
T L G Q G W L A G N D T A P R E V T I Y G
F R D L C M E S N G G S V W V E T C V S S
Q Q N Q R W A L Y G D G S I R P K Q N Q D
Q C L T C G R D S V S T V I N I V S C S A
G S S G Q R W V F T N E G A I L N L K N G
L A M D V A Q A N P K L R R I I I Y P A T
G K P N Q M W L P V P
```

Fig. 14a mistletoe lectin (matched)

```
GACGATGTGACATGTTCTGCATCTGAACCAACTGTTAGGATCGTTGGAAGAAACGGTATGCGT
GTTGATGTTCGGGACGATGACTTTCATGACGGTAACCAAATCCAACTTTGGCCTAGTAAGTCT
AATAACGACCCAAACCAACTTTGGACTATTAAGAGAGACGGTACAATCAGGTCTAACGGATCT
TGTCTTACTACATACGGTTACACTGCAGGAGTTTACGTTATGATTTTTGATTGCAACACAGCA
GTTAGAGAAGCTACAATCTGGCAAATCTGGGATAACGGAACTATTATTAACCCTCGTTCTAAC
TTGGTGCTTGCTGCTTCTAGTGGTATTAAGGGAACAACTTTGACTGTTCAGACTTTGGACTAT
ACTCTTGGTCAAGGATGGTTGGCTGGAAACGACACAGCTCCTAGAGAAGTTACAATCTACGGA
TTTAGAGATTTGTGTATGGAGTCTAACGGTGGATCTGTTTGGGTTGAAACTTGTGATTCATCT
CAGAAAAATCAGGGCAAGTGGGCACTTTATGGTGACGGAAGTATCAGACCTAAGCAGAATCAG
GATCAGTGTTTGACATCCGGTAGGGATAGTGTGTCTACTGTTATTAACATTGTGTCTTGTTCT
GGAGCTAGTGGATCTCAAAGGTGGGTTTTCACAAACGAGGGTGCTATCCTTAACTTGAAGAAC
GGTCTTGCTATGCATGTTGCTCAGGCTAACCCTAAGTTGAGAAGGATTATCATTTACCCAGCT
ACTGGTAAGCCTAACCAGATGTGGTTGCCAGTTTTTTAT
```

Fig.14b mistletoe lectin 1 (matched)

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N G G S V W V E T C D S S
Q K N Q G K W A L Y G D G S I R P K Q N Q
D Q C L T S G R D S V S T V I N I V S C S
G A S G S Q R W V F T N E G A I L N L K N
G L A M D V A Q A N P K L R R I I I

Fig. 15a mistletoe lectin B2 (matched)

GACGATGTGACATGTTC

Fig. 15b mistletoe lectin B2 (matched)

```
D D V T C S A

Fig.16a mistletoe lectin B3 (matched)

GACGATGTGACATGTTCTGCATCTGAACCAACTGTTAGGATCGTTGGAAGAAACGGTATGCGT
GTTGATGTTCGGGACGATGACTTTCATGACGGTAACCAAATCCAACTTTGGCCTAGTAAGTCT
AATAACGACCCAAACCAACTTTGGACTATTAAGAGAGACGGTACAATCAGGTCTAACGGATCT
TGTCTTACTACATACGGTTACACTGCAGGAGTTTACGTTATGATTTTTGATTGCAACACAGCA
GTTAGAGAAGCTACAATCTGGCAAATCTGGGATAACGGAACTATTATTAACCCTCGTTCTAAC
TTGGTGCTTGCTGCTTCTAGTGGTATTAAGGGAACAACTTTGACTGTTCAGACTTTGGACTAT
ACTCTTGGTCAAGGATGGTTGGCTGGAAACGACACAGCTCCTAGAGAAGTTACAATCTACGGA
TTTAGAGATTTGTGTATGGAGTCTAACGGTGGATCTGTTTGGGTTGAAACTTGTGATTCATCT
CAGAAAA

Fig.16b mistletoe lectin B3 (matched)

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N G G S V W V E T C D S S
Q K N Q G K W A L Y G D G S I R P K Q N Q
D Q C L T S G R D S V S T V I N I V S C S
G A S G S Q R W V F T N E G A I L N L K T
G L A M D V A Q A N P K L R R I I I Y P A
T G K P N Q M W L P V F
```

Fig. 17a mistletoe lectin B4 (matched)

GACGATGTGACATGTTCTGCATCTGAACCAACTGTTAGGATCGTTGGAAGAAACGGTATGCGT

GTTGATGTTCGGGACGATGACTTTCATGACGGTAACCAAATCCAACTTTGGCCTAGTAAGTCT

AATAACGACCCAAACCAACTTTGGACTATTAAGAGAGACGGTACAATCAGGTCTAACGGATCT

TGTCTTACTACATACGGTTACACTGCAGGAGTTTACGTTATGATTTTTGATTGCAACACAGCA

GTTAGAGAAGCTACAATCTGGCAAATCTGGGATAACGGAACTATTATTAACCCTCGTTCTAAC

TTGGTGCTTGCTGCTTCTAGTGGTATTAAGGGAACAACTTTGACTGTTCAGACTTTGGACTAT

ACTCTTGGTCAAGGATGGTTGGCTGGAAACGACACAGCTCCTAGAGAAGTTACAATCTACGGA

TTTAGAGATTTGTGTATGGAGTCTAACGGTGGATCTGTTTGGGTTGAAACTTGTGATTCATCT

CAGAAAAATCAGGGCAAGTGGGCACTTTATGGTGACGGAAGTATCAGACCTAAGCAGAATCAG

GATCAGTGTTTGACATCCGGTAGGGATAGTGTGTCTACTGTTATTAACATTGTGTCTTGTTCT

GGAGCTAGTGGATCTCAAAGGTGGGTTTTCACAAACGAGGGTGCTATCCTTAACTTGAAGAAA

GGTCCTGCTATGGATGTTGCTCAGGCTAACCCTAAGTTGAGAAGGATTATCATTTACCCAGCT

ACTGGTAAGCCTAACCAGATGTGGTTGCCAGTTTTTTAT

Fig. 17b mistletoe lectin B4 (matched)

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I I N P R S N
L V L A A S S G I K G T T L T V Q T L D Y
T L G Q G W L A G N D T A P R E V T I Y G
F R D L C M E S N G G S V W V E T C D S S
Q K N Q G K W A L Y G D G S I R P K Q N Q
D Q C L T S G R D S V S T V I N I V S C S
G A S G S Q R W V F T N E G A I L N L K K
G P A M D V A Q A N P K L R R I I Y P A
T G K P N Q M W L P V F
```

Fig. 18a mistletoe lectin B5 (matched)

```
GACGATGTGACATGTTCTGCATCTGAACCAAC

Fig.18b mistletoe lectin B5 (matched)

```
D D V T C S A S E P T V R I V G R N G M R
V D V R D D D F H D G N Q I Q L W P S K S
N N D P N Q L W T I K R D G T I R S N G S
C L T T Y G Y T A G V Y V M I F D C N T A
V R E A T I W Q I W D N G T I N P R S N
L V L A A S S G I K G T T L T V Q T L D Y
T L G Q G W L A G N D T A P R E V T I Y G
F R D L C M E S N G G S V W V E T C D S S
Q K N Q G K W A L Y G D G S I R P K Q N Q
D Q C L T S G R D S V S T V I N I V S C S
G A S G S Q R W V F T N E G A I L N L K N
S L M V D V A Q A N P K L R R I I Y P A
T G K P N Q M W L P V F
```

RECOMBINANT MISTLETOE LECTINES

The present invention relates to processes for the production of mistletoe lectin polypeptides in homologous and heterologous host systems and mistletoe lectin peptides as such. Further, nucleic acid molecules are provided, which code for these mistletoe lectin polypeptides, and also pharmaceutical compositions which contain these mistletoe lectin polypeptides or mistletoe lectin nucleic acids.

Mistletoe (*Viscum album*) has been known from antiquity as a healing plant. The semishrub plant lives as a semiparasite on the branches of woody plants and is particularly widespread in Europe, North Australia, Asia and in tropical and subtropical Africa. At the start of this century, the cyto- and tumour-toxic action of mistletoe extract, which has since then been specifically used for cancer therapy, was recognised. For this, the extract is used both as a single therapeutic agent and also in combination with chemo- or radiation therapy. Mistletoe preparations are particularly often used for example as a prophylactic against relapse after surgical tumour removal.

Systematic studies of the mode of action show that, after injection, aqueous mistletoe extract as well as its cytotoxic action also has an immunomodulatory effect, and apart from this shows generally mood-brightening effects. After injection of mistletoe extract, a significant increase in the cell numbers of certain lymphocyte subpopulations (inter alia T helper lymphocytes, natural killer (NK) cells and macrophages) and phagocytosis activity in granulo- and monocytes, which are directly involved in tumour defence, are observed (Hajto T, Hostanska K, Gabius H-J, (1990), Therapeutikum 4, 135–145; Beuth J, Ko H L, Tunggal L, Gabius H-J, Steuer M, Uhlenbruck G, Pulverer G (1993), Med. Welt 44, 217–220; Beuth J, Ko H L, Tunggal L, Geisel J, Pulverer G (1993), Arzneim.-Forsch/Drug Res. 43 (1), 166–169; Beuth J, Ko H L, Gabius H-J, Burricheter H, Oette Kl, Pulverer G (1992), Clin. Investing, 70, 658–661). Further, a significant increase in defined acute phase proteins in the serum, which is mediated by the cytokines IL-1, IL-6 and TNF-α, can be detected (Hajto T, Hostanska K, Frei K, Rordorf C, Gabius H-J (1990), Cancer Res. 50, 3322–3326; Beuth J, Ko H-L, Gabius H-J, Pulverer G (1991), In Vivo 5, 29–32; Beuth J, Ko H-L, Tunggal L, Jeljaszewicz J, Steuer M K, Pulverer G (1994), In Vivo 8, 989–992; Beuth J, Ko H-L, Tunggal L, Jeljaszewicz J, Steuer M K, Pulverer G (1994), Dtsch. Zschr. Onkol. 26, 1–6; Beuth J, Ko H-L, Tunggal L, Steuer M K, Geisel J, Jeljaszewicz J, Pulverer G (1993), In Vivo 7, 407–410, Kayser K, Gabius S, Gabius H-J, Hagemeyer O (1992) Tumordiag. und Ther. 13, 190–195). As well as the prolongation of the survival time of cancer patients achievable by mistletoe extract treatment, an increase in the patients' quality of life is also observed, which is attributed to the rise in β-endorphins in the blood (Heiny B-M, Beuth J (1994), Anticancer Res. 14, 1339–1342; Heiny B-M, Beuth J (1994), Dtsch. Zschr. Onkol. 26, 103–108). As endogenous opioids, β-endorphins improve the general well-being, in that they for example have a pain-relieving action, and improve the pain index (Falconer J, Chan E C, Madsens G (1988), J. Endocrinol. 118, 5–8).

Analysis of the active substances of mistletoe extract has shown that the immunostimulating effect is attributable to a certain group of glycoproteins, the mistletoe lectins. Hitherto, three mistletoe-specific lectins with different molecular weights and sugar-binding specificities had been identified. The concentration of mistletoe lectin I (ML-I) in the aqueous plant extract is markedly higher than that of mistletoe lectin II (ML-II) and mistletoe lectin III (ML-III). It could be shown that the immunostimulating effect of the mistletoe extract is attributable to the presence of ML-I: if the ML-I lectin is removed from the mistletoe extract, the extract loses its immunostimulating action (Beuth J, Stoffel B, Ko H-L, Jeljaszewicz J, Pulverer G (1995), Arzneim.-Forsch./Drug. Res. 45 (II), 1240–1242). The β-galactoside-specific ML-I lectin consists of two A- and two B-chains (MLA and MLB), each glycosylated, whose molecular weights are about 29 kDa and 34 kDa respectively. The amino acid sequence of MLA contains one potential glycosylation site, while MLB contains three glycosylation sites in the N-terminal region of the amino acid sequence. The two chains are linked together via a disulphide bridge (FIG. A; Ziska P, Franz H, Kindt A (1978), Experientia 34, 123–124). The resulting mistletoe lectin monomers can associate into dimers with the formation of non-covalent bonds.

Studies of the sedimentation behaviour of ML-I during analytical centrifugation show that in vivo ML-I is present in a monomer-dimer equilibrium (Luther P, Theise H. Chatterjee B, Kardruck D, Uhlenbruck G (1980), Int. J. Biochem. 11, 429–435). The MLB-chain is able to bind to galactose-containing structures on the surface of cell membranes (e.g. receptor molecules) and thereby to trigger cytokine release. Through endocytosis, ML-I dimers and monomers get into the cell, where the protein complexes break down into MLA and MLB chains through reduction of the disulphide bridge bonds. The MLA chains are thereupon able to bind to the ribosomal 28 S subunit and to inactivate this.

The study of ML-I monomers using 2-D gel electrophoresis yielded 25 different isoforms, which are attributable to different combinations of various A and B chains and different glycosylation states of the chains (Schink et al., 1992, Naturwissenschaften 79, 80–81). It is suspected that the individual isoforms fulfil specific functions and each of these isoforms contributes to the anti-tumorigenic effect of the mistletoe extract.

By now, a nucleic acid sequence and the amino acid sequence derived therefrom of one ML-I lectin is already known from European Patent Application EP 0 751 211 A1. However this one polypeptide is not capable of satisfactorily emulating the action of the many ML-I isoenzymes contained in natural mistletoe extract as regards the anti-tumorigenic and mood-brightening effect.

Hence the technical problem of the present invention is to provide a process which makes it possible to produce mistletoe lectins in sufficient quantities and at the same time to imitate the diversity in ML-I isoenzymes of the natural mistletoe extract.

The problem is solved according to the invention by the provision the a process indicated above.

The present invention moreover makes available 2 new polypeptides of the MLA chain and 6 new polypeptides of the MLB chain of ML-I, which can be expressed individually or in combination in a suitable host system. Thereby, "homologous" and "heterologous" ML-I dimers are formed, where the term "homologous" denotes a dimer which consists either of two MLA and two MLB chains, each the same and the term "heterologous" denotes a dimer which consists of two different MLA and/or two different MLB chains. The diversity of the MLA and MLB chains makes it possible to create a multitude of different MLA/MLB complexes, the therapeutic action of which is modelled on the above-described action of the lectin mixture which was detected in aqueous mistletoe extract. One of the advantages which the present invention offers compared to the conventional extraction of mistletoe extracts from fresh plants is that the immunomodulating components of the mistletoe extract can be produced by a biotechnological process. This means that sufficient quantities of mistletoe lectin I can be produced independently of plant material, which is only available to a limited extent and can only be harvested at a certain time of year. Furthermore, a mixture of mistletoe lectins biotechnologically produced in this way contains none of the "impurities" occurring in the natural mistletoe extract, e.g. viscotoxins.

Further, owing to the fact that the present invention makes a large number of different MLA and MLB polypeptides of ML-I available, it becomes possible to "design" pharmacological compositions in a target-oriented manner. This means that e.g. by the selection of certain MLB polypeptides which define the binding affinity of the MLA/MLB complex to the target cells, the immunomodulatory action of a composition can be influenced. Furthermore, by the use of defined MLA polypeptides, the cytotoxicity of a composition can be varied.

In order to be able biotechnologically to produce the mixture of mistletoe lectins contained in mistletoe extracts, firstly the amino acid sequence of a pharmaceutically interesting mistletoe lectin was elucidated. For this, a mistletoe extract was obtained from *Viscum album L.* ssp. *platyspermum* Kell, which were harvested from poplars, and mistletoe lectin I was partially purified by affinity chromatography (Example 1). The subsequent analysis by sodiumdodecyl sulphate-polyacrylamide gel electrophoresis (SDS-PAGE), high performance liquid chromatography (HPLC) and sequence analysis by Edman degradation showed 2 MLA isoforms and 6 MLB isoforms.

Degenerate oligonucleotides were divided from short regions of the amino acid sequences, and by means of these the genomic mistletoe lectin I DNA sequence was determined using the polymerase chain reaction (PCR) process. Surprisingly, in spite of the many identified ML-I amino acid sequences, only a single nucleic acid sequence more less corresponding to these sequences was identified. By Southern blot analysis, it was confirmed that the ML-I gene occurs in only one copy per genome. Hence, the sequence variability of the MLA and MLB polypeptides is to be explained only by the occurrence of RNA editing or other posttranscriptional or posttranslational modifications in mistletoe cells.

All processes that lead to differences between the final mRNA sequence and the corresponding "template" DNA, except for "RNA-splicing" and tRNA modifications, are described as "RNA-editing". "mRNA-splicing", and also the occurrence of modified tRNAs, is generally known and is therefore not explained in more detail here. In "RNA-editing", individual nucleotides or strands of up to several hundred nucleotides in length are exchanged, inserted or deleted co- or posttranscriptionally, which can lead to reading-frame changes in the coded sequence. The first example of RNA-editing was discovered in studies of the coxII transcript of the mitochondrial DNA of trypansomes (Benne R et al (1986) Cell 46, 819–826). Further, this process has been detected in mitochondria and chloroplasts of higher plants and singular nuclear transcripts in mammalian cells. The precise mechanism of RNA editing, like the mechanisms for posttranslational modifications of the primary amino acid sequence have however so far only been very incompletely described in the literature.

Since however this process has so far only been detected in very few plants and the aim is to make biotechnological production of the various mistletoe lectin I polypeptides also possible in other plant cells than mistletoe cells as far as possible independently of posttranscriptional or posttranslational changes, the genomic DNA was matched to the sequence of the various isolated polypeptides by deliberate mutations. Furthermore, the genomic sequence was matched to the preferred codon utilisation of *Brassica*, in order to make optimal expression possible e.g. in rape cells.

Hence the present invention makes available a process for the production of a mistletoe lectin polypeptide or a fragment thereof in the heterologous system having the following sequence (SEQ ID NO: 1 and 40):

Y E R L R L R V T H Q T T G X1 E Y F R F I T L

L R D Y V S S G S F S N E I P L L R Q S T I P

V S D A Q R F V L V E L T N Q G X2 D S X3 T A A

I D V T N X4 Y V V A Y Q A G D Q S Y F L R D A

P R G A E T H L F T G T T R X5 S S L P F X6 G S

Y X7 D L E R Y A G H R D Q I P L G I X8 Q L I Q

S V X9 A L R X10 P G G S T R X11 Q A R S I L I L

I Q M I S E A A R F N P I L W R X12 R Q X13 I N

S G X14 S F L P D X15 Y M L E L E T S W G Q Q S

T Q V Q H S T D G V F N N P X16 R L A I X17 X18 G

N F V T L X19 N V R X20 V I A S L A I M L F V C

G E R P S S S D V R Y W P L V I R P V I A D D

V T C S A S E P T V R I V G R X21 G M X22 V D V

R D D D F H D G N Q I Q L W P S K S N N D P N

Q L W T I K R D X23 T I R S N G S C L T T Y G Y

T A G V Y V M I F D C N T A V R E A T I W Q I

W X24 N G T I I N P R S N L V L A A S S G I K G

T T L T V Q T L D Y T L G Q G W L A G N D T A

P R E V T I Y G F R D L C M Z S N X25 G S V M V

E T C X26 S S Q X27 N Q X28 X29 W A L Y G D G S I R

P K Q N Q D Q C L T X30 G R D S V S T V I N I V

S C S X31 X32 S X33 X34 Q R W V F T N E X35 A I L N

L K X36 X37 X38 X39 X40 D V A Q A N P K L R R I I

Y P A T G K P N Q M W L P V X41 including the step of expressing of a eukaryotic or prokaryotic vector, into which a nucleic acid coding for the mistletoe lectin polypeptide according to the usual genetic code or a fragment thereof is cloned, in a suitable heterologous eukaryotic or prokaryotic host, wherein X1 is D or E, X2 is G or Q, X3 is I or V, X4 is L or A, X5 is DR or missing, X6 is N or T, X7 is P or T, X8 is D or E, X9 is S or T, X10 is F or Y, X11 is T or A, X12 is A or Y, X13 is Y or D, X14 is A or E, X15 is V or M, X16 is I or F, X17 is P or S, X18 is P or T, X19 is T or S, X20 is D or S, X21 is N or S, X22 is C or R, X23 is G or N, X24 is G or D, X25 is G or Q, X26 is V or D, X27 is Q or K, X28 is G or missing, X29 is R or K, X30 is C or S or V, X31 is A or G, X32 is G or A, X33 is S or G, X34 is G or S, X35 is G or Y, X36 is N or S or T or K, X37 is S or G, X38 is L or P, X39 is A or M, X40 is M or V and X41 is P or F.

Analogously to this process, two further production processes for the mistletoe lectin A-chain (MLA) (SEQ ID NO: 2 and 41) and mistletoe lectin B-chain (MLB) (SEQ ID NO: 3) are made available, which contain the following sequences or a fragment thereof:

Mistletoe Lectin A

Y E R L R L R V T H Q T T G X1 E Y F R F I T L

L R D Y V S S G S F S N E I P L L R Q S T I P

V S D A Q R F V L V E L T N Q G X2 D S X3 T A A

I D V T N X4 Y V V A Y Q A G D Q S Y F L R D A

P R G A E T H L F T G T T R X5 S S L P F X6 G S

Y X7 D L E R Y A G H R D Q I P L G I X8 Q L I Q

S V X9 A L R X10 P G G S T R X11 Q A R S I L I L

I Q M I S E A A R F N P I L W R X12 R Q X13 I N

S G X14 S F L P D X15 Y M L E L E T S W G Q Q S

T Q V Q H S T D G V F N N P X16 R L A I X17 X18 G

N F V T L X19 N V R X20 V I A S L A I M L F V C

G E R P S S S

Mistletoe Lectin B

D D V T C S A S E P T V R I V G R X21 G M X22 V D

V R D D D F H D G N Q I Q L W P S K S N N D P N

Q L W T I K R D X23 T I R S N G S C L T T Y G Y

T A G V Y V M I F D C N T A V R E A T I W Q I W

X24 N G T I I N P R S N L V L A A S S G I K G T T

L T V Q T L D Y T L G Q G W L A G N D T A P R E

V T I Y G F R D L C M E S N X25 G S V W V E T C

X26 S S Q X27 N Q X28 X29 W A L Y G D G S I R P K Q

N Q D Q C L T X30 G R D S V S T V I N I V S C S X31

X32 S X33 X34 Q R W V F T N E X35 A I L N L K X36

X37 X38 X39 X40 D V A Q A N P K L R R I I I Y P A T

G K P N Q M W L P V X41 wherein X1 to X41 have the meaning stated above.

Furthermore, a mistletoe lectin polypeptide or a fragment thereof, which includes the sequence variability of the various MLA and MLB chains, having the following sequence is provided (SEQ ID NO: 1 and SEQ ID NO: 40):

Y E R L R L R V T H Q T T G X1 E Y F R F I T L

L R D Y V S S G S F S N E I P L L R Q S T I P

V S D A Q R F V E L T N Q G X2 D S X3 T A A

I D V T N X4 Y V V A Y Q A G D Q S Y F L R D A

P R G A E T H L F T G T T R X5 S S L P F X6 G S

Y X7 D L E R Y A G H R D Q I P L G I X8 Q L I Q

S V X9 A L R X10 P G G S T R X11 Q A R S I L I L

I Q M I S E A A R F N P I L W R X12 R Q X13 I N

S G X14 S F L P D X15 Y M L E L E T S W G Q Q S

T Q V Q H S T D G V F N N P X16 R L A I X17 X18 G

N F V T L X19 N V R X20 V I A S L A I M L F V C

G E R P S S S D V R Y W P L V I R P V I A D D

V T C S A S E P T V R I V G R X21 G M X22 V D V

R D D D F H D G N Q I Q L W P S K S N N D P N

Q L W T I K R D X23 T I R S N G S C L T T Y G Y

T A G V Y V M I F D C N T A V R E A T I W Q I

W X24 N G T I I N P R S N L V L A A S S G I K G

T T L T V Q T L D Y T L G Q G W L A G N D T A

P R E V T I Y G F R D L C M E S N X25 G S V W V

E T C X26 S S Q X27 N Q X28 X29 W A L Y G D G S I R

P K Q N Q D Q C L T X30 G R D S V S T V I N I V

S C S X31 X32 S X33 X34 Q R W V F T N E X35 A I L N

L K X36 X37 X38 X39 X40 D V A Q A N P K L R R I I I

Y P A T G K P N Q M W L P V X41

Apart from this, mistletoe lectin polypeptides of the mistletoe lectin A-chain (SEQ I D NO: 2 and 41) and mistletoe lectin B-chain (SEQ ID NO: 3) or fragments of these sequences are provided, which include the following sequences:

Mistletoe Lectin A

Y E R L R L R V T H Q T T G X1 E Y F R F I T L

L R D Y V S S G S F S N E I P L L R Q S T I P

V S D A Q R F V L V E L T N Q G X2 D S X3 T A A

I D V T N X4 I V V A Y Q A G D Q S Y F L R D A

P R G A E T H L F T G T T R X5 S S L P F X6 G S

Y X7 D L E R Y A G H R D Q I P L G I X8 Q L I Q

S V X9 A L R X10 P G G S T R X11 Q A R S I L I L

I Q M I S E A A R F N P I L W R X12 R Q X13 I N

S G X14 S F L P D X15 Y M L E L E T S W G Q Q S

T Q V Q H S T D G V F N N P X16 R L A I X17 X18 G

N F V T L X19 N V R X20 V I A S L A I M L F V C

G E R P S S S

Mistletoe Lectin B

D D V T C S A S E P T V R I V G R X21 G M X22 V D

V R D D D F H D G N Q I Q L W P S K S N N D P N

Q L W T I K R D X23 T I R S N G S C L T T Y G Y

-continued

T A G V Y V M I F D C N T A V R E A T I W Q I W

X24 N G T I I N P R S N L V L A A S S G I K G T T

L T V Q T L D Y T L G Q G W L A G N D T A P R E

V T I Y G F R D L C M E S N X25 G S V W V E T C

X26 S S Q X27 N Q X28 X29 W A L Y G D G S I R P K Q

N Q D Q C L T X30 G R D S V S T V I N I V S C S X31

X32 S X33 X34 Q R W V F T N E X35 A I L N L K X36

X37 X38 X39 X40 D V A Q A N P K L R R I I I Y P A T

G K P N Q M W L P V X41 wherein X1 to X41 have the meaning stated above.

The sequence which includes the above-described variability of the ML-I polypeptides occurring in mistletoe cells is shown in FIG. 1b (SEQ ID NO: 4). A specific sequence for MLA2 of mistletoe lectin I, which was likewise produced according to the process presented above, is shown in FIG. 3b (SEQ ID NO: 38). FIGS. 7b to 12b (SEQ ID NOS: 6–11) include specific mistletoe lectin B-chain sequences, which were likewise produced according to the process described above.

A further aspect of the present invention is a process for the provision of a nucleic acid molecule, which codes for a mistletoe lectin polypeptide in a heterologous host as described above and includes the following steps:
a) preparing of mistletoe cell RNA or chromosomal mistletoe cell DNA and
b) amplifying mistletoe cell RNA or chromosomal mistletoe lectin DNA by PCR using oligonucleotides which are derived from the mistletoe lectin polypeptide shown in FIG. 1b (SEQ ID NO: 4), and
c) if necessary, identifying of sequences which lie 5' and 3' from the amplified nucleic acid and amplification thereof, and
d) isolating of the nucleic acid molecules amplified in step b) and/or c), and
e) if necessary, ligating of several of the nucleic acid molecules amplified in step b) and/or c), such that a nucleic acid molecule with a complete open reading frame is obtained and
f) targeted mutation of the nucleic acid molecule obtained in order to match the nucleic acid molecule to the usual genetic code of the heterologous host for one of the mistletoe lectin polypeptide isoforms identified in mistletoe cells.

For the preparation of mistletoe cell DNA, mistletoe plants (*Viscum album L.* ssp. *platyspermum* Kell), which had been harvested from poplars from Alsace, were crushed in liquid nitrogen and the chromosomal DNA extracted (Example 1). Using the degenerate oligonucleotides shown below, fragments of the genomic mistletoe lectin DNA were amplified by means of the PCR process (Example 2). The degenerate oligonucleotides used in the PCR reaction, which hybridise to regions of the MLB chain DNA, have the sequence:
(BI):

GTN MGN GAY GAY GAY TTY CA (SEQ ID NO:33)

(BII):

AT YTG RTT NGG YTT NCC NGT (SEQ ID NO: 34)

The abbreviations of the nucleotides here are based on the designation proposed by the IUPAC-IUB Biochemical Nomenclature Commission.

In a further reaction step, using specific oligonucleotides, the 5'- and 3'-lying sequences of the first amplification product were determined by means of the rapid amplification of cDNA ends (RACE) technique (Example 3). The oligonucleotide used for the 5'-RACE reaction has the following sequence:

CAC AGC AGT ATT ACA GTC GAA (SEQ ID NO: 35)

The oligonucleotide used for the 3'-RACE reaction has the following sequence (SEQ ID NO: 36):

GTC TAT GTG ATG ATC TTC GAC TGT.

The complete nucleic sequence thus obtained was used for the synthesis of specific oligonucleotides in order to obtain a whole clone by means of the PCR Alternatively, the partly overlapping clones were cleaved using suitable restriction cleavage sites, in order to be assembled in a suitable vector, so that a complete open reading frame of the mistletoe lectin I gene was obtained. Deliberate mutations can be introduced into these DNA constructs by known techniques, e.g. by replacement of certain DNA regions by other DNA fragments, introduction of not completely homologous oligonucleotides, etc. These mutations can serve on the one hand to modify the amino acid sequence derived therefrom and thus to influence the activity of the polypeptide, or on the other hand to vary the nucleic acid sequence, without modifying the amino acid sequence, in order e.g. to imitate the preferred codon usage of a host organism.

Nucleic acid molecules which are made available by this process and code for a polypeptide as described above, include the following sequences for ML-I (SEQ ID NO: 12), MLA (SEQ ID NO: 13) and MLB (SEQ ID NO: 14) or fragments thereof:

1) ML-I Sequence

TACGAGAGGCTAAGACTCAGAGTTACGCATCAAACCACGGGCGAKGAATACTTCCGGTTCATCACG

CTTCTCCGAGATTATGTCTCAAGCGGAAGCTTTTCCAATGAGATACCACTCTTGCGTCAGTCTACG

ATCCCCGTCTCCGATGCGCAAAGATTTGTCTTGGTGGAGCTCACCAACCAGGGGSRRGACTCGRTY

ACGGCCGCCATCGACGTTACCAATSYKTACGTCGTGGCTTACCAAGCAGGCGACCAATCCTACTTT

TTGCGCGACGCACCACGCGGCGCGGAAACGCACCTCTTCACCGGCACCACCCGAZ1TCCTCTCTCC

CATTCAMYGGAAGCTACMCYGATCTGGAGCGATACGCCGGACATAGGGACCAGATCCCTCTCGGTA

-continued

```
TAGASCAACTCATTCAATCCGTCWCKGCGCTTCGTTWYCCGGGCGGCAGCACGCGTRCYCAAGCTC

GTTCGATTTTAATCCTCATTCAGATGATCTCCGAGGCCGCCAGATTCAATCCCATCTTATGGAGGK

MYCGCCAAKAYATTAACAGTGGGGMRTCATTTCTGCCAGACRTGTACATGCTGGAGCTGGAGACGA

GTTGGGGCCAACAATCCACGCAAGTCCAGCATTCAACCGATGGCGTTTTTAATAACCCAWTYCGGT

TGGCTATAYCYMCYGGTAACTTCGTGACGTTGWCYAATGTTCGCKMYGTGATCGCCAGCTTGGCGA

TCATGTTGTTTGTATGCGGAGAGCGGCCATCTTCCTCTGACGTGCGCTATTGGCCGCTGGTCATAC

GACCCGTGATAGCCGATGATGTTACCTGCAGTGCTTCGGAACCTACGGTGCGGATTGTGGGTCGAA

RTGGCATGYGCGTGGACGTCCGAGATGACGATTTCCACGATGGGAATCAGATACAGTTGTGGCCCT

CCAAGTCCAACAATGATCCGAATCAGTTGTGGACGATCAAAAGGGATRRMACCATTCGATCCAATG

GCAGCTGCTTGACCACGTATGGCTATACTGCTGGCGTCTATGTGATGATCTTCGACTGTAATACTG

CTGTGCGGGAGGCCACTATTTGGCAGATATGGGRCAATGGGACCATCATCAATCCAAGATCCAATC

TGGTTTTGGCAGCATCATCTGGAATCAAAGGCACTACGCTTACGGTGCAAACACTGGATTACACGT

TGGGACAGGGCTGGCTTGCCGGTAATGATACCGCCCCACGCGAGGTGACCATATATGGTTTCAGGG

ACCTTTGCATGGAATCAAATSRAGGGAGTGTGTGGGTGGAGACGTGCGWSAGTAGCCAAMAGAACC

AAZ2ARATGGGCTTTGTACGGGGATGGTTCTATACGCCCCAAACAAAACCAAGACCAATGCCTCAC

CKBTGGGAGAGACTCCGTTTCAACAGTAATCAATATAGTTAGCTGCAGCGSWGSWTCGKSKKSKCA

GCGATGGGTGTTTACCAATGAAKRSGCCATTTTGAATTTAAAGAVWRGSYYGRYSRTGGATGTGGC

GCAAGCAAATCCAAAGCTCCGCCGAATAATTATCTATCCTGCCACAGGAAAACCAAATCAAATGTG

GCTTCCCGTGYYMTGA
```

II) MLA Sequence

```
TACGAGAGGCTAAGACTCAGAGTTACGCATCAAACCACGGGCGAKGAATACTTCCGGTTCATCACG

CTTCTCCGAGATTATGTCTCAAGCGGAAGCTTTTCCAATGAGATACCACTCTTGCGTCAGTCTACG

ATCCCCGTCTCCGATGCGCAAAGATTTGTCTTGGTGGAGCTCACCAACCAGGGGSRRGACTCGRTY

ACGGCCGCCATCGACGTTACCAATSYKTACGTCGTGGCTTACCAAGCAGGCGACCAATCCTACTTT

TTGCGCGACGCACCACGCGGCGCGGAAACGCACCTCTTCACCGGCACCACCCGAZ1TCCTCTCTCC

CATTCAMYGGAAGCTACMCYGATCTGGAGCGATACGCCGGACATAGGGACCAGATCCCTCTCGGTA

TAGASCAACTCATTCAATCCGTCWCKGCGCTTCGTTWYCCGGGCGGCAGCACGCGTRCYCAAGCTC

GTTCGATTTTAATCCTCATTCAGATGATCTCCGAGGCCGCCAGATTCAATCCCATCTTATGGAGGK

MYCGCCAAKAYATTAACAGTGGGGMRTCATTTCTGCCAGACRTGTACATGCTGGAGCTGGAGACGA

GTTGGGGCCAACAATCCACGCAAGTCCAGCATTCAACCGATGGCGTTTTTAATAACCCAWTYCGGT

TGGCTATAYCYMCYGGTAACTTCGTGACGTTGWCYAATGTTCGCKMYGTGATCGCCAGCTTGGCGA

TCATGTTGTTTGTATGCGGAGAGCGGCCATCTTCCTCT
```

III) MLB Sequence

```
GATGATGTTACCTGCAGTGCTTCGGAACCTACGGTGCGGATTGTGGGTCGAARTGGCATGYGCGTG

GACGTCCGAGATGACGATTTCCACGATGGGAATCAGATACAGTTGTGGCCCTCCAAGTCCAACAAT

GATCCGAATCAGTTGTGGACGATCAAAAGGGATRRMACCATTCGATCCAATGGCAGCTGCTTGACC

ACGTATGGCTATACTGCTGGCGTCTATGTGATGATCTTCGACTGTAATACTGCTGTGCGGGAGGCC
```

-continued

```
ACTATTTGGCAGATATGGGRCAATGGGACCATCATCAATCCAAGATCCAATCTGGTTTTGGCAGCA

TCATCTGGAATCAAAGGCACTACGCTTACGGTGCAAACACTGGATTACACGTTGGGACAGGGCTGG

CTTGCCGGTAATGATACCGCCCCACGCGAGGTGACCATATATGGTTTCAGGGACCTTTGCATGGAA

TCAAATSRAGGGAGTGTGTGGGTGGAGACGTGCGWSAGTAGCCAAMAGAACCAAZ2ARATGGGCTT

TGTACGGGGATGGTTCTATACGCCCCAAACAAAACCAAGACCAATGCCTCACCKBTGGGAGAGACT

CCGTTTCAACAGTAATCAATATAGTTAGCTGCAGCGSWGSWTCCKSKKSKCACCCATCCCTCTTTA

CCAATGAAKRSGCCATTTTGAATTTAAAGAVWRGSYYGRYSRTGGATGTGGCGCAAGCAAATCCAA

AGCTCCGCCGAATAATTATCTATCCTGCCACAGGAAAACCAAATCAAATGTGGCTTCCCGTGYYMT

GA
```

The nucleotides are defined in accordance with the IUPAC-IUB code; $Z_1$ designates the nucleotide sequence GAT AGA or is missing, while $Z_2$ designates the nucleotide GGC or is missing.

A specific nucleic acid molecule which was prepared by the process stated above and includes the entire ML-I coding sequence, is shown in FIG. 1*a* (SEQ ID NO: 15). Further specific nucleic acid molecules, which code for the MLA chain of mistletoe lectin I and were prepared by the process stated above, are shown in FIG. 2*a* (SEQ ID NO: 16) and FIG. 2*b* (SEQ ID NO: 37). Specific sequences for MLB nucleic acid molecules, which were prepared by the process described above, are listed in FIGS. 7*a* to 12*a* (SEQ ID NOS: 21–26). Here, each of these nucleic acid sequences codes for a polypeptide which emerged by protein sequencing of the ML-I mixture from natural mistletoe extract.

In addition, the present invention includes nucleic acid molecules which code for a mistletoe lectin polypeptide, as described above, and are characterized in that the codon usage is matched to the requirements of a heterologous host. FIG. 4*a* (SEQ ID NO: 18) shows such a nucleic acid sequence, wherein the codon usage is matched to the preferred codon usage of the genus *Brassica*. This genus was chosen, since both as the Summer and also as the Winter form it thrives outstandingly in the middle latitudes of Europe, North America and Asia. The possible uses of rape for the production of recombinant proteins have been demonstrated by various firms and research institutes. Examples, of its use are the production of gastric lipase for use in the treatment of cystic fibrosis or coupling to oleosins for greater ease of purification of the recombinant proteins from the lipid phase of the rape oil seeds.

The sequences shown in FIGS. 5*a* (SEQ ID NO: 19), 6*a* (SEQ ID NO: 20), and 13*a* to 18*a* (SEQ ID NOS: 27–32) represent nucleic acid molecules which code for MLA polypeptides or for MLB polypeptides of mistletoe lectin I and whose codon usage is likewise matched to the genus *Brassica*. The degree of homology between these matched sequences to the nucleic acid sequences shown in FIGS. 2*a* (SEQ ID NO: 16) and 7*a* (SEQ ID NO:21) is ca. 61% for MLA and about 63% for MLB.

Further, through the present invention a vector is made available, which includes one of the nucleic acid molecules described above or a fragment thereof and also a promoter regulating the expression of this nucleic acid molecule. In a preferred embodiment, this vector contains, in functional linkage with the nucleic acid molecules described above, a promoter which can only be activated in the intended host cell. The host cell here can be a plant or an animal cell. Host-specific promoters are already used, sometimes together with cell type-specific, regulated enhancer sequences, for the selective expression of therapeutic genes (Walter W and Stein U, Molecular Biotechnology, 1996, 6 (3), 267–86). Likewise, systems have been developed, wherein inducers and repressors act on a genetically modified transcription factor, which specifically recognises a likewise modified promoter. This allows the regulated expression of e.g. therapeutic proteins, without at the same time non-specifically activating cellular promoters (Miller N and Whelan J, Human Gene Therapy, 1997, 8 (7), 803–815).

A preferred vector is an RNA vector, such as for example described in Kumagai et al., Proc. Natl. Acad. Sci., USA, 1993, 90, 427–430. Compared to other plant expression systems, this system offers the advantages firstly that high yields of recombinant proteins can be achieved and secondly a considerably faster establishment of the process takes place, since only the RNA vector is genetically modified, and after infection the plant starts the production of the recombinant protein.

Host systems which are to serve for the heterologous expression of the nucleic acids described above can be selected from the group including bacterial cells, plant cells with the exception of mistletoe cells, insect cells, insect larvae, vertebrate cells, preferably mammalian cells, yeast cells, fungal cells, transgenic vertebrates with the exception of man and/or transgenic plants with the exception of mistletoe plants. Here preferably *Escherichia coli* are used as bacterial by cells, rape cells as plant cells, *Trichoplusia ni* as insect larvae, *Spodoptera frugiperda* cells as insect cells and zebra fish as vertebrates.

The present invention includes pharmaceutical compositions which contain at least one of the aforementioned nucleic acid molecules or one of the vectors described above.

A preferred pharmaceutical composition in addition contains liposomes, which enclose the linear nucleic acid molecules or the vectors, in order to protect them against nucleolytic degradation. At the same time, these liposomes can bear cell recognition molecules on their surface, which enable selective attachment to specific target cells. Such so-called "second generation" surface-modified liposomes (e.g. immunoliposomes and "long-circulating liposomes") are already being successfully used for the targeted transfection of specific cell types from cancer patients (Storm G and Crommelin D J, Hybridoma, 1997, 16 (1), 119–125, Thierry A R et al., Gene Therapy, 1997, 4 (3), 226–237).

A further pharmaceutical composition is specified, wherein the linear nucleic acid molecule or the vector is coupled directly or via a linker system (e.g. biotin-streptavidin coupling) to one of the MLB polypeptides described above. Here the MLB polypeptide unit mediates the attachment of the complex to sugar-containing structures on the cell membrane and induces the endocytotic uptake of the complex. In this way, for example a nucleic acid coding for the cytotoxic MLA can be specifically transported into a cell, where it is subsequently translated into a protein and then inactivates the cell's own ribosomes. In addition, such a complex can contain peptides such as for example antibodies, antibody fragments or receptor-binding peptides (ligands), which are capable of effecting cell-specific binding.

A further preferred pharmacological composition includes a virus particle, as well as the linear nucleic acid molecule or the vector. In this case, a virus vector is preferred. Here the virus particle can likewise on its surface bear cell recognition molecules for specific cell recognition. These molecules can be e.g. fusion proteins of viral proteins with cell-specific-ally binding polypeptides. By presentation of these peptides on the surface of the virus particle, a targeted attachment of these particles can be achieved (Joelson T et al., Journal of General Virology, 78 (6), 1213–1217, Grabherr R et al., Biotechnics, 1997, 22 (4), 730–735).

The present invention further includes a pharmaceutical composition which contains at least one of the mistletoe lectin polypeptides described above and/or at least one fragment thereof as cytotoxic component. The pharmaceutical efficiency of such a composition can once again be heightened by coupling of the polypeptides or the polypeptide fragments with cell recognition molecules which bind selectively to target cells. In a preferred embodiment of the pharmaceutical composition, the cell recognition molecule is an antibody molecule, an antibody fragment or any other protein and peptide molecule, which has the capacity specifically to bind to the target cells, e.g. a peptide hormone or a fragment of this hormone such as the "gonadotropin-releasing hormone" and such fragments which specifically bind to receptors of adenocarcinoma cells or peptides which in a specific form of leukaemia bind to the inter-leukin-2 growth factor of the lymphoma cells ("cutaneous T cell lymphoma"). Non-protein molecules which concentrate in target cells or bind to them, such as cis-platin or haem and precursors thereof, can be also suitable cell recognition molecules for coupling to the cyto-toxic component of the ML-I. Owing to the fact that the cytotoxic component specifically gets into the cell interior of the degenerated cells, the dose of toxin can be kept relatively low and side-effects on healthy tissue minimised.

Here these cell recognition molecules can be coupled to the mistletoe lectin polypeptides by known chemical processes. Furthermore, it is possible to create fusion proteins from the polypeptides described above and a suitable antibody or a fragment thereof in one of the host systems likewise described above. Also suitable as fusion proteins are e.g. recombinant proteins which consist of a polypeptide described here and an IL-2 receptor-binding "homing" component or a genetically modified fragment of gonadotropin-releasing factor.

A pharmaceutical composition according to the invention contains at least one of the polypeptides described above and/or a fragment thereof, as a rule together with a pharmaceutically compatible vehicle. Here a defined mixture of different MLA and/or MLB polypeptides corresponding to the needs of the patient can be composed. In order to recreate the diversity of the mistletoe lectin I isoenzyme of natural mistletoe extract, a cytotoxic composition preferably contains several or all of the above-stated MLA/MLB polypeptides. The pharmaceutically tolerable carrier can be a buffer, a diluent, a filler, solvent, lubricant, flavouring, binder, preservative and/or occluding material. The pharmaceutical composition is formulated such that it is suitable both for oral and also parenteral administration, in particular subcutaneous, intramuscular and intravenous administration. In certain diseases, inhalational, rectal, vaginal and cutaneous presentations can also be used.

On account of an anti-tumorigenic action, an above-mentioned mistletoe lectin polypeptide or a fragment thereof can be used for production of a medicament for treatment of uncontrolled cell growth, e.g. of cancer. Furthermore, such a mistletoe lectin polypeptide or a fragment thereof, whose cytotoxic activity has been blocked, e.g. by modifications at the active centre (amino acids $Y_{76}$, $Y_{115}$, $E_{165}$, $R_{168}$, $W_{199}$), in combination with at least one further antigen, can be used for the production of a medicament, which is capable of intensifying the immune reaction against the further antigen. For example, from European Patent 0 320 528, proteins are already known (haemocyanins and arylphorins), which can cause a strong antigenic reaction. Similarly to these substances, the mistletoe lectins according to the invention can also trigger an activation of T-lymphocytes and lymphokine-producing macrophages and as a result strengthen the endogeneous defences.

Furthermore, the present invention also includes a process for the production of a mistletoe lectin polypeptide in mistletoe cells and/or transgenic mistletoe plants having the following sequence (SEQ ID NO: 1 and 40):

Y E R L R L R V T H Q T T G X1 E Y F R F I T L

L R D Y V S S G S F S N E I P L L R Q S T I P

V S D A Q R F V L V E L T N Q G X2 D S X3 T A A

I D V T N X4 Y V V A Y Q A G D Q S Y F L R D A

P R G A E T H L F T G T T R X5 S S L P F X6 G S

Y X7 D L E R Y A G H R D Q I P L G I X8 Q L I Q

S V X9 A L R X10 P G G S T R X11 Q A R S I L I L

I Q M I S E A A R F N P I L W R X12 R Q X13 I N

S G X14 S F L P D X15 Y M L E L E T S W G Q Q S

T Q V Q H S T D G V F N N P X16 R L A I X17 X18 G

N F V T L X19 N V R X 20 V I A S L A I M L F V C

G E R P S S S D V R Y W P L V I R P V I A D D

V T C S A S E P T V R I V G R X21 G M X22 V D V

R D D D F H D G N Q I Q L W P S K S N N D P N

Q L W T I K R D X23 T I R S N G S C L T T Y G Y

T A G V Y V M I F D C N T A V R E A T I W Q I

W X24 N G T I I N P R S N L V L A A S S G I K G

T T L T V Q T L D Y T L G Q G W L A G N D T A

P R E V T I Y G F R D L C M E S N X25 G S V W V

E T C X26 S S Q X27 N Q X28 X29 W A L Y G D G S I R

P K Q N Q D Q C L T X30 G R D S V S T V I N I V

S C S X31 X32 S X33 X34 Q R W V F T N E X35 A I L N

L K X36 X37 X38 X39 X40 D V A Q A N P K L R R I I I

Y P A T G K P N Q M W L P V X41 comprising the step of expressing a eukaryotic vector, which contains a nucleic acid coding for the mistletoe lectin polypeptide or a fragment thereof having the nucleic acid sequence originally found in mistletoe cell DNA, in a mistletoe cell or a transgenic mistletoe plant, wherein the transcription product of this nucleic acid molecule is modified in mistletoe cells or transgenic mistletoe plants by RNA editing and further normally occurring posttranscript-ional and/or posttranslational mechanisms and thus possibly leads to the production of the natural mistletoe lectin mixture, wherein X1 is D or E, X2 is G or Q, X3 is I or V, X4 is L or A, X5 is DR or missing, X6 is N or T, X7 is P or T, X8 is D or E, X9 is S or T, X10 is F or Y, X11 is T or A, X12 is A or Y, X13 is Y or D, X14 is A or E, X15 is V or M, X16 is I or F, X17 is P or S, X18 is P or T, X19 is T or S, X20 is D or S, X21 is N or S, X22 is C or R, X23 is G or N, X24 is G or D, X25 is G or Q, X26 is V or D, X27 is Q or K, X28 is G or missing, X29 is R or K, X30 is C or S or V, X31 is A or G, X32 is G or A, X33 is S or G, X34 is G or S, X35 is G or Y, X36 is N or S or T or K, X37 is S or G, X38 is L or P, X39 is A or M, X40 is M or V and X41 is P or F.

On the basis of the process described above, two further production processes for the mistletoe lectin A-chain (SEQ ID NO: 2 and 41) and mistletoe lectin B-chain (SEQ ID NO: 3) or a fragment thereof are provided, which contain the following sequences or a fragment thereof.

Mistletoe Lectin A

Y E R L R L R V T H Q T T G X1 E Y F R F I T L

L R D Y V S S G S F S N E I P L L R Q S T I P

V S D A Q R F V L V E L T N Q G X2 D S X3 T A A

I D V T N X4 Y V V A Y Q A G D Q S Y F L R D A

P R G A E T H L F T G T T R X5 S S L P F X6 G S

Y X7 D L E R Y A G H R D Q I P L G I X8 Q L I Q

S V X9 A L R X10 P G G S T R X11 Q A R S I L I L

I Q M I S E A A R F N P I L W R X12 R Q X13 I N

S G X14 S F L P D X15 Y M L E L E T S W G Q Q S

T Q V Q H S T D G V F N N P X16 R L A I X17 X18 G

N F V T L X19 N V R X20 V I A S L A I M L F V C

G E R P S S S

Mistletoe Lectin B

D D V T C S A S E P T V R I V G R X21 G M X22 V D

V R D D D F H D G N Q I Q L W P S K S N N D P N

Q L W T I K R D X23 T I R S N G S C L T T Y G Y

T A G V Y V M I F D C N T A V R E A T I W Q I W

X24 N G T I I N P R S N L V L A A S S G I K G T T

L T V Q T L D Y T L G Q G W L A G N D T A P R E

-continued

V T I Y G F R D L C M E S N X25 G S V W V E T C

X26 S S Q X27 N Q X28 X29 W A L Y G D G S I R P K Q

N Q D Q C L T X30 G R D S V S T V I N I V S C S X31

X32 S X33 X34 Q R W V F T N E X35 A I L N L K X36

X37 X38 X39 X40 D V A Q A N P K L R R I I I Y P A T

G K P N Q M W L P V X41

A process according to the invention for the provision of a nucleic acid molecule, which codes for the above-mentioned mistletoe lectin polypeptide in a mistletoe cell or a transgenic mistletoe plant, comprises the following steps:

a) preparing of mistletoe cell RNA or chromosomal mistletoe cell DNA and b) amplifying mistletoe cell RNA or chromosomal mistletoe lectin DNA by PCR using oligonucleotides which are derived from the mistletoe lectin polypeptide shown in FIG. 1b (SEQ ID NO: 4), and c) if necessary, identifying of sequences which lie 5' and 3' from the amplified nucleic acid and amplification thereof, and d) isolating of the nucleic acid molecules amplified in step b) and/or c), and e) if necessary, ligating of several of the nucleic acid molecules isolated in step b) and/or c), such that a nucleic acid molecule with a complete open reading frame is obtained and f) if necessary, targeted mutation of the nucleic acid molecule obtained in order to match the nucleic acid molecule to the usual genetic code for one of the mistletoe lectin polypeptide isoforms identified in mistletoe cells and/or to optimise expression.

Firstly, plant RNA or DNA is isolated preferably from fresh material by various generally known processes (Quiagen experimental protocol, Nickrent D L et al., American Journal of Botany, vol. 81, No. 9 (1994): 1149–1160; Example 1). Using the degenerate oligonucleotides BI and BII described in Example 1, which are derived from the mistletoe lectin polypeptide shown in FIG. 1b (SEQ ID NO: 4), the mistletoe lectin-I gene is amplified in a PCR reaction, the conditions for which are set out in Example 2. If this amplification step does not include the complete open reading frame of ML-I, the 5' and 3' region of the amplified nucleic acids can be identified using the RACE technique with the respective oligonucleotides stated in Example 3. The nucleic acid molecules thus obtained are isolated and if necessary ligated into a vector using suitable restriction cleavage sites in such a way that this contains the complete open reading frame. A nucleic acid molecule or a fragment thereof contained in this vector, which codes for a polypeptide such as described above in a mistletoe cell or a transgenic mistletoe plant, comprises the following sequence (SEQ ID NO: 12):

1) ML-I Sequence

```
TACGAGAGGCTAAGACTCAGAGTTACGCATCAAACCACGGGCGAKGAATACTTCCGGTTCATCACG

CTTCTCCGAGATTATGTCTCAAGCGGAAGCTTTTCCAATGAGATACCACTCTTGCGTCAGTCTACG

ATCCCCGTCTCCGATGCGCAAAGATTTGTCTTGGTGGAGCTCACCAACCAGGGGSRRGACTCGRTY

ACGGCCGCCATCGACGTTACCAATSYKTACGTCGTGGCTTACCAAGCAGGCGACCAATCCTACTTT
```

-continued

```
TTGCGCGACGCACCACGCGGCGCGGAAACGCACCTCTTCACCGGCACCACCCGAZ1TCCTCTCTCC

CATTCAMYGGAAGCTACMCYGATCTGGAGCGATACGCCGGACATAGGGACCAGATCCCTCTCGGTA

TAGASCAACTCATTCAATCCGTCWCKGCGCTTCGTTWYCCGGGCGGCAGCACGCGTRCYCAAGCTC

GTTCGATTTTAATCCTCATTCAGATGATCTCCGAGGCCGCCAGATTCAATCCCATCTTATGGAGGK

MYCGCCAAKAYATTAACAGTGGGGMRTCATTTCTGCCAGACRTGTACATGCTGGAGCTGGAGACGA

GTTGGGGCCAACAATCCACGCAAGTCCAGCATTCAACCGATGGCGTTTTTAATAACCCAWTYCGGT

TGGCTATAYCYMCYGGTAACTTCGTGACGTTGWCYAATGTTCGCKMYGTGATCGCCAGCTTGGCGA

TCATGTTGTTTGTATGCGGAGAGCGGCCATCTTCCTCTGACGTGCGCTATTGGCCGCTGGTCATAC

GACCCGTGATAGCCGATGATGTTACCTGCAGTGCTTCGGAACCTACGGTGCGGATTGTGGGTCGAA

RTGGCATGYGCGTGGACGTCCGAGATGACGATTTCCACGATGGGAATCAGATACAGTTGTGGCCCT

CCAAGTCCAACAATGATCCGAATCAGTTGTGGACGATCAAAAGGGATRRMACCATTCGATCCAATG

GCAGCTGCTTGACCACGTATGGCTATACTGCTGGCGTCTATGTGATGATCTTCGACTGTAATACTG

CTGTGCGGGAGGCCACTATTTGGCAGATATGGGRCAATGGGACCATCATCAATCCAAGATCCAATC

TGGTTTTGGCAGCATCATCTGGAATCAAAGGCACTACGCTTACGGTGCAAACACTGGATTACACGT

TGGGACAGGGCTGGCTTGCCGGTAATGATACCGCCCCACGCGAGGTGACCATATATGGTTTCAGGG

ACCTTTGCATGGAATCAAATSRAGGGAGTGTGTGGGTGGAGACGTGCGWSAGTAGCCAAMAGAACC

AAZ2ARATGGGCTTTGTACGGGGATGGTTCTATACGCCCCAAACAAAACCAAGACCAATGCCTCAC

CKBTGGGAGAGACTCCGTTTCAACAGTAATCAATATAGTTAGCTGCAGCGSWGSWTCGKSKKSKCA

GCGATGGGTGTTTACCAATGAAARSGCCATTTTGAATTTAAAGAVWRGSYYGRYSRTGGATGTGGC

GCAAGCAAATCCAAAGCTCCGCCGAATAATTATCTATCCTGCCACAGGAAAACCAAATCAAATGTG

GCTTCCCGTGYYMTGA
```

A nucleic acid molecule according to the invention or a fragment thereof, which codes for one of the above-mentioned MLA polypeptides in a mistletoe cell or a transgenic mistletoe plant, comprises the following sequence (SEQ ID NO: 13):

II) MLA Sequence

```
TACGAGAGGCTAAGACTCAGAGTTACGCATCAAACCACGGGCGAKGAATACTTCCGGTTCATCACG

CTTCTCCGAGATTATGTCTCAAGCGGAAGCTTTTCCAATGAGATACCACTCTTGCGTCAGTCTACG

ATCCCCGTCTCCGATGCGCAAAGATTTGTCTTGGTGGAGCTCACCAACCAGGGGSRRGACTCGRTY

ACGGCCGCCATCGACGTTACCAATSYKTACGTCGTGGCTTACCAAGCAGGCGACCAATCCTACTTT

TTGCGCGACGCACCACGCGGCGCGGAAACGCACCTCTTCACCGGCACCACCCGAZ1TCCTCTCTCC

CATTCAMYGGAAGCTACMCYGATCTGGAGCGATACGCCGGACATAGGGACCAGATCCCTCTCGGTA

TAGASCAACTCATTCAATCCGTCWCKGCGCTTCGTTWYCCGGGCGGCAGCACGCGTRCYCAAGCTC

GTTCGATTTTAATCCTCATTCAGATGATCTCCGAGGCCGCCAGATTCAATCCCATCTTATGGAGGK

MYCGCCAAKAYATTAACAGTGGGGMRTCATTTCTGCCAGACRTGTACATGCTGGAGCTGGAGACGA

GTTGGGGCCAACAATCCACGCAAGTCCAGCATTCAACCGATGGCGTTTTTAATAACCCAWTYCGGT

TGGCTATAYCYMCYGGTAACTTCGTGACGTTGWCYAATGTTCGCKMYGTGATCGCCAGCTTGGCGA
```

Furthermore, a nucleic acid molecule or a fragment thereof, which codes for one of the above-mentioned MLB polypeptides in a mistletoe cell or a transgenic mistletoe plant, having the following sequence is made available (SEQ ID NO: 14):

III) MLB Sequence

GATGATGTTACCTGCAGTGCTTCGGAACCTACGGTGCGGATTGTGGGTCGAARTGGCATGYGCGTG

GACGTCCGAGATGACGATTTCCACGATGGGAATCAGATACAGTTGTGGCCCTCCAAGTCCAACAAT

GATCCGAATCAGTTGTGGACGATCAAAAGGGATRRMACCATTCGATCCAATGGCAGCTGCTTGACC

ACGTATGGCTATACTGCTGGCGTCTATGTGATGATCTTCGACTGTAATACTGCTGTGCGGGAGGCC

ACTATTTGGCAGATATGGGRCAATGGGACCATCATCAATCCAAGATCCAATCTGGTTTTGGCAGCA

TCATCTGGAATCAAAGGCACTACGCTTACGGTGCAAACACTGGATTACACGTTGGGACAGGGCTGG

CTTGCCGGTAATGATACCGCCCCACGCGAGGTGACCATATATGGTTTCAGGGACCTTTGCATGGAA

TCAAATSRAGGGAGTGTGTGGGTGGAGACGTGCGWSAGTAGCCAAMAGAACCAAZ2ARATGGGCTT

TGTACGGGGATGGTTCTATACGCCCCAAACAAAACCAAGACCAATGCCTCACCKBTGGGAGAGACT

CCGTTTCAACAGTAATCAATATAGTTAGCTGCAGCGSWGSWTCGKSKKSKCAGCGATGGGTGTTTA

CCAATGAAKRSGCCATTTTGAATTTAAAGAVWRGSYYGRYSRTGGATGTGGCGCAAGCAAATCCAA

AGCTCCGCCGAATAATTATCTATCCTGCCACAGGAAAACCAAATCAAATGTGGCTTCCCGTGYYMT

GA

The nucleotides are defined in accordance with the IUPAC-IUB code; in addition, $Z_1$ designates the nucleotide sequence GAT AGA or is missing, while $Z_2$ designates the nucleotide GGC or is missing.

A specific nucleic acid molecule which is to be expressed in a mistletoe cell or in a transgenic mistletoe plant and codes for ML-I, is shown in FIG. 1a (SEQ ID NO: 15). Further specific nucleic acid plants, which are modified in their codon usage in such a manner that as a result the expression rate is optimized.

Furthermore, the present invention makes available a process for the production of one of the above-described polypeptides, which includes the modification of sugar side-chains by enzymatic and/or chemical addition, removal and/or modification of one or several side-chains (Macindoe W M et al., Carbohydrate Research, 1995, 269 (2): 227–57; Meynial-Salles I and Combes D, J. Biotechnol., 1996, 46 (1), 1–14, Wong S Y, Current Opinion in Structural Biology, 1995, 5 (5), 599–604). In this way, the in vivo activity of individual MLA and/or MLB chains can be strengthened or weakened or in the event of any variations dependent on the expression system can be optimally matched to the natural mistletoe lectins. It is also intended that such modified mistletoe lectin can be added to a pharmaceutical composition according to the invention.

The following figures and examples illustrate the invention:

FIG. A: Representation of a mistletoe lectin-I dimer;

FIG. 1: Representation of the (a) nucleic acid sequence (SEQ ID NO: 15) and (b) amino acid sequence (SEQ ID NO: 4) of MLA-I;

FIG. 2: Representation of the (a) nucleic acid sequence (SEQ ID NO: 16) and (b) amino acid sequence (SEQ ID NO: 37) of mistletoe lectin A1;

FIG. 3: Representation of the (a) nucleic acid sequence (SEQ ID NO: 17) and (b) amino acid sequence (SEQ ID NO: 38) of mistletoe lectin A2;

FIG. 4: Representation of (a) the nucleic acid sequence of MLI (SEQ ID NO: 18); wherein the nucleic acid sequence is matched to the codon usage of *Brassica* and (b) the amino acid sequence of mistletoe lectin I (matched) (SEQ ID NO: 4);

FIG. 5: Representation of the nucleic acid sequence of mistletoe lectin A1 (SEQ ID NO: 19), wherein the nucleic acid sequence is matched to the codon usage of *Brassica* and (b) the amino acid sequence of mistletoe lectin A1 (matched) (SEQ ID NO:39);

Figure 6A:
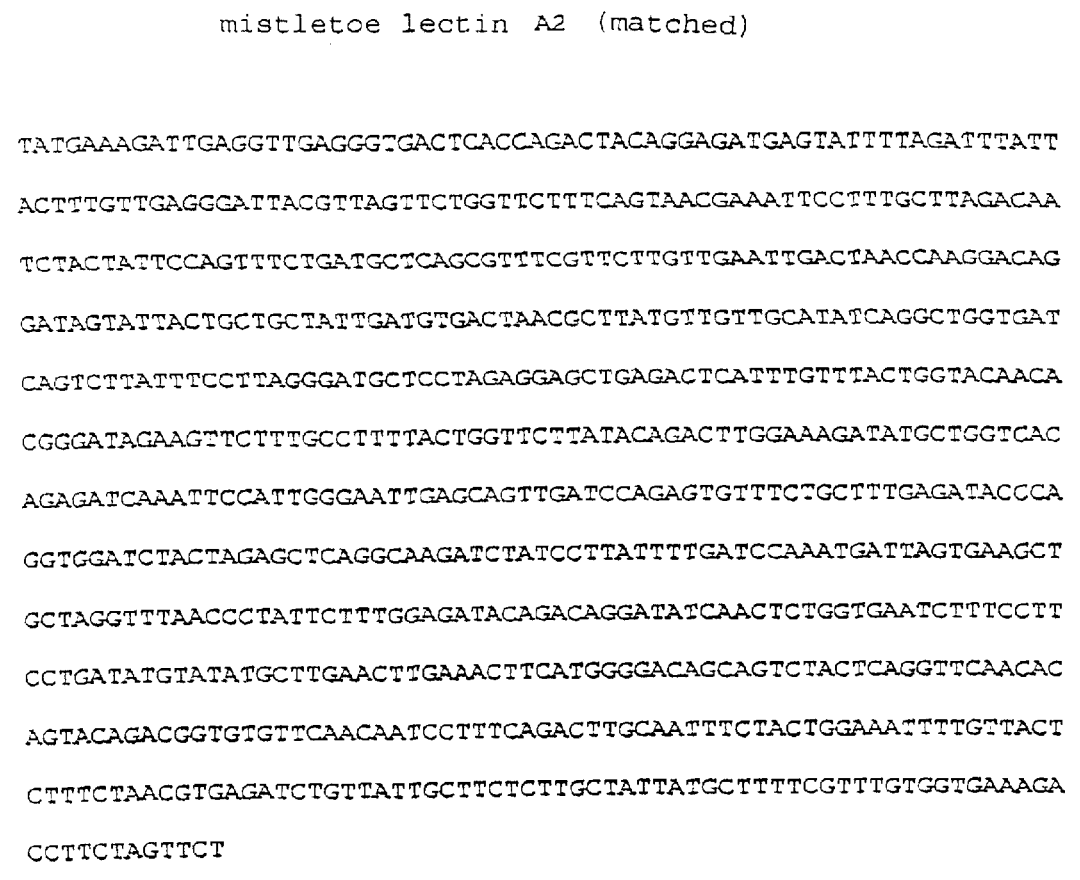

FIG. 6: Representation of (a) the nucleic acid sequence of mistletoe lectin A2 (SEQ ID NO: 20), wherein the nucleic acid sequence is matched to the codon usage of *Brassica* and (b) the amino acid sequence of mistletoe lectin A2 (matched) (SEQ ID NO: 5);

FIG. 7: Representation of the (a) nucleic acid sequence (SEQ ID NO: 21) and (b) amino acid sequence (SEQ ID NO: 6) of mistletoe lectin B;

FIG. 8: Representation of the (a) nucleic acid sequence (SEQ ID NO: 22) and (b) amino acid sequence (SEQ ID NO: 7) of mistletoe lectin B1;

FIG. 9: Representation of the (a) nucleic acid sequence (SEQ ID NO:23) and (b) amino acid sequence (SEQ ID NO: 8) of mistletoe lectin B2;

Figure 10A:
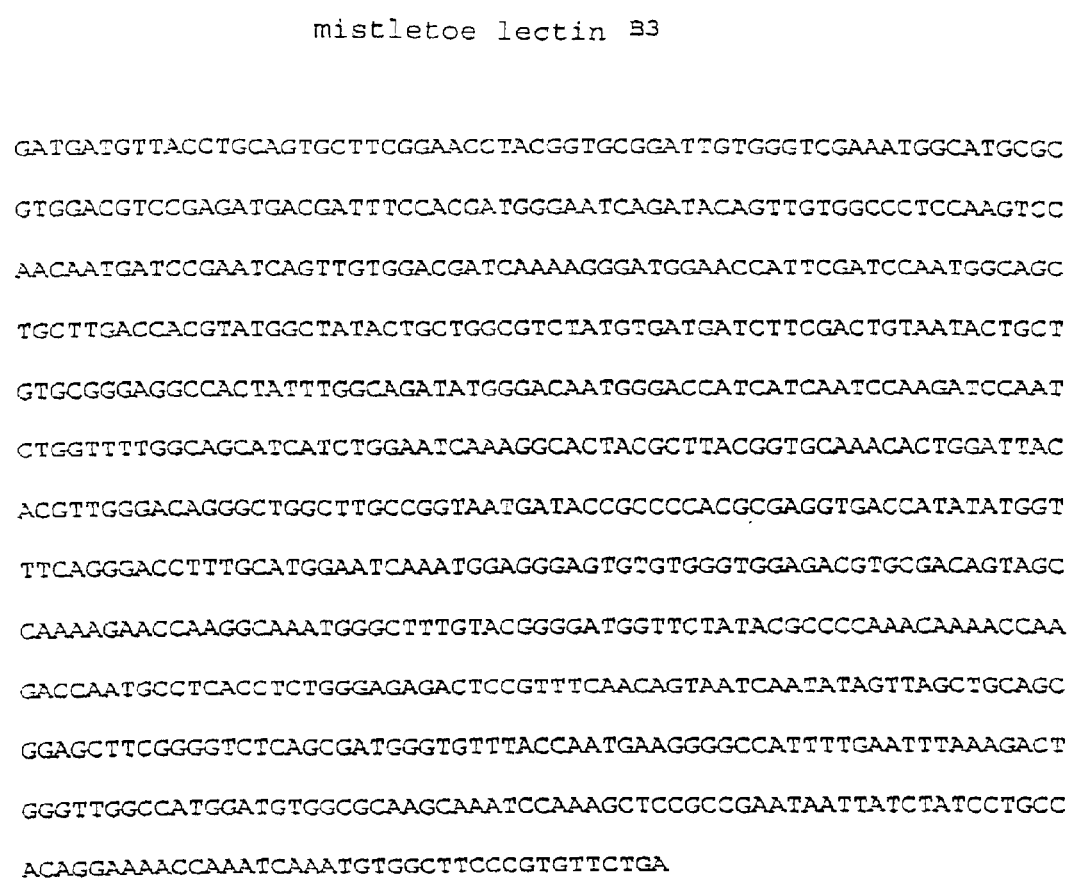

FIG. 10: Representation of the (a) nucleic acid sequence (SEQ ID NO:24) and (b) amino acid sequence (SEQ ID NO: 9) of mistletoe lectin B3;

FIG. 11: Representation of the (a) nucleic acid sequence (SEQ ID NO:25) and (b) amino acid sequence (SEQ ID NO: 10) of mistletoe lectin B4;

FIG. 12: Representation of the (a) nucleic acid sequence (SEQ ID NO:26) and (b) amino acid sequence (SEQ ID NO: 11) of mistletoe lectin B5;

FIG. 13: Representation of (a) the nucleic acid sequence of mistletoe lectin B (SEQ ID NO:27), wherein the nucleic acid sequence is matched to the codon usage of *Brassica* and (b) the amino acid sequence of mistletoe lectin B (matched) (SEQ ID NO: 6);

FIG. 14: Representation of (a) the nucleic acid sequence of mistletoe lectin B1 (SEQ ID NO:28), wherein the nucleic acid sequence is matched to the codon usage of *Brassica* and (b) the amino acid sequence of mistletoe lectin 1 (matched) (SEQ ID NO: 7);

Figure 15A:
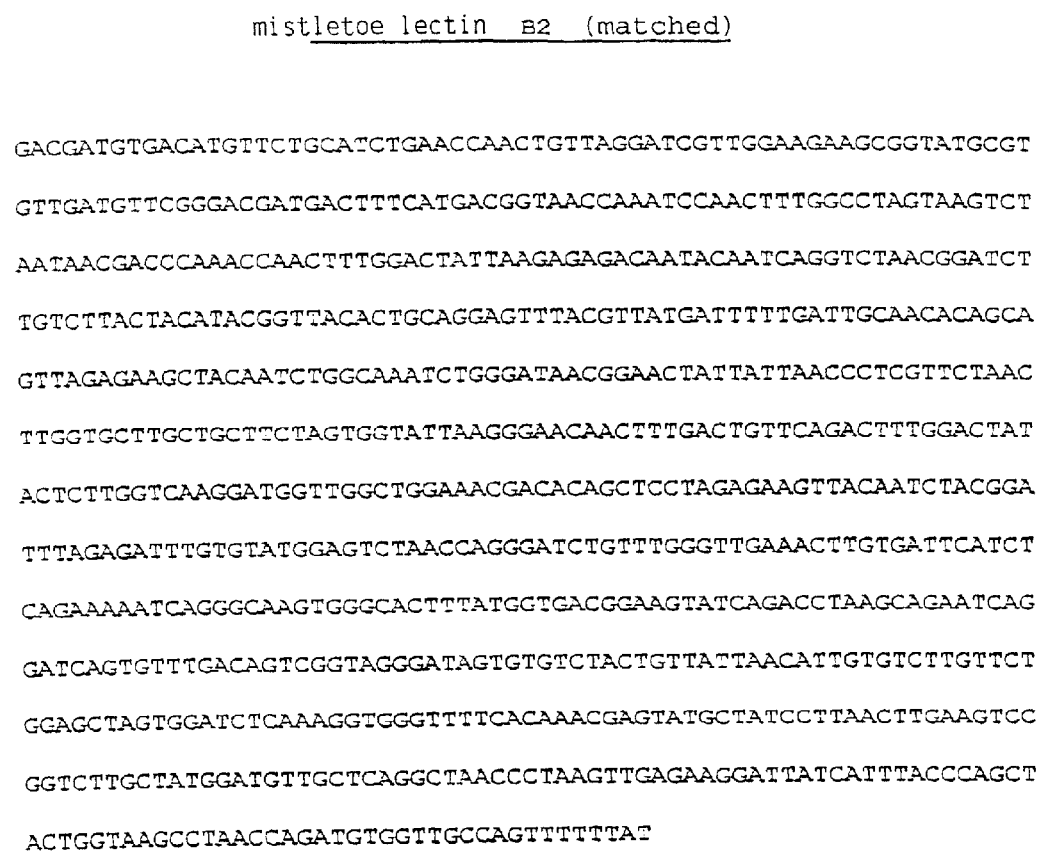
Figure 15B:
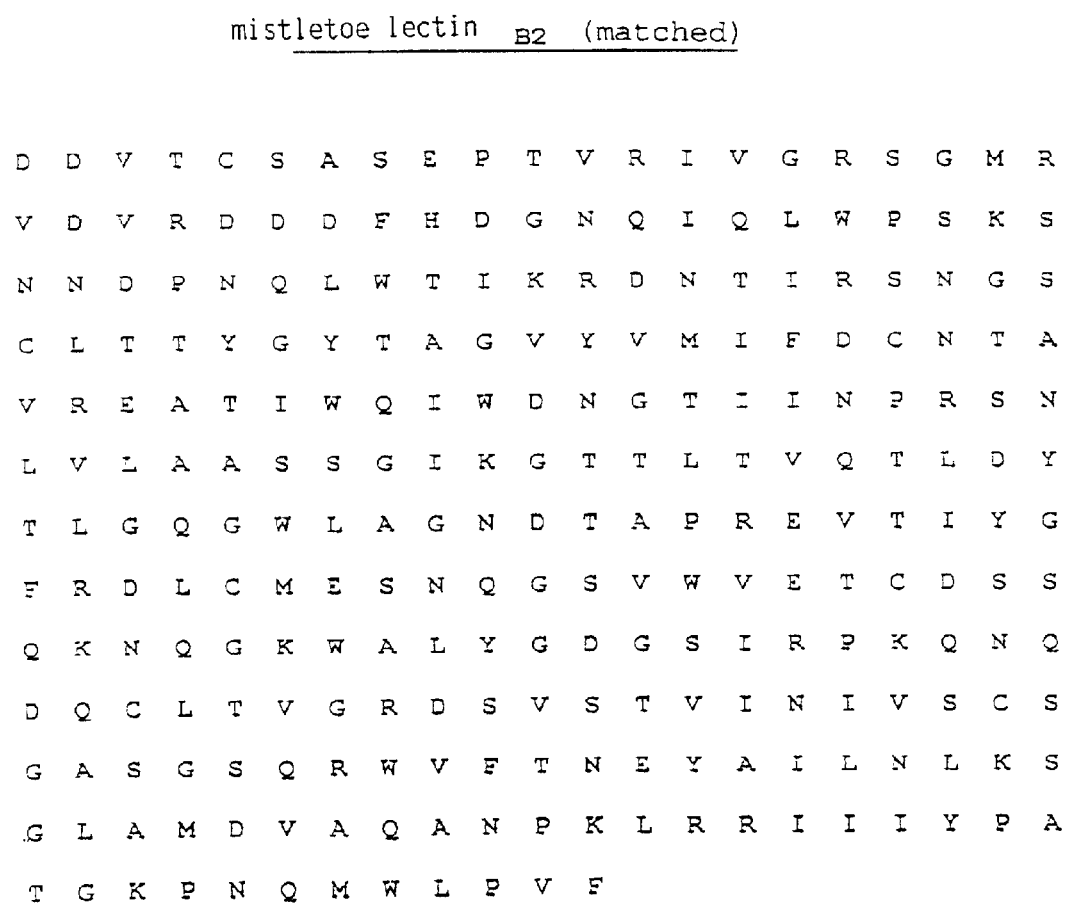

FIG. 15: Representation of (a) the nucleic acid sequence of mistletoe lectin B2 (SEQ ID NO:29), wherein the nucleic acid sequence is matched to the codon usage of *Brassica* and (b) the amino acid sequence of mistletoe lectin B2 (matched) (SEQ ID NO: 8);

FIG. 16: Representation of (a) the nucleic acid sequence of mistletoe lectin B3 (SEQ ID NO:30), wherein the nucleic acid sequence is matched to the codon usage of *Brassica* and (b) the amino acid sequence of mistletoe lectin B3 (matched) (SEQ ID NO: 9);

FIG. 17: Representation of (a) the nucleic acid sequence of mistletoe lectin B4 (SEQ ID NO:31), wherein the nucleic acid sequence is matched to the codon usage of *Brassica* and (b) the amino acid sequence of mistletoe lectin B4 (matched) (SEQ ID NO: 10); and, FIG. 18: Representation of the (a) nucleic acid sequence of mistletoe lectin B5 (SEQ ID NO:32), wherein the nucleic acid sequence is matched to the codon usage of *Brassica* and (b) the amino acid sequence of mistletoe lectin B5 (SEQ ID NO: 11).

EXAMPLE 1

Mistletoe plants of the species *Viscum album L.* spp. *platyspermum* Kell were harvested from poplars growing in Alsace and frozen directly after harvesting. The plant material was crushed in liquid nitrogen in the laboratory and then the DNA from 100 mg of plant material was isolated by the process described in the Qiagen DNeasy Plant Mini-Handbook 09/96.

EXAMPLE 2
PCR Conditions for the Amplification of Mistletoe Lectin-I DNA

For the amplification of genomic mistletoe lectin-I DNA, 100 ng of template DNA, prepared as stated in Example 1, were used in a PCR process with 30 cycles using Taq polymerase (Boehringer Mannheim). 1 µg of primer, $MgCl_2$ (end concentration 2 mM), nucleotide mixture A, T, C, G (end concentration 0.2 mM) and 2.5 units of Taq polymerase were added to the template DNA. The reaction was started as hot-start PCR by a denaturation step of the DNA for 5 minutes at 94° C. In this, the enzyme and the remaining reagents only mixed after a wax barrier between the components had melted. The 30 subsequent cycles are performed under the following conditions:

| Denaturation: | 94° C. | 30 seconds |
|---|---|---|
| Annealing: | 55° C. | 30 seconds |
| Amplification: | 72° C. | 1 minute. |

Following the 30 cycles, a 7-minute elongation reaction at 72° C. was also performed, before the reaction mixture was cooled down to 4° C.

The primers used in the PCR process hybridised with fragments of the genomic DNA coding for MLB chain DNA and had the following sequences:
B1. GTN MGN GAY GAY GAY TTY CA (SEQ ID NO: 33)
B2. AT YTG RTT NGG YTT NCC NGT (SEQ ID NO:34)

The nucleotides are defined in accordance with the IUPAC-IUB code.

The oligonucleotide B1 hybridised to the nucleic acid region that corresponds to amino acids 24 to 30 of the MLB sequence, while the oligonucleotide B2 hybridised to the complementary DNA sequence coding for amino acids 253–258 of MLB.

EXAMPLE 3

In order to determine the flanking 3' and 5' sequences of the DNA amplified in Example 2, the RACE technique was used. 2 µg of RNA template in cDNA synthesis buffer (end concentration: 20 mM Tris-HCl, 8 mM $MgCl_2$, 30 mM KCl, 1 mM dithiothreitol; pH 8.5 (20° C.)) were treated with AMV reverse transcriptase, the deoxynucleotides and the specific primer (see below) and incubated for 60 mins at 65° C. Next, the sample was incubated for 10 mins at 65° C. After the purification of the first cDNA strand, the "tailing" reaction was carried out with 2/5 of the synthesised cDNA with terminal transferase. After the tailing reaction, a PCR was performed with the oligo-dT anchor primer and the specific primer (see above for incubation conditions, except for the annealing temperature, which was lowered to 50° C.). For the determination of the 5' regions of the nucleic acid molecules amplified in Example 2, the oligonucleotide having the following sequence was used:

CAC AGC AGT ATT ACA GTC GAA (SEQ ID NO: 35)

A DNA sequence complementary to this oligonucleotide codes for the amino acid sequence 79–85 of the MLB polypeptide. In order to determine the 3' regions of the amplified nucleic acid molecules, the oligonucleotide having the following sequence was used in a similar experiment:

GTC TAT GTG ATG ATC TTC GAC TGT (SEQ ID NO: 36).

This nucleic acid sequence codes for the amino acid region 74–81 of the MLB polypeptide. For the 3' RACE reaction, the same incubation conditions as for the 5' RACE were used, except for the "tailing" reaction, which is not necessary here because of the polyA tail of the mRNA. In both processes, the oligo-dT anchor primer of the Boehringer Mannheim kit was used.

EXAMPLE 4
Pharmaceutical Composition with Cytotoxic Action

Mistletoe, tobacco and rape cells are transfected with RNA vectors which code for MLA1 and MLA2, the respective cells are harvested after a few days, and the MLA1 and MLA2 proteins purified by affinity chromatography. As gel material, divinylsulphone (DVS)-activated lactose-coupled Sepharose 4B (Pharmacia) is used. By treatment with 0.2 M HCl, the material is activated, i.e. the Sepharose structure is partially hydrolysed and sugar-binding sites to which the lectins can bind are freed. 100 ml of gel material are washed with 0.2 M HCl in a Buchner funnel and suspended in 200 ml of 0.2 M HCl. The hydrolysis of the gel material is effected by 3.5-hour incubation of the suspension at 50° C. in the water-bath. The suspension is washed free of acid with water and then with peptide eluent (0.05 $K_2HPO_4$x $3H_2O$, 0.15 M NaCl, pH 7.0). Then the suspension is degassed, the peptide eluent removed by suction, and the viscous liquid gel material filled into an empty column XK50/30 (3×50 cm, Pharmacia) and packed with peptide eluent pH 7.0 at a flow rate of 2.5 ml/min initially and then 5 ml/min. The column is equilibrated with the same eluent at a flow rate of 1 ml/min. The cell extract obtained from the transfected mistletoe cells is centrifuged and the supernatant loaded onto the column. The separation is performed at a flow rate of 1 ml/min with peptide eluent pH 7.0. The lectins are eluted from the column material with a buffer of 0.2 M lactose in peptide eluent pH 7.0 at a flow rate of 2 ml/min. The elution of the lectin from the column is measured by determination of the absorption at 206 nm. The lectin-containing fractions are collected, frozen and lyophilised. If desired, a further purification step on an HPLC column can be performed. Suitable for this is a Vydac C4 300 A column, which is run at a flow rate of 300 µl/min and a gradient of 20% to 100% B in 60 minutes, where eluent A is 0.17% TFA in water and eluent B is 0.15% TFA in 80% $CH_3CN$ in water. The elution of the mistletoe lectins is detected at a wavelength of 214 nm.

The purified MLA-1 and MLA-2 polypeptides are coupled to a suitable cell recognition molecule. If the cell recognition molecule is a mono- or polyclonal antibody, this can for example be bound to the cytotoxic MLA1 or MLA2 using glutaraldehyde or be directly expressed as chimaeric fusion protein (antibody-MLA) in the appropriate expression system.

EXAMPLE 5

Pharmaceutical Composition

Mistletoe cells are transfected with RNA vectors which code for the mistletoe lectins MLA1 and MLA2 and mistletoe lectins MLB to MLB6. After a few days, the mistletoe lectin monomers or dimers are extracted from the mistletoe cells and purified by processes such as are described in Example 4. The monomers thus obtained can be fused in vitro to heterologous and homologous dimers. In this way, a large number of different combinations of the individual MLA and MLB polypeptides are formed. The heterogeneous mixture of ML-1 dimers and monomers thus produced is lyophilised and used for formulation with a suitable vehicle.

What is claimed is:

1. An isolated mistletoe lectin polypeptide comprising i) the sequence of SEQ ID NO:1, wherein Xaa at position 533 of SEQ ID NO:1 is phenylalanine; or ii) the sequence of SEQ ID NO:40, wherein Xaa at position 534 of SEQ ID NO:40 is phenylalanine.

2. An isolated mistletoe lectin polypeptide, comprising the sequence of SEQ ID NO: 3.

3. An isolated mistletoe lectin polypeptide selected from the group consisting of:

I) a polypeptide comprising the sequence of SEQ ID NO: 6;

II) a polypeptide comprising the sequence of SEQ ID NO: 7;

III) a polypeptide comprising the sequence of SEQ ID NO: 8;

IV) a polypeptide comprising the sequence of SEQ ID NO: 9;

V) a polypeptide comprising the sequence of SEQ ID NO: 10;

VI) a polypeptide comprising the sequence of SEQ ID NO: 11;

VII) a polypeptide comprising the sequence of SEQ ID NO: 4;

VIII) a polypeptide comprising the sequence of SEQ ID NO: 38; and

IX) a polypeptide comprising the sequence of SEQ ID NO: 41.

4. A pharmaceutical composition which contains the polypeptide of claim 1 or claim 3.

5. The pharmaceutical composition of claim 4, further containing a suitable cell recognition molecule which couples to the polypeptide of claim 1 or claim 3, wherein the cell recognition molecule selectively binds to target cells.

6. The pharmaceutical composition of claim 5, wherein the cell recognition molecule is selected from the group consisting of antibody molecules or antibody fragments, cell receptor ligands, peptide hormones or fragments thereof.

* * * * *

UNITED STATES PATENT AND TRADEMARK OFFICE
CERTIFICATE OF CORRECTION

PATENT NO. : 6,927,207 B1
APPLICATION NO. : 09/601667
DATED : August 9, 2005
INVENTOR(S) : Peter Morris et al.

It is certified that error appears in the above-identified patent and that said Letters Patent is hereby corrected as shown below:

Title Page Item (54), "LECTINES" should be -- LECTINS --.

Title Page Item (30), "198 04 210" should be -- 198 04 210.8 --.

<u>In the Specification:</u>

At Column 1, line 1, "LECTINES" should be -- LECTINS --.

Signed and Sealed this

Sixth Day of March, 2007

JON W. DUDAS
*Director of the United States Patent and Trademark Office*

SEQUENCE LISTING

```
<160> NUMBER OF SEQ ID NOS: 41

<210> SEQ ID NO 1
<211> LENGTH: 533
<212> TYPE: PRT
<213> ORGANISM: Artificial Sequence
<220> FEATURE:
<223> OTHER INFORMATION: mistletoe lectin
<220> FEATURE:
<221> NAME/KEY: SITE
<222> LOCATION: 15
<223> OTHER INFORMATION: product= "Xaa is Asp or Glu"
      /label= Xaa1
<220> FEATURE:
<221> NAME/KEY: SITE
<222> LOCATION: 63
<223> OTHER INFORMATION: product= "Xaa is Gly or Gln"
      /label= Xaa2
<220> FEATURE:
<221> NAME/KEY: SITE
<222> LOCATION: 66
<223> OTHER INFORMATION: product= "Xaa is Ile or Val"
      /label= Xaa3
<220> FEATURE:
<221> NAME/KEY: SITE
<222> LOCATION: 75
<223> OTHER INFORMATION: product= "Xaa is Leu or Ala"
      /label= Xaa4
<220> FEATURE:
<221> NAME/KEY: SITE
<222> LOCATION: 107
<223> OTHER INFORMATION: product= "Xaa is missing"
      /label= Xaa5
<220> FEATURE:
<221> NAME/KEY: SITE
<222> LOCATION: 113
<223> OTHER INFORMATION: product= "Xaa is Asn or Thr"
      /label= Xaa6
<220> FEATURE:
<221> NAME/KEY: SITE
<222> LOCATION: 117
<223> OTHER INFORMATION: product= "Xaa is Pro or Thr"
      /label= Xaa7
<220> FEATURE:
<221> NAME/KEY: SITE
<222> LOCATION: 134
<223> OTHER INFORMATION: product= "Xaa is Asp or Glu"
      /label= Xaa8
<220> FEATURE:
<221> NAME/KEY: SITE
<222> LOCATION: 141
<223> OTHER INFORMATION: product= "Xaa is Ser or Thr"
      /label= Xaa9
```

```
<220> FEATURE:
<221> NAME/KEY: SITE
<222> LOCATION: 145
<223> OTHER INFORMATION: product= "Xaa is Phe or Tyr"
      /label= Xaa10
<220> FEATURE:
<221> NAME/KEY: SITE
<222> LOCATION: 152
<223> OTHER INFORMATION: product= "Xaa is Thr or Ala"
      /label= Xaa11
<220> FEATURE:
<221> NAME/KEY: SITE
<222> LOCATION: 177
<223> OTHER INFORMATION: product= "Xaa is Ala or Tyr"
      /label= Xaa12
<220> FEATURE:
<221> NAME/KEY: SITE
<222> LOCATION: 180
<223> OTHER INFORMATION: product= "Xaa is Tyr or Asp"
      /label= Xaa13
<220> FEATURE:
<221> NAME/KEY: SITE
<222> LOCATION: 185
<223> OTHER INFORMATION: product= "Xaa is Ala or Glu"
      /label= Xaa14
<220> FEATURE:
<221> NAME/KEY: SITE
<222> LOCATION: 191
<223> OTHER INFORMATION: product= "Xaa is Val or Met"
      /label= Xaa15
<220> FEATURE:
<221> NAME/KEY: SITE
<222> LOCATION: 219
<223> OTHER INFORMATION: product= "Xaa is Ile or Phe"
      /label= Xaa16
<220> FEATURE:
<221> NAME/KEY: SITE
<222> LOCATION: 224
<223> OTHER INFORMATION: product= "Xaa is Pro or Ser"
      /label= Xaa17
<220> FEATURE:
<221> NAME/KEY: SITE
<222> LOCATION: 225
<223> OTHER INFORMATION: product= "Xaa is Pro or Thr"
      /label= Xaa18
<220> FEATURE:
<221> NAME/KEY: SITE
<222> LOCATION: 232
<223> OTHER INFORMATION: product= "Xaa is Thr or Ser"
      /label= Xaa19
<220> FEATURE:
<221> NAME/KEY: SITE
<222> LOCATION: 236
<223> OTHER INFORMATION: product= "Xaa is Asp or Ser"
      /label= Xaa20
<220> FEATURE:
<221> NAME/KEY: SITE
<222> LOCATION: 287
<223> OTHER INFORMATION: product= "Xaa is Asn or Ser"
      /label= Xaa21
<220> FEATURE:
<221> NAME/KEY: SITE
<222> LOCATION: 290
<223> OTHER INFORMATION: product= "Xaa is Cys or Arg"
      /label= Xaa22
<220> FEATURE:
<221> NAME/KEY: SITE
<222> LOCATION: 325
<223> OTHER INFORMATION: product= "Xaa is Gly or Asn"
      /label= Xaa23
<220> FEATURE:
<221> NAME/KEY: SITE
<222> LOCATION: 364
<223> OTHER INFORMATION: product= "Xaa is Gly or Asp"
      /label= Xaa24
```

-continued

```
<220> FEATURE:
<221> NAME/KEY: SITE
<222> LOCATION: 426
<223> OTHER INFORMATION: product= "Xaa is Gly or Gln"
      /label= Xaa25
<220> FEATURE:
<221> NAME/KEY: SITE
<222> LOCATION: 435
<223> OTHER INFORMATION: product= "Xaa is Val or Asp"
      /label= Xaa26
<220> FEATURE:
<221> NAME/KEY: SITE
<222> LOCATION: 439
<223> OTHER INFORMATION: product= "Xaa is Gln or Lys"
      /label= Xaa27
<220> FEATURE:
<221> NAME/KEY: SITE
<222> LOCATION: 442
<223> OTHER INFORMATION: product= "Xaa is Gly or missing"
      /label= Xaa28
<220> FEATURE:
<221> NAME/KEY: SITE
<222> LOCATION: 443
<223> OTHER INFORMATION: product= "Xaa is Arg or Lys"
      /label= Xaa29
<220> FEATURE:
<221> NAME/KEY: SITE
<222> LOCATION: 464
<223> OTHER INFORMATION: product= "Xaa is Cys or Ser or Val"
      /label= Xaa30
<220> FEATURE:
<221> NAME/KEY: SITE
<222> LOCATION: 480
<223> OTHER INFORMATION: product= "Xaa is Ala or Gly"
      /label= Xaa
<220> FEATURE:
<221> NAME/KEY: SITE
<222> LOCATION: 481
<223> OTHER INFORMATION: product= "Xaa is Gly or Ala"
      /label= Xaa32
<220> FEATURE:
<221> NAME/KEY: SITE
<222> LOCATION: 483
<223> OTHER INFORMATION: product= "Xaa is Ser or Gly"
      /label= Xaa33
<220> FEATURE:
<221> NAME/KEY: SITE
<222> LOCATION: 484
<223> OTHER INFORMATION: product= "Xaa is Gly or Ser"
      /label= Xaa34
<220> FEATURE:
<221> NAME/KEY: SITE
<222> LOCATION: 493
<223> OTHER INFORMATION: product= "Xaa is Gly or Tyr"
      /label= Xaa35
<220> FEATURE:
<221> NAME/KEY: SITE
<222> LOCATION: 500
<223> OTHER INFORMATION: product= "Xaa is Asn or Ser or Thr or Lys"
      /label= Xaa36
<220> FEATURE:
<221> NAME/KEY: SITE
<222> LOCATION: 501
<223> OTHER INFORMATION: product= "Xaa is Ser or Gly"
      /label= Xaa37
<220> FEATURE:
<221> NAME/KEY: SITE
<222> LOCATION: 502
<223> OTHER INFORMATION: product= "Xaa is Leu or Pro"
      /label= Xaa38
<220> FEATURE:
<221> NAME/KEY: SITE
<222> LOCATION: 503
<223> OTHER INFORMATION: product= "Xaa is Ala or Met"
      /label= Xaa39
```

```
<220> FEATURE:
<221> NAME/KEY: SITE
<222> LOCATION: 504
<223> OTHER INFORMATION: product= "Xaa is Met or Val"
      /label= Xaa40
<220> FEATURE:
<221> NAME/KEY: SITE
<222> LOCATION: 533
<223> OTHER INFORMATION: product= "Xaa is Pro or Phe"
      /label= Xaa41

<400> SEQUENCE: 1

Tyr Glu Arg Leu Arg Leu Arg Val Thr His Gln Thr Thr Gly Xaa Glu
1               5                   10                  15

Tyr Phe Arg Phe Ile Thr Leu Leu Arg Asp Tyr Val Ser Ser Gly Ser
            20                  25                  30

Phe Ser Asn Glu Ile Pro Leu Leu Arg Gln Ser Thr Ile Pro Val Ser
        35                  40                  45

Asp Ala Gln Arg Phe Val Leu Val Glu Leu Thr Asn Gln Gly Xaa Asp
    50                  55                  60

Ser Xaa Thr Ala Ala Ile Asp Val Thr Asn Xaa Tyr Val Val Ala Tyr
65                  70                  75                  80

Gln Ala Gly Asp Gln Ser Tyr Phe Leu Arg Asp Ala Pro Arg Gly Ala
                85                  90                  95

Glu Thr His Leu Phe Thr Gly Thr Thr Arg Xaa Ser Ser Leu Pro Phe
            100                 105                 110

Xaa Gly Ser Tyr Xaa Asp Leu Glu Arg Tyr Ala Gly His Arg Asp Gln
        115                 120                 125

Ile Pro Leu Gly Ile Xaa Gln Leu Ile Gln Ser Val Xaa Ala Leu Arg
    130                 135                 140

Xaa Pro Gly Gly Ser Thr Arg Xaa Gln Ala Arg Ser Ile Leu Ile Leu
145                 150                 155                 160

Ile Gln Met Ile Ser Glu Ala Ala Arg Phe Asn Pro Ile Leu Trp Arg
                165                 170                 175

Xaa Arg Gln Xaa Ile Asn Ser Gly Xaa Ser Phe Leu Pro Asp Xaa Tyr
            180                 185                 190

Met Leu Glu Leu Glu Thr Ser Trp Gly Gln Gln Ser Thr Gln Val Gln
        195                 200                 205

His Ser Thr Asp Gly Val Phe Asn Asn Pro Xaa Arg Leu Ala Ile Xaa
    210                 215                 220

Xaa Gly Asn Phe Val Thr Leu Xaa Asn Val Arg Xaa Val Ile Ala Ser
225                 230                 235                 240

Leu Ala Ile Met Leu Phe Val Cys Gly Glu Arg Pro Ser Ser Ser Asp
                245                 250                 255

Val Arg Tyr Trp Pro Leu Val Ile Arg Pro Val Ile Ala Asp Asp Val
            260                 265                 270

Thr Cys Ser Ala Ser Glu Pro Thr Val Arg Ile Val Gly Arg Xaa Gly
        275                 280                 285

Met Xaa Val Asp Val Arg Asp Asp Phe His Asp Gly Asn Gln Ile
    290                 295                 300

Gln Leu Trp Pro Ser Lys Ser Asn Asn Asp Pro Asn Gln Leu Trp Thr
305                 310                 315                 320

Ile Lys Arg Asp Xaa Thr Ile Arg Ser Asn Gly Ser Cys Leu Thr Thr
                325                 330                 335

Tyr Gly Tyr Thr Ala Gly Val Tyr Val Met Ile Phe Asp Cys Asn Thr
            340                 345                 350
```

```
Ala Val Arg Glu Ala Thr Ile Trp Gln Ile Trp Xaa Asn Gly Thr Ile
        355                 360                 365
Ile Asn Pro Arg Ser Asn Leu Val Leu Ala Ala Ser Ser Gly Ile Lys
    370                 375                 380
Gly Thr Thr Leu Thr Val Gln Thr Leu Asp Tyr Thr Leu Gly Gln Gly
385                 390                 395                 400
Trp Leu Ala Gly Asn Asp Thr Ala Pro Arg Glu Val Thr Ile Tyr Gly
                405                 410                 415
Phe Arg Asp Leu Cys Met Glu Ser Asn Xaa Gly Ser Val Trp Val Glu
            420                 425                 430
Thr Cys Xaa Ser Ser Gln Xaa Asn Gln Xaa Xaa Trp Ala Leu Tyr Gly
        435                 440                 445
Asp Gly Ser Ile Arg Pro Lys Gln Asn Gln Asp Gln Cys Leu Thr Xaa
    450                 455                 460
Gly Arg Asp Ser Val Ser Thr Val Ile Asn Ile Val Ser Cys Ser Xaa
465                 470                 475                 480
Xaa Ser Xaa Xaa Gln Arg Trp Val Phe Thr Asn Glu Xaa Ala Ile Leu
                485                 490                 495
Asn Leu Lys Xaa Xaa Xaa Xaa Asp Val Ala Gln Ala Asn Pro Lys
        500                 505                 510
Leu Arg Arg Ile Ile Ile Tyr Pro Ala Thr Gly Lys Pro Asn Gln Met
        515                 520                 525
Trp Leu Pro Val Xaa
        530

<210> SEQ ID NO 2
<211> LENGTH: 255
<212> TYPE: PRT
<213> ORGANISM: Artificial Sequence
<220> FEATURE:
<223> OTHER INFORMATION: MLA-chain
<220> FEATURE:
<221> NAME/KEY: SITE
<222> LOCATION: 15
<223> OTHER INFORMATION: product= "Xaa is Asp or Glu"
      /label= Xaa1
<220> FEATURE:
<221> NAME/KEY: SITE
<222> LOCATION: 63
<223> OTHER INFORMATION: product= "Xaa is Gly or Gln"
      /label= Xaa2
<220> FEATURE:
<221> NAME/KEY: SITE
<222> LOCATION: 66
<223> OTHER INFORMATION: product= "Xaa is Ile or Val"
      /label= Xaa3
<220> FEATURE:
<221> NAME/KEY: SITE
<222> LOCATION: 75
<223> OTHER INFORMATION: product= "Xaa is Leu or Ala"
      /label= Xaa4
<220> FEATURE:
<221> NAME/KEY: SITE
<222> LOCATION: 107
<223> OTHER INFORMATION: product= "Xaa is missing"
      /label= Xaa5
<220> FEATURE:
<221> NAME/KEY: SITE
<222> LOCATION: 113
<223> OTHER INFORMATION: product= "Xaa is Asn or Thr"
      /label= Xaa6
<220> FEATURE:
<221> NAME/KEY: SITE
<222> LOCATION: 117
<223> OTHER INFORMATION: product= "Xaa is Pro or Thr"
      /label= Xaa7
```

```
<220> FEATURE:
<221> NAME/KEY: SITE
<222> LOCATION: 134
<223> OTHER INFORMATION: product= "Xaa is Asp or Glu"
      /label= Xaa8
<220> FEATURE:
<221> NAME/KEY: SITE
<222> LOCATION: 141
<223> OTHER INFORMATION: product= "Xaa is Ser or Thr"
      /label= Xaa9
<220> FEATURE:
<221> NAME/KEY: SITE
<222> LOCATION: 145
<223> OTHER INFORMATION: product= "Xaa is Phe or Tyr"
      /label= Xaa10
<220> FEATURE:
<221> NAME/KEY: SITE
<222> LOCATION: 152
<223> OTHER INFORMATION: product= "Xaa is Thr or Ala"
      /label= Xaa11
<220> FEATURE:
<221> NAME/KEY: SITE
<222> LOCATION: 177
<223> OTHER INFORMATION: product= "Xaa is Ala or Tyr"
      /label= Xaa12
<220> FEATURE:
<221> NAME/KEY: SITE
<222> LOCATION: 180
<223> OTHER INFORMATION: product= "Xaa is Tyr or Asp"
      /label= Xaa13
<220> FEATURE:
<221> NAME/KEY: SITE
<222> LOCATION: 185
<223> OTHER INFORMATION: product= "Xaa is Ala or Glu"
      /label= Xaa14
<220> FEATURE:
<221> NAME/KEY: SITE
<222> LOCATION: 191
<223> OTHER INFORMATION: product= "Xaa is Val or Met"
      /label= Xaa15
<220> FEATURE:
<221> NAME/KEY: SITE
<222> LOCATION: 219
<223> OTHER INFORMATION: product= "Xaa is Ile or Phe"
      /label= Xaa16
<220> FEATURE:
<221> NAME/KEY: SITE
<222> LOCATION: 224
<223> OTHER INFORMATION: product= "Xaa is Pro or Ser"
      /label= Xaa17
<220> FEATURE:
<221> NAME/KEY: SITE
<222> LOCATION: 225
<223> OTHER INFORMATION: product= "Xaa is Pro or Thr"
      /label= Xaa18
<220> FEATURE:
<221> NAME/KEY: SITE
<222> LOCATION: 232
<223> OTHER INFORMATION: product= "Xaa is Thr or Ser"
      /label= Xaa19
<220> FEATURE:
<221> NAME/KEY: SITE
<222> LOCATION: 236
<223> OTHER INFORMATION: product= "Xaa is Asp or Ser"
      /label= Xaa20

<400> SEQUENCE: 2

Tyr Glu Arg Leu Arg Leu Arg Val Thr His Gln Thr Thr Gly Xaa Glu
1               5                   10                  15

Tyr Phe Arg Phe Ile Thr Leu Leu Arg Asp Tyr Val Ser Ser Gly Ser
            20                  25                  30

Phe Ser Asn Glu Ile Pro Leu Leu Arg Gln Ser Thr Ile Pro Val Ser
        35                  40                  45

Asp Ala Gln Arg Phe Val Leu Val Glu Leu Thr Asn Gln Gly Xaa Asp
50                  55                  60
```

```
Ser Xaa Thr Ala Ala Ile Asp Val Thr Asn Xaa Tyr Val Val Ala Tyr
 65              70                  75                  80

Gln Ala Gly Asp Gln Ser Tyr Phe Leu Arg Asp Ala Pro Arg Gly Ala
                 85                  90                  95

Glu Thr His Leu Phe Thr Gly Thr Arg Xaa Ser Ser Leu Pro Phe
            100                 105                 110

Xaa Gly Ser Tyr Xaa Asp Leu Glu Arg Tyr Ala Gly His Arg Asp Gln
            115                 120                 125

Ile Pro Leu Gly Ile Xaa Gln Leu Ile Gln Ser Val Xaa Ala Leu Arg
        130                 135                 140

Xaa Pro Gly Gly Ser Thr Arg Xaa Gln Ala Arg Ser Ile Leu Ile Leu
145                 150                 155                 160

Ile Gln Met Ile Ser Glu Ala Ala Arg Phe Asn Pro Ile Leu Trp Arg
                165                 170                 175

Xaa Arg Gln Xaa Ile Asn Ser Gly Xaa Ser Phe Leu Pro Asp Xaa Tyr
            180                 185                 190

Met Leu Glu Leu Glu Thr Ser Trp Gly Gln Gln Ser Thr Gln Val Gln
            195                 200                 205

His Ser Thr Asp Gly Val Phe Asn Asn Pro Xaa Arg Leu Ala Ile Xaa
        210                 215                 220

Xaa Gly Asn Phe Val Thr Leu Xaa Asn Val Arg Xaa Val Ile Ala Ser
225                 230                 235                 240

Leu Ala Ile Met Leu Phe Val Cys Gly Glu Arg Pro Ser Ser Ser
                245                 250                 255

<210> SEQ ID NO 3
<211> LENGTH: 264
<212> TYPE: PRT
<213> ORGANISM: Artificial Sequence
<220> FEATURE:
<223> OTHER INFORMATION: MLB-chain
<220> FEATURE:
<221> NAME/KEY: SITE
<222> LOCATION: 18
<223> OTHER INFORMATION: product= "Xaa is Asn or Ser"
     /label= Xaa1
<220> FEATURE:
<221> NAME/KEY: SITE
<222> LOCATION: 21
<223> OTHER INFORMATION: product= "Xaa is Cys or Arg"
     /label= X2
<220> FEATURE:
<221> NAME/KEY: SITE
<222> LOCATION: 56
<223> OTHER INFORMATION: product= "Xaa is Gly or Asn"
     /label= Xaa3
<220> FEATURE:
<221> NAME/KEY: SITE
<222> LOCATION: 95
<223> OTHER INFORMATION: product= "Xaa is Gly or Asp"
     /label= Xaa4
<220> FEATURE:
<221> NAME/KEY: SITE
<222> LOCATION: 157
<223> OTHER INFORMATION: product= "Xaa is Gly or Gln"
     /label= Xaa5
<220> FEATURE:
<221> NAME/KEY: SITE
<222> LOCATION: 166
<223> OTHER INFORMATION: product= "Xaa is Val or Asp"
     /label= Xaa6
<220> FEATURE:
<221> NAME/KEY: SITE
<222> LOCATION: 170
<223> OTHER INFORMATION: product= "Xaa is Gln or Lys"
     /label= Xaa7
```

-continued

```
<220> FEATURE:
<221> NAME/KEY: SITE
<222> LOCATION: 173
<223> OTHER INFORMATION: product= "Xaa is Gly or missing"
      /label= Xaa8
<220> FEATURE:
<221> NAME/KEY: SITE
<222> LOCATION: 174
<223> OTHER INFORMATION: product= "Xaa is Arg or Lys"
      /label= Xaa9
<220> FEATURE:
<221> NAME/KEY: SITE
<222> LOCATION: 195
<223> OTHER INFORMATION: product= "Xaa is Cys or Ser or Val"
      /label= Xaa10
<220> FEATURE:
<221> NAME/KEY: SITE
<222> LOCATION: 211
<223> OTHER INFORMATION: product= "Xaa is Ala or Gly"
      /label= Xaa11
<220> FEATURE:
<221> NAME/KEY: SITE
<222> LOCATION: 212
<223> OTHER INFORMATION: product= "Xaa is Gly or Ala"
      /label= Xaa12
<220> FEATURE:
<221> NAME/KEY: SITE
<222> LOCATION: 214
<223> OTHER INFORMATION: product= "Xaa is Ser or Gly"
      /label= Xaa13
<220> FEATURE:
<221> NAME/KEY: SITE
<222> LOCATION: 215
<223> OTHER INFORMATION: product= "Xaa is Gly or Ser"
      /label= Xaa14
<220> FEATURE:
<221> NAME/KEY: SITE
<222> LOCATION: 224
<223> OTHER INFORMATION: product= "Xaa is Gly or Tyr"
      /label= Xaa15
<220> FEATURE:
<221> NAME/KEY: SITE
<222> LOCATION: 231
<223> OTHER INFORMATION: product= "Xaa is Asn or Ser or Thr or Lys"
      /label= Xaa16
<220> FEATURE:
<221> NAME/KEY: SITE
<222> LOCATION: 232
<223> OTHER INFORMATION: product= "Xaa is Ser or Gly"
      /label= Xaa17
<220> FEATURE:
<221> NAME/KEY: SITE
<222> LOCATION: 233
<223> OTHER INFORMATION: product= "Xaa is Leu or Pro"
      /label= Xaa17
<220> FEATURE:
<221> NAME/KEY: SITE
<222> LOCATION: 234
<223> OTHER INFORMATION: product= "Xaa is Ala or Met"
      /label= Xaa19
<220> FEATURE:
<221> NAME/KEY: SITE
<222> LOCATION: 235
<223> OTHER INFORMATION: product= "Xaa is Met or Val"
      /label= Xaa20
<220> FEATURE:
<221> NAME/KEY: SITE
<222> LOCATION: 264
<223> OTHER INFORMATION: product= "Xaa is Pro or Phe"
      /label= Xaa21

<400> SEQUENCE: 3

Asp Asp Val Thr Cys Ser Ala Ser Glu Pro Thr Val Arg Ile Val Gly
1               5                   10                  15

Arg Xaa Gly Met Xaa Val Asp Val Arg Asp Asp Phe His Asp Gly
            20                  25                  30
```

```
Asn Gln Ile Gln Leu Trp Pro Ser Lys Ser Asn Asn Asp Pro Asn Gln
             35                  40                  45

Leu Trp Thr Ile Lys Arg Asp Xaa Thr Ile Arg Ser Asn Gly Ser Cys
 50                  55                  60

Leu Thr Thr Tyr Gly Tyr Thr Ala Gly Val Tyr Val Met Ile Phe Asp
 65                  70                  75                  80

Cys Asn Thr Ala Val Arg Glu Ala Thr Ile Trp Gln Ile Trp Xaa Asn
                 85                  90                  95

Gly Thr Ile Ile Asn Pro Arg Ser Asn Leu Val Leu Ala Ala Ser Ser
                100                 105                 110

Gly Ile Lys Gly Thr Thr Leu Thr Val Gln Thr Leu Asp Tyr Thr Leu
            115                 120                 125

Gly Gln Gly Trp Leu Ala Gly Asn Asp Thr Ala Pro Arg Glu Val Thr
        130                 135                 140

Ile Tyr Gly Phe Arg Asp Leu Cys Met Glu Ser Asn Xaa Gly Ser Val
145                 150                 155                 160

Trp Val Glu Thr Cys Xaa Ser Ser Gln Xaa Asn Gln Xaa Xaa Trp Ala
                165                 170                 175

Leu Tyr Gly Asp Gly Ser Ile Arg Pro Lys Gln Asn Gln Asp Gln Cys
            180                 185                 190

Leu Thr Xaa Gly Arg Asp Ser Val Ser Thr Val Ile Asn Ile Val Ser
        195                 200                 205

Cys Ser Xaa Xaa Ser Xaa Xaa Gln Arg Trp Val Phe Thr Asn Glu Xaa
    210                 215                 220

Ala Ile Leu Asn Leu Lys Xaa Xaa Xaa Xaa Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Xaa
            260

<210> SEQ ID NO 4
<211> LENGTH: 531
<212> TYPE: PRT
<213> ORGANISM: Artificial Sequence
<220> FEATURE:
<223> OTHER INFORMATION: MLI match

<400> SEQUENCE: 4

Tyr Glu Arg Leu Arg Leu Arg Val Thr His Gln Thr Thr Gly Glu Glu
 1               5                  10                  15

Tyr Phe Arg Phe Ile Thr Leu Leu Arg Asp Tyr Val Ser Ser Gly Ser
                20                  25                  30

Phe Ser Asn Glu Ile Pro Leu Leu Arg Gln Ser Thr Ile Pro Val Ser
             35                  40                  45

Asp Ala Gln Arg Phe Val Leu Val Glu Leu Thr Asn Gln Gly Gly Asp
 50                  55                  60

Ser Ile Thr Ala Ala Ile Asp Val Th

```
Pro Leu Gly Ile Asp Gln Leu Ile Gln Ser Val Thr Ala Leu Arg Phe
130                 135                 140

Pro Gly Gly Ser Thr Arg Thr Gln Ala Arg Ser Ile Leu Ile Leu Ile
145                 150                 155                 160

Gln Met Ile Ser Glu Ala Ala Arg Phe Asn Pro Ile Leu Trp Arg Ala
                165                 170                 175

Arg Gln Tyr Ile Asn Ser Gly Ala Ser Phe Leu Pro Asp Val Tyr Met
                180                 185                 190

Leu Glu Leu Glu Thr Ser Trp Gly Gln Gln Ser Thr Gln Val Gln His
                195                 200                 205

Ser Thr Asp Gly Val Phe Asn Asn Pro Ile Arg Leu Ala Ile Pro Pro
210                 215                 220

Gly Asn Phe Val Thr Leu Thr Asn Val Arg Asp Val Ile Ala Ser Leu
225                 230                 235                 240

Ala Ile Met Leu Phe Val Cys Gly Glu Arg Pro Ser Ser Asp Val
                245                 250                 255

Arg Tyr Trp Pro Leu Val Ile Arg Pro Val Ile Ala Asp Asp Val Thr
                260                 265                 270

Cys Ser Ala Ser Glu Pro Thr Val Arg Ile Val Gly Arg Asn Gly Met
                275                 280                 285

Cys Val Asp Val Arg Asp Asp Phe His Asp Gly Asn Gln Ile Gln
290                 295                 300

Leu Trp Pro Ser Lys Ser Asn Asn Asp Pro Asn Gln Leu Trp Thr Ile
305                 310                 315                 320

Lys Arg Asp Gly Thr Ile Arg Ser Asn Gly Ser Cys Leu Thr Thr Tyr
                325                 330                 335

Gly Tyr Thr Ala Gly Val Tyr Val Met Ile Phe Asp Cys Asn Thr Ala
                340                 345                 350

Val Arg Glu Ala Thr Ile Trp Gln Ile Trp Gly Asn Gly Thr Ile Ile
                355                 360                 365

Asn Pro Arg Ser Asn Leu Val Leu Ala Ala Ser Ser Gly Ile Lys Gly
370                 375                 380

Thr Thr Leu Thr Val Gln Thr Leu Asp Tyr Thr Leu Gly Gln Gly Trp
385                 390                 395                 400

Leu Ala Gly Asn Asp Thr Ala Pro Arg Glu Val Thr Ile Tyr Gly Phe
                405                 410                 415

Arg Asp Leu Cys Met Glu Ser Asn Gly Gly Ser Val Trp Val Glu Thr
                420                 425                 430

Cys Val Ser Ser Gln Gln Asn Gln Arg Trp Ala Leu Tyr Gly Asp Gly
                435                 440                 445

Ser Ile Arg Pro Lys Gln Asn Gln Asp Gln Cys Leu Thr Cys Gly Arg
                450                 455                 460

Asp Ser Val Ser Thr Val Ile Asn Ile Val Ser Cys Ser Ala Gly Ser
465                 470                 475                 480

Ser Gly Gln Arg Trp Val Phe Thr Asn Glu Gly Ala Ile Leu Asn Leu
                485                 490                 495

Lys Asn Gly Leu Ala Met Asp Val Ala Gln Ala Asn Pro Lys Leu Arg
                500                 505                 510

Arg Ile Ile Ile Tyr Pro Ala Thr Gly Lys Pro Asn Gln Met Trp Leu
                515                 520                 525

Pro Val Pro
530
```

```
<210> SEQ ID NO 5
<211> LENGTH: 256
<212> TYPE: PRT
<213> ORGANISM: Artificial Sequence
<220> FEATURE:
<223> OTHER INFORMATION: Lectin A2

<400> SEQUENCE: 5

Tyr Glu Arg Leu Arg Leu Arg Val Thr His Gln Thr Thr Gly Asp Glu
1               5                   10                  15

Tyr Phe Arg Phe Ile Thr Leu Leu Arg Asp Tyr Val Ser Ser Gly Ser
            20                  25                  30

Phe Ser Asn Glu Ile Pro Leu Leu Arg Gln Ser Thr Ile Pro Val Ser
        35                  40                  45

Asp Ala Gln Arg Phe Val Leu Val Glu Leu Thr Asn Gln Gly Gln Asp
    50                  55                  60

Ser Ile Thr Ala Ala Ile Asp Val Thr Asn Ala Tyr Val Val Ala Tyr
65                  70                  75                  80

Gln Ala Gly Asp Gln Ser Tyr Phe Leu Arg Asp Ala Pro Arg Gly Ala
                85                  90                  95

Glu Thr His Leu Phe Thr Gly Thr Thr Arg Asp Arg Ser Ser Leu Pro
            100                 105                 110

Phe Thr Gly Ser Tyr Thr Asp Leu Glu Arg Tyr Ala Gly His Arg Asp
        115                 120                 125

Gln Ile Pro Leu Gly Ile Glu Gln Leu Ile Gln Ser Val Ser Ala Leu
    130                 135                 140

Arg Tyr Pro Gly Gly Ser Thr Arg Ala Gln Ala Arg Ser Ile Leu Ile
145                 150                 155                 160

Leu Ile Gln Met Ile Ser Glu Ala Ala Arg Phe Asn Pro Ile Leu Trp
                165                 170                 175

Arg Tyr Arg Gln Asp Ile Asn Ser Gly Glu Ser Phe Leu Pro Asp Met
            180                 185                 190

Tyr Met Leu Glu Leu Glu Thr Ser Trp Gly Gln Gln Ser Thr Gln Val
        195                 200                 205

Gln His Ser Thr Asp Gly Val Phe Asn Asn Pro Phe Arg Leu Ala Ile
    210                 215                 220

Ser Thr Gly Asn Phe Val Thr Leu Ser Asn Val Arg Ser Val Ile Ala
225                 230                 235                 240

Ser Leu Ala Ile Met Leu Phe Val Cys Gly Glu Arg Pro Ser Ser Ser
                245                 250                 255

<210> SEQ ID NO 6
<211> LENGTH: 263
<212> TYPE: PRT
<213> ORGANISM: Artificial Sequence
<220> FEATURE:
<223> OTHER INFORMATION: mistletoe lectin B

<400> SEQUENCE: 6

Asp Asp Val Thr Cys Ser Ala Ser Glu P

-continued

```
Leu Thr Thr Tyr Gly Tyr Thr Ala Gly Val Tyr Val Met Ile Phe Asp
 65                  70                  75                  80

Cys Asn Thr Ala Val Arg Glu Ala Thr Ile Trp Gln Ile Trp Gly Asn
                 85                  90                  95

Gly Thr Ile Ile Asn Pro Arg Ser Asn Leu Val Leu Ala Ala Ser Ser
            100                 105                 110

Gly Ile Lys Gly Thr Thr Leu Thr Val Gln Thr Leu Asp Tyr Thr Leu
        115                 120                 125

Gly Gln Gly Trp Leu Ala Gly Asn Asp Thr Ala Pro Arg Glu Val Thr
130                 135                 140

Ile Tyr Gly Phe Arg Asp Leu Cys Met Glu Ser Asn Gly Gly Ser Val
145                 150                 155                 160

Trp Val Glu Thr Cys Val Ser Ser Gln Gln Asn Gln Arg Trp Ala Leu
                165                 170                 175

Tyr Gly Asp Gly Ser Ile Arg Pro Lys Gln Asn Gln Asp Gln Cys Leu
            180                 185                 190

Thr Cys Gly Arg Asp Ser Val Ser Thr Val Ile Asn Ile Val Ser Cys
        195                 200                 205

Ser Ala Gly Ser Ser Gly Gln Arg Trp Val Phe Thr Asn Glu Gly Ala
    210                 215                 220

Ile Leu Asn Leu Lys Asn Gly Leu Ala Met Asp Val Ala Gln Ala Asn
225                 230                 235                 240

Pro Lys Leu Arg Arg Ile Ile Ile Tyr Pro Ala Thr Gly Lys Pro Asn
                245                 250                 255

Gln Met Trp Leu Pro Val Pro
            260
```

<210> SEQ ID NO 7
<211> LENGTH: 264
<212> TYPE: PRT
<213> ORGANISM: Artificial Sequence
<220> FEATURE:
<223> OTHER INFORMATION: mistletoe lectin 1 (match)

<400> SEQUENCE: 7

```
Asp Asp Val Thr Cys Ser Ala Ser Glu Pro Thr Val Arg Ile Val Gly
 1               5                  10                  15

Arg Asn Gly Met Arg Val Asp Val Arg Asp Asp Phe His Asp G

```
Trp Val Glu Thr Cys Asp Ser Ser Gln Lys Asn Gln Gly Lys Trp Ala
                165                 170                 175

Leu Tyr Gly Asp Gly Ser Ile Arg Pro Lys Gln Asn Gln Asp Gln Cys
            180                 185                 190

Leu Thr Ser Gly Arg Asp Ser Val Ser Thr Val Ile Asn Ile Val Ser
        195                 200                 205

Cys Ser Gly Ala Ser Gly Ser Gln Arg Trp Val Phe Thr Asn Glu Gly
    210                 215                 220

Ala Ile Leu Asn Leu Lys Asn Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Phe
                260

<210> SEQ ID NO 8
<211> LENGTH: 264
<212> TYPE: PRT
<213> ORGANISM: Artificial Sequence
<220> FEATURE:
<223> OTHER INFORMATION: mistletoe lectin B2 (match)

<400> SEQUENCE: 8

Asp Asp Val Thr Cys Ser Ala Ser Glu Pro Thr Val Arg Ile Val Gly
1               5                   10                  15

Arg Ser Gly Met Arg Val Asp Val Arg Asp Asp Phe His Asp Gly
            20                  25                  30

Asn Gln Ile Gln Leu Trp Pro Ser Lys Ser Asn Asn Asp Pro Asn Gln
        35                  40                  45

Leu Trp Thr Ile Lys Arg Asp Asn Thr Ile Arg Ser Asn Gly Ser Cys
50                  55                  60

Leu Thr Thr Tyr Gly Tyr Thr Ala Gly Val Tyr Val Met Ile Phe Asp
65                  70                  75                  80

Cys Asn Thr Ala Val Arg Glu Ala Thr Ile Trp Gln Ile Trp Asp Asn
                85                  90                  95

Gly Thr Ile Ile Asn Pro Arg Ser Asn Leu Val Leu Ala Ala Ser Ser
            100                 105                 110

Gly Ile Lys Gly Thr Thr Leu Thr Val Gln Thr Leu Asp Tyr Thr Leu
        115                 120                 125

Gly Gln Gly Trp Leu Ala Gly Asn Asp Thr Ala Pro Arg Glu Val Thr
    130                 135                 140

Ile Tyr Gly Phe Arg Asp Leu Cys Met Glu Ser Asn Gln Gly Ser Val
145                 150                 155                 160

Trp Val Glu Thr Cys Asp Ser Ser Gln Lys Asn Gln Gly Lys Trp Ala
                165                 170                 175

Leu Tyr Gly Asp Gly Ser Ile Arg Pro Lys Gln Asn Gln Asp Gln Cys
            180                 185                 190

Leu Thr Val Gly Arg Asp Ser Val Ser Thr Val Ile Asn Ile Val Ser
        195                 200                 205

Cys Ser Gly Ala Ser Gly Ser Gln Arg Trp Val Phe Thr Asn Glu Tyr
    210                 215                 220

Ala Ile Leu Asn Leu Lys Ser Gly Leu Ala Met Asp Val Ala Gln Ala
225                 230                 235                 240
```

```
Asn Pro Lys Leu Arg Arg Ile Ile Ile Tyr Pro Ala Thr Gly Lys Pro
                245                 250                 255

Asn Gln Met Trp Leu Pro Val Phe
            260

<210> SEQ ID NO 9
<211> LENGTH: 264
<212> TYPE: PRT
<213> ORGANISM: Artificial Sequence
<220> FEATURE:
<223> OTHER INFORMATION: mistletoe lectin B3 (match)

<400> SEQUENCE: 9

Asp Asp Val Thr Cys Ser Ala Ser Glu Pro Thr Val Arg Ile Val Gly
1               5                   10                  15

Arg Asn Gly Met Arg Val Asp Val Arg Asp Asp Phe His Asp Gly
            20                  25                  30

Asn Gln Ile Gln Leu Trp Pro Ser Lys Ser Asn Asn Asp Pro Asn Gln
        35                  40                  45

Leu Trp Thr Ile Lys Arg Asp Gly Thr Ile Arg Ser Asn Gly Ser Cys
    50                  55                  60

Leu Thr Thr Tyr Gly Tyr Thr Ala Gly Val Tyr Val Met Ile Phe Asp
65                  70                  75                  80

Cys Asn Thr Ala Val Arg Glu Ala Thr Ile Trp Gln Ile Trp Asp Asn
                85                  90                  95

Gly Thr Ile Ile Asn Pro Arg Ser Asn Leu Val Leu Ala Ala Ser Ser
            100                 105                 110

Gly Ile Lys Gly Thr Thr Leu Thr Val Gln Thr Leu Asp Tyr Thr Leu
        115                 120                 125

Gly Gln Gly Trp Leu Ala Gly Asn Asp Thr Ala Pro Arg Glu Val Thr
    130                 135                 140

Ile Tyr Gly Phe Arg Asp Leu Cys Met Glu Ser Asn Gly Gly Ser Val
145                 150                 155                 160

Trp Val Glu Thr Cys Asp Ser Ser Gln Lys Asn Gln Gly Lys Trp Ala
                165                 170                 175

Leu Tyr Gly Asp Gly Ser Ile Arg Pro Lys Gln Asn Gln Asp Gln Cys
            180                 185                 190

Leu Thr Ser Gly Arg Asp Ser Val Ser Thr Val Ile Asn Ile Val Ser
        195                 200                 205

Cys Ser Gly Ala Ser Gly Ser Gln Arg Trp Val Phe Thr Asn Glu Gly
    210                 215                 220

Ala Ile Leu Asn Leu Lys Thr Gly Leu Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Phe
            260

<210> SEQ ID NO 10
<211> LENGTH: 264
<212> TYPE: PRT
<213> ORGANISM: Artificial Sequence
<220> FEATURE:
<223> OTHER INFORMATION: mistletoe lectin B4 (match)

<400> SEQUENCE: 10

Asp Asp Val Thr Cys Ser Ala Ser Glu

-continued

```
Arg Asn Gly Met Arg Val Asp Val Arg Asp Asp Phe His Asp Gly
         20                  25                  30

Asn Gln Ile Gln Leu Trp Pro Ser Lys Ser Asn Asn Asp Pro Asn Gln
             35                  40                  45

Leu Trp Thr Ile Lys Arg Asp Gly Thr Ile Arg Ser Asn Gly Ser Cys
     50                  55                  60

Leu Thr Thr Tyr Gly Tyr Thr Ala Gly Val Tyr Val Met Ile Phe Asp
 65                  70                  75                  80

Cys Asn Thr Ala Val Arg Glu Ala Thr Ile Trp Gln Ile Trp Asp Asn
                 85                  90                  95

Gly Thr Ile Ile Asn Pro Arg Ser Asn Leu Val Leu Ala Ala Ser Ser
                100                 105                 110

Gly Ile Lys Gly Thr Thr Leu Thr Val Gln Thr Leu Asp Tyr Thr Leu
            115                 120                 125

Gly Gln Gly Trp Leu Ala Gly Asn Asp Thr Ala Pro Arg Glu Val Thr
        130                 135                 140

Ile Tyr Gly Phe Arg Asp Leu Cys Met Glu Ser Asn Gly Gly Ser Val
145                 150                 155                 160

Trp Val Glu Thr Cys Asp Ser Ser Gln Lys Asn Gln Gly Lys Trp Ala
                165                 170                 175

Leu Tyr Gly Asp Gly Ser Ile Arg Pro Lys Gln Asn Gln Asp Gln Cys
            180                 185                 190

Leu Thr Ser Gly Arg Asp Ser Val Ser Thr Val Ile Asn Ile Val Ser
        195                 200                 205

Cys Ser Gly Ala Ser Gly Ser Gln Arg Trp Val Phe Thr Asn Glu Gly
210                 215                 220

Ala Ile Leu Asn Leu Lys Lys Gly Pro Ala Met Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Phe
            260

<210> SEQ ID NO 11
<211> LENGTH: 264
<212> TYPE: PRT
<213> ORGANISM: Artificial Sequence
<220> FEATURE:
<223> OTHER INFORMATION: mistletoe lectin B5 (match)

<400

```
Gly Ile Lys Gly Thr Thr Leu Thr Val Gln Thr Leu Asp Tyr Thr Leu
            115                 120                 125

Gly Gln Gly Trp Leu Ala Gly Asn Asp Thr Ala Pro Arg Glu Val Thr
        130                 135                 140

Ile Tyr Gly Phe Arg Asp Leu Cys Met Glu Ser Asn Gly Gly Ser Val
145                 150                 155                 160

Trp Val Glu Thr Cys Asp Ser Ser Gln Lys Asn Gln Gly Lys Trp Ala
                165                 170                 175

Leu Tyr Gly Asp Gly Ser Ile Arg Pro Lys Gln Asn Gln Asp Gln Cys
            180                 185                 190

Leu Thr Ser Gly Arg Asp Ser Val Ser Thr Val Ile Asn Ile Val Ser
        195                 200                 205

Cys Ser Gly Ala Ser Gly Ser Gln Arg Trp Val Phe Thr Asn Glu Gly
210                 215                 220

Ala Ile Leu Asn Leu Lys Asn Ser Leu Met Val Asp Val Ala Gln Ala
225                 230                 235                 240

Asn Pro Lys Leu Arg Arg Ile Ile Ile Tyr Pro Ala Thr Gly Lys Pro
                245                 250                 255

Asn Gln Met Trp Leu Pro Val Phe
            260

<210> SEQ ID NO 12
<211> LENGTH: 1598
<212> TYPE: DNA
<213> ORGANISM: Artificial Sequence
<220> FEATURE:
<223> OTHER INFORMATION: ML-I
<220> FEATURE:
<221> NAME/KEY: misc_feature
<222> LOCATION: 319
<223> OTHER INFORMATION: product= "n is gat aga or missing"
      /label= Z1
<220> FEATURE:
<221> NAME/KEY: misc_feature
<222> LOCATION: 1322
<223> OTHER INFORMATION: product= "n is ggc or missing"
      /label= Z2

<400> SEQUENCE: 12
tacgagaggc taagactcag agttacgcat caaaccacgg gcgakgaata cttccggttc      60
atcacgcttc tccgagatta tgtctcaagc ggaagctttt ccaatgagat accactcttg     120
cgtcagtcta cgatccccgt ctccgatgcg caaagatttg tcttggtgga gctcaccaac     180
caggggsrrg actcgrtyac ggccgccatc gacgttacca atsyktacgt cgtggcttac     240
caagcaggcg accaatccta cttttttgcgc gacgcaccac gcggcgcgga aacgcacctc     300
ttcaccggca ccacccgant cctctctccc attcamygga agctacmcyg atctggagcg     360
atacgccgga catagggacc agatccctct cggtatagas caactcattc aatccgtcwc     420
kgcgcttcgt twyccgggcg gcagcacgcg trcycaagct cgttcgattt taatcctcat     480
tcagatgatc tccgaggccg ccagattcaa tccatcctta tggaggkmyc gccaakayat     540
taacagtggg gmrtcatttc tgccagacrt gtacatgctg agctggaga cgagttgggg     600 ccaacaatcc acgcaagtcc agcattcaac cgatggcgtt tttaataacc cawtycggtt     660
ggctataycy mcyggtaact tcgtgacgtt gwcyaatgtt cgckmygtga tgcccagctt     720
ggcgatcatg ttgtttgtat gcggagagcg gccatcttcc tctgacgtgc gctattggcc     780
gctggtcata cgaccgtga tagccgatga tgttacctgc agtgcttcgg aacctacggt     840
gcggattgtg ggtcgaartg gcatgycgcgt ggacgtccga gatgacgatt ccacgatgg     900
```

-continued

| | |
|---|---|
| gaatcagata cagttgtggc cctccaagtc caacaatgat ccgaatcagt tgtggacgat | 960 |
| caaaagggat rrmaccattc gatccaatgg cagctgcttg accacgtatg gctatactgc | 1020 |
| tggcgtctat gtgatgatct tcgactgtaa tactgctgtg cgggaggcca ctatttggca | 1080 |
| gatatgggrc aatgggacca tcatcaatcc aagatccaat ctggttttgg cagcatcatc | 1140 |
| tggaatcaaa ggcactacgc ttacggtgca aacactggat tacacgttgg gacagggctg | 1200 |
| gcttgccggt aatgataccg ccccacgcga ggtgaccata tatggtttca gggacctttg | 1260 |
| catggaatca aatsraggga gtgtgtgggt ggagacgtgc gwsagtagcc aamagaacca | 1320 |
| anaratgggc tttgtacggg gatggttcta tacgccccaa acaaaaccaa gaccaatgcc | 1380 |
| tcacckbtgg gagagactcc gtttcaacag taatcaatat agttagctgc agcgswgswt | 1440 |
| cgkskkskca gcgatgggtg tttaccaatg aakrsgccat tttgaattta aagavwrgsy | 1500 |
| ygrysrtgga tgtggcgcaa gcaaatccaa agctccgccg aataattatc tatcctgcca | 1560 |
| caggaaaacc aaatcaaatg tggcttcccg tgyymtga | 1598 |

<210> SEQ ID NO 13
<211> LENGTH: 763
<212> TYPE: DNA
<213> ORGANISM: Artificial Sequence
<220> FEATURE:
<223> OTHER INFORMATION: MLA
<220> FEATURE:
<221> NAME/KEY: misc_feature
<222> LOCATION: 319
<223> OTHER INFORMATION: product= "n is gat aga or missing"
      /label= z1

<400> SEQUENCE: 13

| | |
|---|---|
| tacgagaggc taagactcag agttacgcat caaaccacgg gcgakgaata cttccggttc | 60 |
| atcacgcttc tccgagatta tgtctcaagc ggaagctttt ccaatgagat accactcttg | 120 |
| cgtcagtcta cgatccccgt ctccgatgcg caaagatttg tcttggtgga gctcaccaac | 180 |
| caggggsrrg actcgrtyac ggccgccatc gacgttacca atsyktacgt cgtggcttac | 240 |
| caagcaggcg accaatccta ctttttgcgc gacgcaccac gcggcgcgga aacgcacctc | 300 |
| ttcaccggca ccacccgant cctctctccc attcamygga agctacmcyg atctggagcg | 360 |
| atacgccgga catagggacc agatccctct cggtatagas caactcattc aatccgtcwc | 420 |
| kgcgcttcgt twyccgggcg gcagcacgcg trcycaagct cgttcgattt taatcctcat | 480 |
| tcagatgatc tccgaggccg ccagattcaa tcccatctta tggaggkmyc gccaakayat | 540 |
| taacagtggg gmrtcatttc tgccagacrt gtacatgctg gagctggaga cgagttgggg | 600 |
| ccaacaatcc acgcaagtcc agcattcaac cgatggcgtt tttaataacc cawtycggtt | 660 |
| ggctataycy mcyggtaact tcgtgacgtt gwcyaatgtt cgckmygtga tcgccagctt | 720 |
| ggcgatcatg ttgtttgtat gcggagagcg gccatcttcc tct | 763 |

<210> SEQ ID NO 14
<211> LENGTH: 793
<212> TYPE: DNA
<213> ORGANISM: Artificial Sequence
<220> FEATURE:
<223> OTHER INFORMATION: MLB
<220> FEATURE:
<221> NAME/KEY: misc_feature
<222> LOCATION: 517
<223> OTHER INFORMATION: product= "n is ggc or missing"
      /label= Z2

```
<400> SEQUENCE: 14
gatgatgtta cctgcagtgc ttcggaacct acggtgcgga ttgtgggtcg aartggcatg      60
ygcgtggacg tccgagatga cgatttccac gatgggaatc agatacagtt gtggccctcc     120
aagtccaaca atgatccgaa tcagttgtgg acgatcaaaa gggatrrmac cattcgatcc     180
aatggcagct gcttgaccac gtatggctat actgctggcg tctatgtgat gatcttcgac     240
tgtaatactg ctgtgcggga ggccactatt tggcagatat gggrcaatgg gaccatcatc     300
aatccaagat ccaatctggt tttggcagca tcatctggaa tcaaaggcac tacgcttacg     360
gtgcaaacac tggattacac gttgggacag ggctggcttg ccgtaatga taccgcccca     420 cgcgaggtga ccatatatgg tttcagggac ctttgcatgg aatcaaatsr agggagtgtg     480
tgggtggaga cgtgcgwsag tagccaamag aaccaanara tgggctttgt acggggatgg     540
ttctatacgc cccaaacaaa accaagacca atgcctcacc kbtgggagag actccgtttc     600
aacagtaatc aatatagtta gctgcagcgs wgswtcgksk kskcagcgat gggtgtttac     660
caatgaakrs gccattttga atttaaagav wrgsyygrys rtggatgtgg cgcaagcaaa     720
tccaaagctc cgccgaataa ttatctatcc tgccacagga aaaccaaatc aaatgtggct     780
tcccgtgyym tga                                                       793

<210> SEQ ID NO 15
<211> LENGTH: 1596
<212> TYPE: DNA
<213> ORGANISM: Artificial Sequence
<220> FEATURE:
<223> OTHER INFORMATION: MLA-I

<400> SEQUENCE: 15
tacgagaggc taagactcag agttacgcat caaaccacgg gcgaggaata cttccggttc      60
atcacgcttc tccgagatta tgtctcaagc ggaagctttt ccaatgagat accactcttg     120
cgtcagtcta cgatccccgt ctccgatgcg caaagatttg tcttggtgga gctcaccaac     180
caggggggag actcgatcac ggccgccatc gacgttacca atctgtacgt cgtggcttac     240
caagcaggcg accaatccta cttttttgcgc gacgcaccac gcggcgcgga aacgcacctc     300
ttcaccggca ccacccgatc ctctctccca ttcaacggaa gctaccctga tctggagcga     360
tacgccggac atagggacca gatccctctc ggtatagacc aactcattca atccgtcacg     420
gcgcttcgtt ttccgggcgg cagcacgcgt acccaagctc gttcgatttt aatcctcatt     480
cagatgatct ccgaggccgc cagattcaat cccatcttat ggagggctcg ccaatacatt     540
aacagtgggg cgtcatttct gccagacgtg tacatgctgg agctggagac gagttggggc     600
caacaatcca cgcaagtcca gcattcaacc gatggcgttt taataaccc aattcggttg      660 gctataccc ccggtaactt cgtgacgttg accaatgttc gcgacgtgat cgccagcttg     720
gcgatcatgt tgtttgtatg cggagagcgg ccatcttcct ctgacgtgcg ctattggccg     780
ctggtcatac gacccgtgat agccgatgat gttacctgca gtgcttcgga acctacggtg     840
cggattgtgg gtcgaaatgg catgtgcgtg acgtccgag atgacgattt ccacgatggg     900
aatcagatac agttgtggcc ctccaagtcc aacaatgatc cgaatcagtt gtggacgatc     960
aaaagggatg gaaccattcg atccaatggc agctgcttga ccacgtatgg ctatactgct    1020
ggcgtctatg tgatgatctt cgactgtaat actgctgtgc gggaggccac tatttggcag    1080
atatggggca atgggaccat catcaatcca agatccaatc tggttttggc agcatcatct    1140
ggaatcaaag gcactacgct tacggtgcaa acactggatt acacgttggg acaggctgg    1200
```

-continued

```
cttgccggta atgataccgc cccacgcgag gtgaccatat atggtttcag ggacctttgc   1260
atggaatcaa atggagggag tgtgtgggtg gagacgtgcg tgagtagcca acagaaccaa   1320
agatgggctt tgtacgggga tggttctata cgcccccaaac aaaaccaaga ccaatgcctc   1380
acctgtggga gagactccgt ttcaacagta atcaatatag ttagctgcag cgctggatcg   1440
tctgggcagc gatgggtgtt taccaatgaa ggggccattt tgaatttaaa gaatgggttg   1500
gccatggatg tggcgcaagc aaatccaaag ctccgccgaa taattatcta tcctgccaca   1560
ggaaaaccaa atcaaatgtg gcttcccgtg ccatga                             1596
```

<210> SEQ ID NO 16
<211> LENGTH: 762
<212> TYPE: DNA
<213> ORGANISM: Artificial Sequence
<220> FEATURE:
<223> OTHER INFORMATION: mistletoe lectin A1

<400> SEQUENCE: 16

```
tacgagaggc taagactcag agttacgcat caaaccacgg gcgaggaata cttccggttc     60
atcacgcttc tccgagatta tgtctcaagc ggaagctttt ccaatgagat accactcttg    120
cgtcagtcta cgatccccgt ctccgatgcg caaagatttg tcttggtgga gctcaccaac    180
caggggcagg actcggttac ggccgccatc gacgttacca atgcttacgt cgtggcttac    240
caagcaggcg accaatccta ctttttgcgc gacgcaccac gcggcgcgga aacgcacctc    300
ttcaccggca ccacccgatc ctctctccca ttcaacggaa gctaccctga tctggagcga    360
tacgccggac atagggacca gatccctctc ggtatagacc aactcattca atccgtcacg    420
gcgcttcgtt ttccgggcgg cagcacgcgt acccaagctc gttcgatttt aatcctcatt    480
cagatgatct ccgaggccgc cagattcaat cccatcttat ggaggtaccg ccaatacatt    540
aacagtgggg cgtcatttct gccagacgtg tacatgctgg agctggagac gagttggggc    600
caacaatcca cgcaagtcca gcattcaacc gatggcgttt ttaataaccc aattcggttg    660
gctatacccc ccggtaactt cgtgacgttg accaatgttc gcgacgtgat cgccagcttg    720
gcgatcatgt tgtttgtatg cggagagcgg ccatcttcct ct                       762
```

<210> SEQ ID NO 17
<211> LENGTH: 768
<212> TYPE: DNA
<213> ORGANISM: Artificial Sequence
<220> FEATURE:
<223> OTHER INFORMATION: mistletoe lectin A2

<400> SEQUENCE: 17

```
tacgagaggc taagactcag agttacgcat caaaccacgg gcgatgaata cttccggttc     60
atcacgcttc tccgagatta tgtctcaagc ggaagctttt ccaatgagat accactcttg    120
cgtcagtcta cgatccccgt ctccgatgcg caaagatttg tcttggtgga gctcaccaac    180
caggggcagg actcgatcac ggccgccatc gacgttacca atgcttacgt cgtggcttac    240
caagcaggcg accaatccta ctttttgcgc gacgcaccac gcggcgcgga aacgcacctc    300
ttcaccggca ccacccgaga tagatcctct ctcccattca ctggaagcta caccgatctg    360
gagcgatacg ccggacatag ggaccagatc cctctcggta tagagcaact cattcaatcc    420
gtctctgcgc ttcgttaccc gggcggcagc acgcgtgctc aagctcgttc gattttaatc    480
ctcattcaga tgatctccga ggccgccaga ttcaatccca tcttatggag gtaccgccaa    540
gatattaaca gtggggaatc atttctgcca gacatgtaca tgctggagct ggagacgagt    600
```

-continued

| tggggccaac aatccacgca agtccagcat tcaaccgatg gcgtttttaa taacccattc | 660 |
| cggttggcta tatctactgg taacttcgtg acgttgtcta atgttcgctc tgtgatcgcc | 720 |
| agcttggcga tcatgttgtt tgtatgcgga gagcggccat cttcctct | 768 |

<210> SEQ ID NO 18
<211> LENGTH: 1596
<212> TYPE: DNA
<213> ORGANISM: Artificial Sequence
<220> FEATURE:
<223> OTHER INFORMATION: MLI (matched)

<400> SEQUENCE: 18

| tatgaaagat tgaggttgag ggtgactcac cagactacag gagaagagta ttttagattt | 60 |
| attactttgt tgagggatta cgttagttct ggttctttca gtaacgaaat tcctttgctt | 120 |
| agacaatcta ctattccagt ttctgatgct cagcgtttcg ttcttgttga attgactaac | 180 |
| caaggaggtg atagtattac tgctgctatt gatgtgacta acctttatgt tgttgcatat | 240 |
| caggctggtg atcagtctta tttccttagg gatgctccta gaggagctga gactcatttg | 300 |
| tttactggta caacacggag ttctttgcct tttaacggtt cttatccaga cttggaaaga | 360 |
| tatgctggtc acagagatca aattccattg ggaattgatc agttgatcca gagtgttact | 420 |
| gctttgagat tcccaggtgg atctactaga acacaggcaa gatctatcct tattttgatc | 480 |
| caaatgatta gtgaagctgc taggtttaac cctattcttt ggagagcaag acagtatatc | 540 |
| aactctggtg cttctttcct tcctgatgtt tatatgcttg aacttgaaac ttcatgggga | 600 |
| cagcagtcta ctcaggttca acacagtaca gacggtgtgt caacaatcc tatcagactt | 660 |
| gcaattccac ctggaaattt tgttactctt acaaacgtga gagatgttat tgcttctctt | 720 |
| gctattatgc ttttcgtttg tggtgaaaga ccttctagtt ctgatgttag atactggcca | 780 |
| ttggttatta ggcctgttat cgctgacgat gtgacatgtt ctgcatctga accaactgtt | 840 |
| aggatcgttg gaagaaacgg tatgtgtgtt gatgttcggg acgatgactt tcatgacggt | 900 |
| aaccaaatcc aactttggcc tagtaagtct aataacgacc caaaccaact ttggactatt | 960 |
| aagagagacg gtacaatcag gtctaacgga tcttgtctta ctacatacgg ttacactgca | 1020 |
| ggagtttacg ttatgatttt tgattgcaac acagcagtta gagaagctac aatctggcaa | 1080 |
| atctggggta acggaactat tattaaccct cgttctaact ggtgtcttgc tgcttctagt | 1140 |
| ggtattaagg gaacaacttt gactgttcag actttggact atactcttgg tcaaggatgg | 1200 |
| ttggctggaa acgacacagc tcctagagaa gttacaatct acggatttag agatttgtgt | 1260 |
| atggagtcta acgtggatc tgtttgggtt gaaacttgtg tttcatctca gcaaaatcag | 1320 |
| aggtgggcac tttatggtga cggaagtatc agacctaagc agaatcagga tcagtgtttg | 1380 |
| acatgcggta gggatagtgt gtctactgtt attaacattg tgtcttgttc tgcaggtagt | 1440 |
| tctggacaaa ggtgggtttt cacaaacgag ggtgctatcc ttaacttgaa gaacggtctt | 1500 |
| gctatggatg ttgctcaggc taaccctaag ttgagaagga ttatcattta cccagctact | 1560 |
| ggtaagccta accagatgtg gttgccagtt ccttat | 1596 |

<210> SEQ ID NO 19
<211> LENGTH: 762
<212> TYPE: DNA
<213> ORGANISM: Artificial Sequence
<220> FEATURE:
<223> OTHER INFORMATION: mistletoe lectin A1

-continued

<400> SEQUENCE: 19

```
tatgaaagat tgaggttgag ggtgactcac cagactacag gagaagagta ttttagattt     60
attactttgt tgagggatta cgttagttct ggttctttca gtaacgaaat tcctttgctt    120
agacaatcta ctattccagt ttctgatgct cagcgtttcg ttcttgttga attgactaac    180
caaggacagg atagtgttac tgctgctatt gatgtgacta acgcttatgt tgttgcatat    240
caggctggtg atcagtctta tttccttagg gatgctccta gaggagctga gactcatttg    300
tttactggta caacacggag ttctttgcct tttaacggtt cttatccaga cttggaaaga    360
tatgctggtc acagagatca aattccattg ggaattgatc agttgatcca gagtgttact    420
gctttgagat tcccaggtgg atctactaga acacaggcaa gatctatcct tattttgatc    480
caaatgatta gtgaagctgc taggtttaac cctattcttt ggagatacag acagtatatc    540
aactctggtg cttctttcct tcctgatgtt tatatgcttg aacttgaaac ttcatgggga    600
cagcagtcta ctcaggttca acacagtaca gacggtgtgt tcaacaatcc tatcagactt    660
gcaattccac ctggaaattt tgttactctt acaaacgtga gagatgttat tgcttctctt    720
gctattatgc ttttcgtttg tggtgaaaga ccttctagtt ct                       762
```

<210> SEQ ID NO 20
<211> LENGTH: 768
<212> TYPE: DNA
<213> ORGANISM: Artificial Sequence
<220> FEATURE:
<223> OTHER INFORMATION: mistletoe lectin A2

<400> SEQUENCE: 20

```
tatgaaagat tgaggttgag ggtgactcac cagactacag gagatgagta ttttagattt     60
attactttgt tgagggatta cgttagttct ggttctttca gtaacgaaat tcctttgctt    120
agacaatcta ctattccagt ttctgatgct cagcgtttcg ttcttgttga attgactaac    180
caaggacagg atagtattac tgctgctatt gatgtgacta acgcttatgt tgttgcatat    240
caggctggtg atcagtctta tttccttagg gatgctccta gaggagctga gactcatttg    300
tttactggta caacacggga tagaagttct ttgcctttta ctggttctta tacagacttg    360
gaaagatatg ctggtcacag agatcaaatt ccattgggaa ttgagcagtt gatccagagt    420
gtttctgctt tgagataccc aggtggatct actagagctc aggcaagatc tatccttatt    480
ttgatccaaa tgattagtga agctgctagg tttaacccta ttctttggag atacagacag    540
gatatcaact ctggtgaatc tttccttcct gatatgtata tgcttgaact tgaaacttca    600
tggggacagc agtctactca ggttcaacac agtacagacg gtgtgttcaa caatcctttc    660
agacttgcaa tttctactgg aaattttgtt actctttcta acgtgagatc tgttattgct    720
tctcttgcta ttatgctttt cgtttgtggt gaaagacctt ctagttct                 768
```

<210> SEQ ID NO 21
<211> LENGTH: 792
<212> TYPE: DNA
<213> ORGANISM: Artificial Sequence
<220> FEATURE:
<223> OTHER INFORMATION: mistletoe lectin B

<400> SEQUENCE: 21

```
gatgatgtta cctgcagtgc ttcggaacct acggtgcgga ttgtgggtcg aaatggcatg     60
tgcgtggacg tccgagatga cgatttccac gatgggaatc agatacagtt gtggccctcc    120
aagtccaaca atgatccgaa tcagttgtgg acgatcaaaa gggatggaac cattcgatcc    180
```

-continued

```
aatggcagct gcttgaccac gtatggctat actgctggcg tctatgtgat gatcttcgac    240
tgtaatactg ctgtgcggga ggccactatt tggcagatat ggggcaatgg gaccatcatc    300
aatccaagat ccaatctggt tttggcagca tcatctggaa tcaaaggcac tacgcttacg    360
gtgcaaacac tggattacac gttgggacag ggctggcttg ccggtaatga taccgcccca    420
cgcgaggtga ccatatatgg tttcagggac ctttgcatgg aatcaaatgg agggagtgtg    480
tgggtggaga cgtgcgtgag tagccaacag aaccaaagat gggctttgta cggggatggt    540
tctatacgcc ccaaacaaaa ccaagaccaa tgcctcacct gtgggagaga ctccgtttca    600
acagtaatca atatagttag ctgcagcgct ggatcgtctg ggcagcgatg ggtgtttacc    660
aatgaagggg ccattttgaa tttaaagaat gggttggcca tggatgtggc gcaagcaaat    720
ccaaagctcc gccgaataat tatctatcct gccacaggaa aaccaaatca aatgtggctt    780
cccgtgccat ga                                                        792
```

<210> SEQ ID NO 22
<211> LENGTH: 795
<212> TYPE: DNA
<213> ORGANISM: Artificial Sequence
<220> FEATURE:
<223> OTHER INFORMATION: mistletoe lectin B1

<400> SEQUENCE: 22

```
gatgatgtta cctgcagtgc ttcggaacct acggtgcgga ttgtgggtcg aaatggcatg     60
cgcgtggacg tccgagatga cgatttccac gatgggaatc agatacagtt gtggccctcc    120
aagtccaaca atgatccgaa tcagttgtgg acgatcaaaa gggatggaac cattcgatcc    180
aatggcagct gcttgaccac gtatggctat actgctggcg tctatgtgat gatcttcgac    240
tgtaatactg ctgtgcggga ggccactatt tggcagatat gggacaatgg gaccatcatc    300
aatccaagat ccaatctggt tttggcagca tcatctggaa tcaaaggcac tacgcttacg    360
gtgcaaacac tggattacac gttgggacag ggctggcttg ccggtaatga taccgcccca    420
cgcgaggtga ccatatatgg tttcagggac ctttgcatgg aatcaaatgg agggagtgtg    480
tgggtggaga cgtgcgacag tagccaaaag aaccaaggca aatgggcttt gtacggggat    540
ggttctatac gccccaaaca aaaccaagac caatgcctca cctctgggag agactccgtt    600
tcaacagtaa tcaatatagt tagctgcagc ggagcttcgg ggtctcagcg atgggtgttt    660
accaatgaag ggccatttt gaatttaaag aatgggttgg ccatggatgt ggcgcaagca    720
aatccaaagc tccgccgaat aattatctat cctgccacag gaaaaccaaa tcaaatgtgg    780
cttcccgtgt tctga                                                     795
```

<210> SEQ ID NO 23
<211> LENGTH: 795
<212> TYPE: DNA
<213> ORGANISM: Artificial Sequence
<220> FEATURE:
<223> OTHER INFORMATION: mistletoe lectin B2

<400> SEQUENCE: 23

```
gatgatgtta cctgcagtgc ttcggaacct acggtgcgga ttgtgggtcg aagtggcatg     60
cgcgtggacg tccgagatga cgatttccac gatgggaatc agatacagtt gtggccctcc    120
aagtccaaca atgatccgaa tcagttgtgg acgatcaaaa gggataacac cattcgatcc    180
aatggcagct gcttgaccac gtatggctat actgctggcg tctatgtgat gatcttcgac    240
tgtaatactg ctgtgcggga ggccactatt tggcagatat gggacaatgg gaccatcatc    300
```

-continued

```
aatccaagat ccaatctggt tttggcagca tcatctggaa tcaaaggcac tacgcttacg      360
gtgcaaacac tggattacac gttgggacag ggctggcttg ccggtaatga taccgcccca      420
cgcgaggtga ccatatatgg tttcagggac ctttgcatgg aatcaaatca agggagtgtg      480
tgggtggaga cgtgcgacag tagccaaaag aaccaaggca atgggcttt gtacggggat       540 ggttctatac gccccaaaca aaaccaagac caatgcctca ccgttgggag agactccgtt      600
tcaacagtaa tcaatatagt tagctgcagc ggagcttcgg ggtctcagcg atgggtgttt     660
accaatgaat acgccatttt gaatttaaag agtgggttgg ccatggatgt ggcgcaagca      720
aatccaaagc tccgccgaat aattatctat cctgccacag gaaaaccaaa tcaaatgtgg      780
cttcccgtgt tctga                                                      795
```

<210> SEQ ID NO 24
<211> LENGTH: 795
<212> TYPE: DNA
<213> ORGANISM: Artificial Sequence
<220> FEATURE:
<223> OTHER INFORMATION: mistletoe lectin B3

<400> SEQUENCE: 24

```
gatgatgtta cctgcagtgc ttcggaacct acggtgcgga ttgtgggtcg aaatggcatg      60
cgcgtggacg tccagatgac gatttccac gatgggaatc agatacagtt gtggccctcc      120
aagtccaaca atgatccgaa tc

-continued

```
cgcgaggtga ccatatatgg tttcagggac ctttgcatgg aatcaaatgg agggagtgtg    480
tgggtggaga cgtgcgacag tagccaaaag aaccaaggca aatgggcttt gtacggggat    540
ggttctatac gccccaaaca aaaccaagac caatgcctca cctctgggag agactccgtt    600
tcaacagtaa tcaatatagt tagctgcagc ggagcttcgg ggtctcagcg atgggtgttt    660
accaatgaag ggccattt gaatttaaag aaagggccgg ccatggatgt ggcgcaagca    720
aatccaaagc tccgccgaat aattatctat cctgccacag gaaaaccaaa tcaaatgtgg    780
cttcccgtgt tctga                                                     795
```

<210> SEQ ID NO 26
<211> LENGTH: 795
<212> TYPE: DNA
<213> ORGANISM: Artificial Sequence
<220> FEATURE:
<223> OTHER INFORMATION: mistletoe lectin B5

<400> SEQUENCE: 26

```
gatgatgtta cctgcagtgc ttcggaacct acggtgcgga ttgtgggtcg aaatggcatg     60
cgcgtggacg tccgagatga cgatttccac gatgggaatc agatacagtt gtggccctcc    120
aagtccaaca atgatccgaa tcagttgtgg acgatcaaaa gggatggaac cattcgatcc    180
aatggcagct gcttgaccac gtatggctat actgctggcg tctatgtgat gatcttcgac    240
tgtaatactg ctgtgcggga ggccactatt tggcagatat gggacaatgg gaccatcatc    300
aatccaagat ccaatctggt tttggcagca tcatctggaa tcaaaggcac tacgcttacg    360
gtgcaaacac tggattacac gttgggacag ggctggcttg ccggtaatga taccgcccca    420
cgcgaggtga ccatatatgg tttcagggac ctttgcatgg aatcaaatgg agggagtgtg    480
tgggtggaga cgtgcgacag tagccaaaag aaccaaggca aatgggcttt gtacggggat    540
ggttctatac gccccaaaca aaaccaagac caatgcctca cctctgggag agactccgtt    600
tcaacagtaa tcaatatagt tagctgcagc ggagcttcgg ggtctcagcg atgggtgttt    660
accaatgaag ggccatttt gaatttaaag aatagcttga tggtggatgt ggcgcaagca    720
aatccaaagc tccgccgaat aattatctat cctgccacag gaaaaccaaa tcaaatgtgg    780
cttcccgtgt tctga                                                     795
```

<210> SEQ ID NO 27
<211> LENGTH: 792
<212> TYPE: DNA
<213> ORGANISM: Artificial Sequence
<220> FEATURE:
<223> OTHER INFORMATION: mistletoe lectin B

<400> SEQUENCE: 27

```
gacgatgtga catgttctgc atctgaacca actgttagga tcgttggaag aaacggtatg     60
tgtgttgatg ttcgggacga tgactttcat gacggtaacc aaatccaact ttggcctagt    120
aagtctaata acgacccaaa ccaactttgg actattaaga gagacggtac aatcaggtct    180
aacggatctt gtcttactac atacggttac actgcaggag tttacgttat gatttttgat    240
tgcaacacag cagttagaga agctacaatc tggcaaatct ggggtaacgg aactattatt    300
aaccctcgtt ctaacttggt gcttgctgct tctagtggta ttaagggaac aactttgact    360
gttcagactt tggactatac tcttggtcaa ggatggttgg ctggaaacga cacagctcct    420
agagaagtta caatctacgg atttagagat ttgtgtatgg agtctaacgg tggatctgtt    480
tgggttgaaa cttgtgtttc atctcagcaa aatcagaggt gggcacttta tggtgacgga    540
```

-continued agtatcagac ctaagcagaa tcaggatcag tgtttgacat gcggtaggga tagtgtgtct 600
actgttatta acattgtgtc ttgttctgca ggtagttctg gacaaaggtg ggttttcaca 660
aacgagggtg ctatccttaa cttgaagaac ggtcttgcta tggatgttgc tcaggctaac 720
cctaagttga gaaggattat catttaccca gctactggta agcctaacca gatgtggttg 780
ccagttcctt at 792

<210> SEQ ID NO 28
<211> LENGTH: 795
<212> TYPE: DNA
<213> ORGANISM: Artificial Sequence
<220> FEATURE:
<223> OTHER INFORMATION: mistletoe lectin 1 (match)

<400> SEQUENCE: 28
gacgatgtga catgttctgc atctgaacca actgttagga tcgttggaag aaacggtatg 60
cgtgttgatg ttcgggacga tgactttcat gacggtaacc aaatccaact ttggcctagt 120
aagtctaata acgacccaaa ccaactttgg actattaaga gagacggtac aatcaggtct 180
aacggatctt gtcttactac atacggttac actgcaggag tttacgttat gatttttgat 240
tgcaacacag cagttagaga agctacaatc tggcaaatct gggataacgg aactattatt 300
aaccctcgtt ctaacttggt gcttgctgct tctagtggta ttaagggaac aactttgact 360
gttcagactt tggactatac tcttggtcaa ggatggttgg ctggaaacga cacagctcct 420
agagaagtta caatctacgg atttagagat ttgtgtatgg agtctaacgg tggatctgtt 480
tgggttgaaa cttgtgattc atctcagaaa aatcagggca agtgggcact ttatggtgac 540
ggaagtatca gacctaagca gaatcaggat cagtgtttga catccggtag ggatagtgtg 600
tctactgtta ttaacattgt gtcttgttct ggagctagtg gatctcaaag gtgggttttc 660
acaaacgagg gtgctatcct taacttgaag aacggtcttg ctatggatgt tgctcaggct 720
aaccctaagt tgagaaggat tatcatttac ccagctactg gtaagcctaa ccagatgtgg 780
ttgccagttt tttat 795

<210> SEQ ID NO 29
<211> LENGTH: 795
<212> TYPE: DNA
<213> ORGANISM: Artificial Sequence
<220> FEATURE:
<223> OTHER INFORMATION: mistletoe lectin B2 (match)

<400> SEQUENCE: 29
gacgatgtga catgttctgc atctgaacca actgttagga tcgttggaag aagcggtatg 60
cgtgttgatg ttcgggacga tgactttcat gacggtaacc aaatccaact ttggcctagt 120
aagtctaata acgacccaaa ccaactttgg actattaaga gagacaatac aatcaggtct 180
aacggatctt gtcttactac atacggttac actgcaggag tttacgttat gatttttgat 240
tgcaacacag cagttagaga agctacaatc tggcaaatct gggataacgg aactattatt 300
aaccctcgtt ctaacttggt gcttgctgct tctagtggta ttaagggaac aactttgact 360
gttcagactt tggactatac tcttggtcaa ggatggttgg ctggaaacga cacagctcct 420
agagaagtta caatctacgg atttagagat ttgtgtatgg agtctaacca gggatctgtt 480
tgggttgaaa cttgtgattc atctcagaaa aatcagggca agtgggcact ttatggtgac 540
ggaagtatca gacctaagca gaatcaggat cagtgtttga cagtcggtag ggatagtgtg 600
tctactgtta ttaacattgt gtcttgttct ggagctagtg gatctcaaag gtgggttttc 660

```
acaaacgagt atgctatcct taacttgaag tccggtcttg ctatggatgt tgctcaggct    720
aaccctaagt tgagaaggat tatcatttac ccagctactg gtaagcctaa ccagatgtgg    780
ttgccagttt tttat                                                     795

<210> SEQ ID NO 30
<211> LENGTH: 795
<212> TYPE: DNA
<213> ORGANISM: Artificial Sequence
<220> FEATURE:
<223> OTHER INFORMATION: mistletoe lectin B3 (match)

<400> SEQUENCE: 30
gacgatgtga catgttctgc atctgaacca actgttagga tcgttggaag aaacggtatg     60
cgtgttgatg ttcgggacga tgactttcat gacggtaacc aaatccaact ttggcctagt    120 aagtctaata

-continued

```
aaccctaagt tgagaaggat tatcatttac ccagctactg gtaagcctaa ccagatgtgg    780
ttgccagttt tttat                                                     795

<210> SEQ ID NO 32
<211> LENGTH: 795
<212> TYPE: DNA
<213> ORGANISM: Artificial Sequence
<220> FEATURE:
<223> OTHER INFORMATION: mistletoe lectin B5 (match)

<400> SEQUENCE: 32
gacgatgtga catgttctgc atctgaacca actgttagga tcgttggaag aaacggtatg     60
cgtgttgatg ttcgggacga tgactttcat gacggtaacc aaatccaact ttggcctagt    120
aagtctaata acgacccaaa ccaactttgg actattaaga gagacggtac aatcaggtct    180
aacggatctt gtcttactac atacggttac actgcaggag tttacgttat gatttttgat    240
tgcaacacag cagttagaga agctacaatc tggcaaatct gggataacgg aactattatt    300
aaccctcgtt ctaacttggt gcttgctgct tctagtggta ttaagggaac aactttgact    360
gttcagactt tggactatac tcttggtcaa ggatggttgg ctggaaacga cacagctcct    420
agagaagtta caatctacgg atttagagat ttgtgtatgg agtctaacgg tggatctgtt    480
tgggttgaaa cttgtgattc atctcagaaa aatcagggca agtgggcact ttatggtgac    540
ggaagtatca gacctaagca gaatcaggat cagtgtttga catccggtag ggatagtgtg    600
tctactgtta ttaacattgt gtcttgttct ggagctagtg gatctcaaag gtgggttttc    660
acaaacgagg gtgctatcct taacttgaag aactctctta tggtggatgt tgctcaggct    720
aaccctaagt tgagaaggat tatcatttac ccagctactg gtaagcctaa ccagatgtgg    780
ttgccagttt tttat                                                     795

<210> SEQ ID NO 33
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n= a, t, g, or c
<220> FEATURE:
<221> NAME/KEY: misc_feature
<222> LOCATION: (6)..(6)
<223> OTHER INFORMATION: n= a, t, g, or c

<400> SEQUENCE: 33
gtnmgngayg aygayttyca                                                 20

<210> SEQ ID NO 34
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (9)..(9)
<223> OTHER INFORMATION: n= a, t, g, or c
<220> FEATURE:
<221> NAME/KEY: misc_feature
<222> LOCATION: (15)..(15)
<223> OTHER INFORMATION: n= a, t, g, or c
```

```
<220> FEATURE:
<221> NAME/KEY: misc_feature
<222> LOCATION: (18)..(18)
<223> OTHER INFORMATION: n= a, t, g, or c

<400> SEQUENCE: 34
atytgrttng gyttnccngt                                                    20

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
cacagcagta ttacagtcga a                                                  21

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
gtctatgtga tgatcttcga ctgt                                               24

<210> SEQ ID NO 37
<211> LENGTH: 254
<212> TYPE: PRT
<213> ORGANISM: Artificial Sequence
<220> FEATURE:
<223> OTHER INFORMATION: mistletoe lectin A1

<400> SEQUENCE: 37
```

Tyr Glu Arg Leu Arg Leu Arg Val Thr His Gln Thr Thr Gly Glu Glu
1               5                   10                  15

Tyr Phe Arg Ph

```
Leu Glu Leu Glu Thr Ser Trp Gly Gln Gln Ser Thr Gln Val Gln His
            195                 200                 205

Ser Thr Asp Gly Val Phe Asn Asn Pro Ile Arg Leu Ala Ile Pro Pro
    210                 215                 220

Gly Asn Phe Val Thr Leu Thr Asn Val Arg Asp Val Ile Ala Ser Leu
225                 230                 235                 240

Ala Ile Met Leu Phe Val Cys Gly Glu Arg Pro Ser Ser Ser
            245                 250

<210> SEQ ID NO 38
<211> LENGTH: 256
<212> TYPE: PRT
<213> ORGANISM: Artificial Sequence
<220> FEATURE:
<223> OTHER INFORMATION: mistletoe lectin A2

<400> SEQUENCE: 38

Tyr Glu Arg Leu Arg Leu Arg Val Thr His

-continued

<400> SEQUENCE: 39

```
Tyr Glu Arg Leu Arg Leu Arg Val Thr His Gln Thr Thr Gly Glu Glu
1               5                   10                  15

Tyr Phe Arg Phe Ile Thr Leu Leu Arg Asp Tyr Val Ser Ser Gly Ser
            20                  25                  30

Phe Ser Asn Glu Ile Pro Leu Leu Arg Gln Ser Thr Ile Pro Val Ser
        35                  40                  45

Asp Ala Gln Arg Phe Val Leu Val Glu Leu Thr Asn Gln Gly Gln Asp
    50                  55                  60

Ser Val Thr Ala Ala Ile Asp Val Thr Asn Ala Tyr Val Val Ala Tyr
65                  70                  75                  80

Gln Ala Gly Asp Gln Ser Tyr Phe Leu Arg Asp Ala Pro Arg Gly Ala
                85                  90                  95

Glu Thr His Leu Phe Thr Gly Thr Thr Arg Ser Ser Leu Pro Phe Asn
            100                 105                 110

Gly Ser Tyr Pro Asp Leu Glu Arg Tyr Ala Gly His Arg Gln Ile Pro
        115                 120                 125

Leu Gly Ile Asp Gln Leu Ile Gln Ser Val Thr Ala Leu Arg Phe Pro
    130                 135                 140

Gly Gly Ser Thr Arg Thr Gln Ala Arg Ser Ile Leu Ile Leu Ile Gln
145                 150                 155                 160

Met Ile Ser Glu Ala Ala Arg Phe Asn Pro Ile Leu Trp Arg Tyr Arg
                165                 170                 175

Gln Tyr Ile Asn Ser Gly Ala Ser Phe Leu Pro Asp Val Tyr Met Leu
            180                 185                 190

Glu Leu Glu Thr Ser Trp Gly Gln Gln Ser Thr Gln Val Gln His Ser
        195                 200                 205

Thr Asp Gly Val Phe Asn Asn Pro Ile Arg Leu Ala Ile Pro Pro Gly
    210                 215                 220

Asn Phe Val Thr Leu Thr Asn Val Arg Asp Val Ile Ala Ser Leu Ala
225                 230                 235                 240

Ile Met Leu Phe Val Cys Gly Glu Arg Pro Ser Ser Ser
                245                 250
```

<210> SEQ ID NO 40
<211> LENGTH: 534
<212> TYPE: PRT
<213> ORGANISM: Artificial Sequence
<220> FEATURE:
<223> OTHER INFORMATION: mistletoe lectin
<220> FEATURE:
<221> NAME/KEY: SITE
<222> LOCATION: (15)..(15)
<223> OTHER INFORMATION: Xaa is Asp or Glu
<220> FEATURE:
<221> NAME/KEY: SITE
<222> LOCATION: (63)..(63)
<223> OTHER INFORMATION: Xaa is Gly or Gln
<220> FEATURE:
<221> NAME/KEY: SITE
<222> LOCATION: (66)..(66)
<223> OTHER INFORMATION: Xaa is Ile or Val
<220> FEATURE:
<221> NAME/KEY: SITE
<222> LOCATION: (75)..(75)
<223> OTHER INFORMATION: Xaa is Leu or Ala
<220> FEATURE:
<221> NAME/KEY: SITE
<222> LOCATION: (114)..(114)
<223> OTHER INFORMATION: Xaa is Asn or Thr

```
<220> FEATURE:
<221> NAME/KEY: SITE
<222> LOCATION: (118)..(118)
<223> OTHER INFORMATION: Xaa is Pro or Thr
<220> FEATURE:
<221> NAME/KEY: SITE
<222> LOCATION: (135)..(135)
<223> OTHER INFORMATION: Xaa is Asp or Glu
<220> FEATURE:
<221> NAME/KEY: SITE
<222> LOCATION: (142)..(142)
<223> OTHER INFORMATION: Xaa is Ser or Thr
<220> FEATURE:
<221> NAME/KEY: SITE
<222> LOCATION: (146)..(146)
<223> OTHER INFORMATION: Xaa is Phe or Tyr
<220> FEATURE:
<221> NAME/KEY: SITE
<222> LOCATION: (153)..(153)
<223> OTHER INFORMATION: Xaa is Thr or Ala
<220> FEATURE:
<221> NAME/KEY: SITE
<222> LOCATION: (178)..(178)
<223> OTHER INFORMATION: Xaa is Ala or Tyr
<220> FEATURE:
<221> NAME/KEY: SITE
<222> LOCATION: (181)..(181)
<223> OTHER INFORMATION: Xaa is Tyr or Asp
<220> FEATURE:
<221> NAME/KEY: SITE
<222> LOCATION: (186)..(186)
<223> OTHER INFORMATION: Xaa is Ala or Glu
<220> FEATURE:
<221> NAME/KEY: SITE
<222> LOCATION: (192)..(192)
<223> OTHER INFORMATION: Xaa is Val or Met
<220> FEATURE:
<221> NAME/KEY: SITE
<222> LOCATION: (220)..(220)
<223> OTHER INFORMATION: Xaa is Ile or Phe
<220> FEATURE:
<221> NAME/KEY: SITE
<222> LOCATION: (225)..(225)
<223> OTHER INFORMATION: Xaa is Pro or Ser
<220> FEATURE:
<221> NAME/KEY: SITE
<222> LOCATION: (226)..(226)
<223> OTHER INFORMATION: Xaa is Pro or Thr
<220> FEATURE:
<221> NAME/KEY: SITE
<222> LOCATION: (233)..(233)
<223> OTHER INFORMATION: Xaa is Thr or Ser
<220> FEATURE:
<221> NAME/KEY: SITE
<222> LOCATION: (237)..(237)
<223> OTHER INFORMATION: Xaa is Asp or Ser
<220> FEATURE:
<221> NAME/KEY: SITE
<222> LOCATION: (288)..(288)
<223> OTHER INFORMATION: Xaa is Asn or Ser
<220> FEATURE:
<221> NAME/KEY: SITE
<222> LOCATION: (291)..(291)
<223> OTHER INFORMATION: Xaa is Cys or Arg
<220> FEATURE:
<221> NAME/KEY: SITE
<222> LOCATION: (326)..(326)
<223> OTHER INFORMATION: Xaa is Gly or Asn
<220> FEATURE:
<221> NAME/KEY: SITE
<222> LOCATION: (365)..(365)
<223> OTHER INFORMATION: Xaa is Gly or Asp
<220> FEATURE:
<221> NAME/KEY: SITE
<222> LOCATION: (427)..(427)
<223> OTHER INFORMATION: Xaa is Gly or Gln
```

```
<220> FEATURE:
<221> NAME/KEY: SITE
<222> LOCATION: (436)..(436)
<223> OTHER INFORMATION: Xaa is Val or Asp
<220> FEATURE:
<221> NAME/KEY: SITE
<222> LOCATION: (440)..(440)
<223> OTHER INFORMATION: Xaa is Gln or Lys
<220> FEATURE:
<221> NAME/KEY: SITE
<222> LOCATION: (443)..(443)
<223> OTHER INFORMATION: Xaa is Gly or missing
<220> FEATURE:
<221> NAME/KEY: SITE
<222> LOCATION: (444)..(444)
<223> OTHER INFORMATION: Xaa is Arg or Lys
<220> FEATURE:
<221> NAME/KEY: SITE
<222> LOCATION: (465)..(465)
<223> OTHER INFORMATION: Xaa is Cys or Ser or Val
<220> FEATURE:
<221> NAME/KEY: SITE
<222> LOCATION: (481)..(481)
<223> OTHER INFORMATION: Xaa is Ala or Gly
<220> FEATURE:
<221> NAME/KEY: SITE
<222> LOCATION: (482)..(482)
<223> OTHER INFORMATION: Xaa is Gly or Ala
<220> FEATURE:
<221> NAME/KEY: SITE
<222> LOCATION: (484)..(484)
<223> OTHER INFORMATION: Xaa is Ser or Gly
<220> FEATURE:
<221> NAME/KEY: SITE
<222> LOCATION: (485)..(485)
<223> OTHER INFORMATION: Xaa is Gly or Ser
<220> FEATURE:
<221> NAME/KEY: SITE
<222> LOCATION: (494)..(494)
<223> OTHER INFORMATION: Xaa is Gly or Tyr
<220> FEATURE:
<221> NAME/KEY: SITE
<222> LOCATION: (501)..(501)
<223> OTHER INFORMATION: Xaa is Asn or Ser or Thr or Lys
<220> FEATURE:
<221> NAME/KEY: SITE
<222> LOCATION: (502)..(502)
<223> OTHER INFORMATION: Xaa is Ser or Gly
<220> FEATURE:
<221> NAME/KEY: SITE
<222> LOCATION: (503)..(503)
<223> OTHER INFORMATION: Xaa is Leu or Pro
<220> FEATURE:
<221> NAME/KEY: SITE
<222> LOCATION: (504)..(504)
<223> OTHER INFORMATION: Xaa is Ala or Met
<220> FEATURE:
<221> NAME/KEY: SITE
<222> LOCATION: (505)..(505)
<223> OTHER INFORMATION: Xaa is Met or Val
<220> FEATURE:
<221> NAME/KEY: SITE
<222> LOCATION: (534)..(534)
<223> OTHER INFORMATION: Xaa is Pro or Phe

<400> SEQUENCE: 40

Tyr Glu Arg Leu Arg Leu Arg Val Thr His Gln Thr Thr Gly Xaa Glu
 1               5                  10                  15

Tyr Phe Arg Phe Ile Thr Leu Leu Arg Asp Tyr Val Ser Ser Gly Ser
                20                  25                  30

Phe Ser Asn Glu Ile Pro Leu Leu Arg Gln Ser Thr Ile Pro Val Ser
            35                  40                  45

Asp Ala Gln Arg Phe Val Leu Val Glu Leu Thr Asn Gln Gly Xaa Asp
        50                  55                  60
```

-continued

```
Ser Xaa Thr Ala Ala Ile Asp Val Thr Asn Xaa Tyr Val Val Ala Tyr
 65              70                  75                  80

Gln Ala Gly Asp Gln Ser Tyr Phe Leu Arg Asp Ala Pro Arg Gly Ala
             85                  90                  95

Glu Thr His Leu Phe Thr Gly Thr Arg Asp Arg Ser Ser Leu Pro
            100                 105                 110

Phe Xaa Gly Ser Tyr Xaa Asp Leu Glu Arg Tyr Ala Gly His Arg Asp
            115                 120                 125

Gln Ile Pro Leu Gly Ile Xaa Gln Leu Ile Gln Ser Val Xaa Ala Leu
        130                 135                 140

Arg Xaa Pro Gly Gly Ser Thr Arg Xaa Gln Ala Arg Ser Ile Leu Ile
145                 150                 155                 160

Leu Ile Gln Met Ile Ser Glu Ala Ala Arg Phe Asn Pro Ile Leu Trp
                165                 170                 175

Arg Xaa Arg Gln Xaa Ile Asn Ser Gly Xaa Ser Phe Leu Pro Asp Xaa
            180                 185                 190

Tyr Met Leu Glu Leu Glu Thr Ser Trp Gly Gln Gln Ser Thr Gln Val
            195                 200                 205

Gln His Ser Thr Asp Gly Val Phe Asn Asn Pro Xaa Arg Leu Ala Ile
    210                 215                 220

Xaa Xaa Gly Asn Phe Val Thr Leu Xaa Asn Val Arg Xaa Val Ile Ala
225                 230                 235                 240

Ser Leu Ala Ile Met Leu Phe Val Cys Gly Glu Arg Pro Ser Ser Ser
                245                 250                 255

Asp Val Arg Tyr Trp Pro Leu Val Ile Arg Pro Val Ile Ala Asp Asp
            260                 265                 270

Val Thr Cys Ser Ala Ser Glu Pro Thr Val Arg Ile Val Gly Arg Xaa
            275                 280                 285

Gly Met Xaa Val Asp Val Arg Asp Asp Asp Phe His Asp Gly Asn Gln
            290                 295                 300

Ile Gln Leu Trp Pro Ser Lys Ser Asn Asn Asp Pro Asn Gln Leu Trp
305                 310                 315                 320

Thr Ile Lys Arg Asp Xaa Thr Ile Arg Ser Asn Gly Ser Cys Leu Thr
                325                 330                 335

Thr Tyr Gly Tyr Thr Ala Gly Val Tyr Val Met Ile Phe Asp Cys Asn
            340                 345                 350

Thr Ala Val Arg Glu Ala Thr Ile Trp Gln Ile Trp Xaa Asn Gly Thr
            355                 360                 365

Ile Ile Asn Pro Arg Ser Asn Leu Val Leu Ala Ala Ser Ser Gly Ile
    370                 375                 380

Lys Gly Thr Thr Leu Thr Val Gln Thr Leu Asp Tyr Thr Leu Gly Gln
385                 390                 395                 400

Gly Trp Leu Ala Gly Asn Asp Thr Ala Pro Arg Glu Val Thr Ile Tyr
            405                 410                 415

Gly Phe Arg Asp Leu Cys Met Glu Ser Asn Xaa Gly Ser Val Trp Val
            420                 425                 430

Glu Thr Cys Xaa Ser Ser Gln Xaa Asn Gln Xaa Xaa Trp Ala Leu Tyr
            435                 440                 445

Gly Asp Gly Ser Ile Arg Pro Lys Gln Asn Gln Asp Gln Cys Leu Thr
    450                 455                 460

Xaa Gly Arg Asp Ser Val Ser Thr Val Ile Asn Ile Val Ser Cys Ser
465                 470                 475                 480
```

```
Xaa Xaa Ser Xaa Xaa Gln Arg Trp Val Phe Thr Asn Glu Xaa Ala Ile
            485                 490                 495

Leu Asn Leu Lys Xaa Xaa Xaa Xaa Xaa Asp Val Ala Gln Ala Asn Pro
            500                 505                 510

Lys Leu Arg Arg Ile Ile Ile Tyr Pro Ala Thr Gly Lys Pro Asn Gln
            515                 520                 525

Met Trp Leu Pro Val Xaa
            530

<210> SEQ ID NO 41
<211> LENGTH: 256
<212> TYPE: PRT
<213> ORGANISM: Artificial Sequence
<220> FEATURE:
<223> OTHER INFORMATION: MLA-chain
<220> FEATURE:
<221> NAME/KEY: SITE
<222> LOCATION: (15)..(15)
<223> OTHER INFORMATION: Xaa is Asp or Glu
<220> FEATURE:
<221> NAME/KEY: SITE
<222> LOCATION: (63)..(63)
<223> OTHER INFORMATION: Xaa is Gly or Gln
<220> FEATURE:
<221> NAME/KEY: SITE
<222> LOCATION: (66)..(66)
<223> OTHER INFORMATION: Xaa is Ile or Val
<220> FEATURE:
<221> NAME/KEY: SITE
<222> LOCATION: (75)..(75)
<223> OTHER INFORMATION: Xaa is Leu or Ala
<220> FEATURE:
<221> NAME/KEY: SITE
<222> LOCATION: (114)..(114)
<223> OTHER INFORMATION: Xaa is Asn or Thr
<220> FEATURE:
<221> NAME/KEY: SITE
<222> LOCATION: (118)..(118)
<223> OTHER INFORMATION: Xaa is Pro or Thr
<220> FEATURE:
<221> NAME/KEY: SITE
<222> LOCATION: (135)..(135)
<223> OTHER INFORMATION: Xaa is Asp or Glu
<220> FEATURE:
<221> NAME/KEY: SITE
<222> LOCATION: (142)..(142)
<223> OTHER INFORMATION: Xaa is Ser or Thr
<220> FEATURE:
<221> NAME/KEY: SITE
<222> LOCATION: (146)..(146)
<223> OTHER INFORMATION: Xaa is Phe or Tyr
<220> FEATURE:
<221> NAME/KEY: SITE
<222> LOCATION: (153)..(153)
<223> OTHER INFORMATION: Xaa is Thr or Ala
<220> FEATURE:
<221> NAME/KEY: SITE
<222> LOCATION: (178)..(178)
<223> OTHER INFORMATION: Xaa is Ala or Tyr
<220> FEATURE:
<221> NAME/KEY: SITE
<222> LOCATION: (181)..(181)
<223> OTHER INFORMATION: Xaa is Tyr or Asp
<220> FEATURE:
<221> NAME/KEY: SITE
<222> LOCATION: (186)..(186)
<223> OTHER INFORMATION: Xaa is Ala or Glu
<220> FEATURE:
<221> NAME/KEY: SITE
<222> LOCATION: (192)..(192)
<223> OTHER INFORMATION: Xaa is Val or Met
<220> FEATURE:
<221> NAME/KEY: SITE
<222> LOCATION: (220)..(220)
<223> OTHER INFORMATION: Xaa is Ile or Phe
```

```
<220> FEATURE:
<221> NAME/KEY: SITE
<222> LOCATION: (225)..(225)
<223> OTHER INFORMATION: Xaa is Pro or Ser
<220> FEATURE:
<221> NAME/KEY: SITE
<222> LOCATION: (226)..(226)
<223> OTHER INFORMATION: Xaa is Pro or Thr
<220> FEATURE:
<221> NAME/KEY: SITE
<222> LOCATION: (233)..(233)
<223> OTHER INFORMATION: Xaa is Thr or Ser
<220> FEATURE:
<221> NAME/KEY: SITE
<222> LOCATION: (237)..(237)
<223> OTHER INFORMATION: Xaa is Asp or Ser

<400> SEQUENCE: 41

Tyr Glu Arg Leu Arg Leu Arg Val Thr His Gln Thr Thr Gly Xaa Glu
1               5                   10                  15

Tyr Phe Arg Phe Ile Thr Leu Leu Arg Asp Tyr Val Ser Ser Gly Ser
            20                  25                  30

Phe Ser Asn Glu Ile Pro Leu Leu Arg Gln Ser Thr Ile Pro Val Ser
        35                  40                  45

Asp Ala Gln Arg Phe Val Leu Val Glu Leu Thr Asn Gln Gly Xaa Asp
    50                  55                  60

Ser Xaa Thr Ala Ala Ile Asp Val Thr Asn Xaa Tyr Val Val Ala Tyr
65                  70                  75                  80

Gln Ala Gly Asp Gln Ser Tyr Phe Leu Arg Asp Ala Pro Arg Gly Ala
                85                  90                  95

Glu Thr His Leu Phe Thr Gly Thr Thr Arg Asp Arg Ser Ser Leu Pro
                100                 105                 110

Phe Xaa Gly Ser Tyr Xaa Asp Leu Glu Arg Tyr Ala Gly His Arg Asp
            115                 120                 125

Gln Ile Pro Leu Gly Ile Xaa Gln Leu Ile Gln Ser Val Xaa Ala Leu
    130                 135                 140

Arg Xaa Pro Gly Gly Ser Thr Arg Xaa Gln Ala Arg Ser Ile Leu Ile
145                 150                 155                 160

Leu Ile Gln Met Ile Ser Glu Ala Ala Arg Phe Asn Pro Ile Leu Trp
                165                 170                 175

Arg Xaa Arg Gln Xaa Ile Asn Ser Gly Xaa Ser Phe Leu Pro Asp Xaa
            180                 185                 190

Tyr Met Leu Glu Leu Glu Thr Ser Trp Gly Gln Gln Ser Thr Gln Val
            195                 200                 205

Gln His Ser Thr Asp Gly Val Phe Asn Asn Pro Xaa Arg Leu Ala Ile
    210                 215                 220

Xaa Xaa Gly Asn Phe Val Thr Leu Xaa Asn Val Arg Xaa Val Ile Ala
225                 230                 235                 240

Ser Leu Ala Ile Met Leu Phe Val Cys Gly Glu Arg Pro Ser Ser Ser
                245                 250                 255
```